(12) United States Patent
Jeltsch et al.

(10) Patent No.: US 10,711,045 B2
(45) Date of Patent: Jul. 14, 2020

(54) ISOLATION OF NUCLEOSOMES HAVING MULTIPLE-MODIFIED HISTONE PROTEIN OCTAMERS

(71) Applicant: Universität Stuttgart, Stuttgart (DE)

(72) Inventors: Albert Jeltsch, Rutesheim (DE); Goran Kungulovski, Skopje (MK); Rebekka Mauser, Ludwigsburg (DE)

(73) Assignee: Universität Stuttgart, Stuttgart (DE)

( * ) Notice: Subject to any disclaimer, the term of this patent is extended or adjusted under 35 U.S.C. 154(b) by 54 days.

(21) Appl. No.: 15/561,486

(22) PCT Filed: Mar. 15, 2016

(86) PCT No.: PCT/EP2016/055605
§ 371 (c)(1),
(2) Date: Sep. 25, 2017

(87) PCT Pub. No.: WO2016/156033
PCT Pub. Date: Oct. 6, 2016

(65) Prior Publication Data
US 2018/0066029 A1     Mar. 8, 2018

(30) Foreign Application Priority Data
Mar. 30, 2015   (EP) .................................... 15161621

(51) Int. Cl.
| | | |
|---|---|---|
| G01N 33/50 | (2006.01) | |
| C07K 14/47 | (2006.01) | |
| C07K 14/435 | (2006.01) | |
| G01N 33/573 | (2006.01) | |
| G01N 33/68 | (2006.01) | |

(52) U.S. Cl.
CPC ........ *C07K 14/4702* (2013.01); *C07K 14/435* (2013.01); *G01N 33/573* (2013.01); *G01N 33/6842* (2013.01); *C07K 2319/20* (2013.01); *C07K 2319/80* (2013.01); *G01N 2440/12* (2013.01)

(58) Field of Classification Search
None
See application file for complete search history.

(56) References Cited

U.S. PATENT DOCUMENTS

2003/0049649 A1* 3/2003 Wolffe ............... C07K 14/4702
435/6.12

FOREIGN PATENT DOCUMENTS

| WO | 2003070894 A2 | 8/2003 | |
|---|---|---|---|
| WO | 2004044168 A2 | 5/2004 | |
| WO | WO-2004044168 A2 * | 5/2004 | ............. C07K 14/47 |
| WO | 2014144303 A1 | 9/2014 | |
| WO | WO-2014144303 A1 * | 9/2014 | ......... C07K 14/4702 |

OTHER PUBLICATIONS

Van Nuland et al in "Nucleosomal DNA binding drives the recognition of H3K36-methylated nucleosomes by the PSIP1-PWWP domain" (Epigenetics & Chromatin 2013 vol. 6: 12 published May 8, 2013) in view of WO 2014/144303 (IDS reference). (Year: 2013).*
Meslamani et al, "ChEpiMod: a knowledgebase for chemical modulators of epigenome reader domains" (Bioinformatics, vol. 30, Issue 10, May 15, 2014, pp. 1481-1483; published Jan. 27, 2014) (Year: 2014).*
Wu et al "Structural and Histone Binding Ability Characterizations of Human PWWP Domains" (PLoS One Jun. 2011, vol. 6, No. 6, e18919 pp. 1-12; published Jun. 20, 2011) (Year: 2011).*
Soldi & Bonaldi in "The ChroP Approach Combines ChIP and Mass Spectrometry to Dissect Locus-specific Proteomic Landscapes of Chromatin" (J. Vis. Exp. vol. 86, e51220, pp. 1-14, published Apr. 11, 2014). (Year: 2014).*
Bock, et al., "Application of Celluspots peptide arrays for the analysis of the binding specificity of epigenetic reading domains to modified histone tails", BMC Biochemistry 12(48), 12 pages (2011).
Bock, et al., "Detailed specificity analysis of antibodies binding to modified histone tails with peptide arrays", Epigenetics 6 (2), 256-263 (2011).
Brand, et al., "Analysis of epigenetic modifications of chromatin at specific gene loci by native chromatin immunoprecipitation of nucleosomes isolated using hydroxyapatite chromatography", Nature Protocols 3(3), 398-409 (2008).
ENCODE-Consortium, "An integrated encyclopedia of DNA elements in the human genome", Nature 489(57), 18 pages (2012).
Ernst, et al., "Mapping and analysis of chromatin state dynamics in nine human cell types", Nature 473(43), 9 pages (2011).
Griffon, et al., "Integrative analysis of public ChIP-seq experiments reveals a complex multi-cell regulatory landscape", Nucleic Acids Research 43(4), e27, 14 pages (2015).

(Continued)

*Primary Examiner* — Catherine S Hibbert
(74) *Attorney, Agent, or Firm* — Viksnins Harris Padys Malen LLP

(57) ABSTRACT

The invention discloses the use of an artificial protein for isolating a nucleosome, the nucleosome comprising a multiple-modified histone protein octamer, wherein the artificial protein comprises a first histone modification binding domain of 50 to 200 amino acids binding to a first histone modification, a second histone modification binding domain of 50 to 200 amino acids binding to a second histone modification, a linker of 5 to 50 amino acids connecting the first and the second histone modification binding domain, and an affinity tag. Further disclosed are a nucleic acid encoding the artificial protein, a host cell comprising the nucleic acid and a kit for isolating a nucleosome, the nucleosome comprising a multiple-modified histone protein octamer. Further disclosed is an in-vitro method for isolating a nucleosome having a first and a second histone modification.

9 Claims, 10 Drawing Sheets
Specification includes a Sequence Listing.

(56) References Cited

OTHER PUBLICATIONS

Halachev, et al., "EpiExplorer: live exploration and global analysis of large epigenomic datasets", Genome Biology 13, R96, 14 pages (2012).
International Search Report, for PCT/EP2016/055605, 3 pages, dated May 6, 2016.
Jeltsch, et al., "Site-Directed Mutagenesis by Polymerase Chain Reaction", Methods in Molecular Biology: In Vitro Mutagenesis Protocols 182, 85-94, Humana Press, New York (2002).
Kallio, et al., "Chipster: user-friendly analysis software for microarray and other high-throughput data", BMC Genomics 12 (507), 14 pages (2011).
Kent, et al., "The human genome browser at UCSC", Genome Research 12, 996-1006 (2002).
Langmead, et al., "Ultrafast and memory-efficient alignment of short DNA sequences to the human genome", Genome Biology 10, R25, 10 pages (2009).
Lau, et al., "Elucidating combinatorial histone modifications and crosstalks by coupling histone-modifying enzyme with biotin ligase activity", Nucleic Acids Research 41(3), e49, 10 pages (2013).
Ramirez, et al., "deepTools: a flexible platform for exploring deep-sequencing data", Nucleic Acids Research 42, W187-W191 (2014).
Rathert, et al., "Protein lysine methyltransferase G9a acts on non-histone targets", Nature Chemical Biology 4(6), 344-346 (2008).
Simon, et al., "The site-specific installation of methyl-lysine analogs into recombinant histones", Cell 128, 1003-1012 (2007).
Trapnell, et al., "Differential gene and transcript expression analysis of RNA-seq experiments with TopHat and Cufflinks", Nat Protoc 7(3), 562-578 (2012).
Welch, et al., "ChIP-Enrich: gene set enrichment testing for ChIP-seq data", Nucleic Acids Research e105, 13 pages (2014).
Ye, et al., "seqMINER: an integrated ChIP-seq data interpretation platform", Nucleic Acids Research 39(6), e35, 10 pages (2011).

\* cited by examiner

|    | PM | P*M | P |
|----|-----|------|------|
| PM | 1 | 0.54 | 0.52 |
| P*M | | 1 | -0.18 |
| P | | | 1 |

ISOLATION OF NUCLEOSOMES HAVING MULTIPLE-MODIFIED HISTONE PROTEIN OCTAMERS

CROSS-REFERENCE TO RELATED APPLICATION(S)

This application claims priority to European Application No. 15161621.6 filed on 30 Mar. 2015.

SEQUENCE LISTING

The instant application contains a Sequence Listing, which has been submitted in ASCII format via EFS-Web and is hereby incorporated by reference in its entirety. Said ASCII copy, created on Sep. 12, 2017, is named 18050_013US1 SL.txt and is 136,008 bytes in size.

FIELD OF THE INVENTION

The present invention relates to the use of an artificial protein for isolating a nucleosome, the nucleosome comprising a multiple-modified histone protein octamer. The invention also relates to a nucleic acid encoding an artificial protein, a host cell comprising the nucleic acid and a kit for isolating a nucleosome. The invention further relates to an in-vitro method for isolating a nucleosome having a first and a second histone modification.

BACKGROUND OF THE INVENTION

Post-translational modifications of histone proteins, such as methylation and acetylation, play an important role in the regulation of gene expression and other chromatin-associated processes. They may also be involved in various diseases such as autoimmune diseases, developmental disorders and cancer. To date, more than 100 histone modifications are known. They occur in complex patterns, forming the so-called "histone code". With a view to deciphering this code and gain a better understanding of its role in human disease, the identification and characterisation of co-occurring histone modifications is an area of intense research.

The isolation of nucleosomes having multiple co-occurring histone modifications is used to detect the presence of co-occurring histone modifications. It also facilitates their further analysis. Nucleosomes having multiple-modified histone protein octamers can be isolated by consecutive chromatin immunoprecipitation (ChIP) assays: First, a ChIP assay using an antibody directed to a first histone modification is performed. The precipitated nucleosomes are then eluted and subjected to a second ChIP assay using an antibody directed to a second histone modification. Consecutive ChIP assays are not only time-consuming; they also require a lot of starting material and are technically difficult to perform. Moreover, consecutive ChIP assays have a poor sensitivity and the DNA recovered from the isolated nucleosomes cannot be analysed by next-generation sequencing to date.

Therefore, new tools and methods for isolating nucleosomes having multiple-modified histone protein octamers are needed that overcome the current limitations.

SUMMARY OF THE INVENTION

In a first aspect, the invention relates to the use of an artificial protein for isolating a nucleosome, the nucleosome comprising a multiple-modified histone protein octamer, wherein the artificial protein comprises a first histone modification binding domain of 50 to 200 amino acids binding to a first histone modification, a second histone modification binding domain of 50 to 200 amino acids binding to a second histone modification, a linker of 5 to 50 amino acids connecting the first and the second histone modification binding domain, and an affinity tag.

In a second aspect, the present invention relates to a nucleic acid encoding an artificial protein, wherein the artificial protein comprises a first histone modification binding domain of 50 to 200 amino acids binding to a first histone modification, a second histone modification binding domain of 50 to 200 amino acids binding to a second histone modification, a linker of 5 to 50 amino acids connecting the first and the second histone modification binding domain, and an affinity tag.

In a third aspect, the present invention relates to a host cell comprising the nucleic acid of the invention.

In a further aspect, the invention relates to a kit for isolating a nucleosome, the nucleosome comprising a multiple-modified histone protein octamer, wherein the kit comprises an artificial protein, wherein the artificial protein comprises a first histone modification binding domain of 50 to 200 amino acids binding to a first histone modification, a second histone modification binding domain of 50 to 200 amino acids binding to a second histone modification, a linker of 5 to 50 amino acids connecting the first and the second histone modification binding domain, and an affinity tag.

In a further aspect, the invention relates to an in-vitro method for isolating a nucleosome having a first and a second histone modification, the method comprising the steps of (a) providing an artificial protein, wherein the artificial protein comprises a first histone modification binding domain of 50 to 200 amino acids binding to the first histone modification, a second histone modification binding domain of 50 to 200 amino acids binding to the second histone modification, a linker of 5 to 50 amino acids connecting the first and the second histone modification binding domain, and an affinity tag; (b) contacting the artificial protein with a sample comprising nucleosomes to allow formation of a complex of the artificial protein and a nucleosome having the first and the second histone modification; and (c) isolating the complex.

BRIEF DESCRIPTION OF THE DRAWINGS

FIG. 5 shows the Spearman correlation coefficient of next-generation sequencing of recovered DNA. The DNA was recovered from nucleosomes isolated using the artificial protein PM, its variant having a pocket mutation in the first histone modification binding domain (P*M) or a single PWWP domain of Dnmt3a (P).

DETAILED DESCRIPTION OF THE INVENTION

Figure 1:
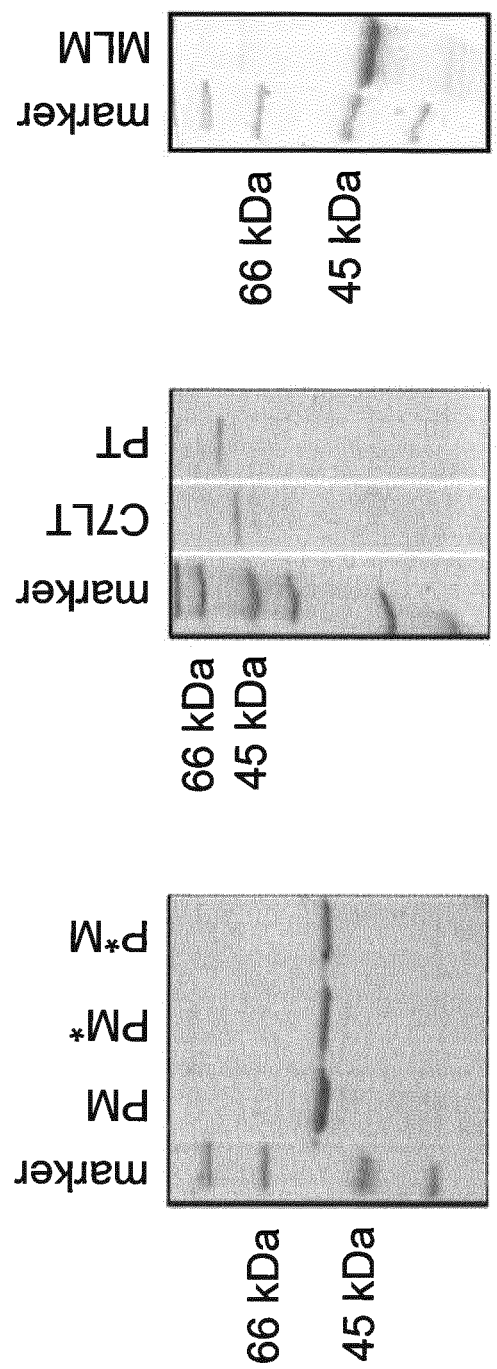
FIG. 1 shows an SDS-PAGE of purified artificial proteins stained with Coomassie Brilliant Blue.

In a first aspect, the invention relates to the use of an artificial protein for isolating a nucleosome, the nucleosome comprising a multiple-modified histone protein octamer, wherein the artificial protein comprises a first histone modification binding domain of 50 to 200 amino acids binding to a first histone modification, a second histone modification binding domain of 50 to 200 amino acids binding to a second histone modification, a linker of 5 to 50 amino acids connecting the first and the second histone modification binding domain, and an affinity tag.

The histone protein octamer of a nucleosome is composed of two copies of histone proteins H3, H4, H2A and H2B, respectively. The term "histone modification" as used herein refers to any covalently bound chemical entity that is post-translationally added to an amino acid residue of a histone protein in the histone protein octamer as well as combinations thereof that can be bound by a given histone modification binding domain. Common histone modifications comprise methylation, acetylation and ubiquitylation of one or more lysine residues, methylation of one or more arginine residues and phosphorylation of one or more serine and threonine residues. Further histone modifications comprise SUMOylation, crotonylation, butyrylation and propionylation of lysine residues, citrullination and ADP-ribosylation of arginine residues, and glycosylation of serine and threonine residues. Lysine residues can be mono-, di- or trimethylated while arginine residues can be mono- or dimethylated. Therefore, the term "methylation" as used herein comprises monomethylation, dimethylation and trimethylation. Histone modifications may co-occur in complex patterns, such that nucleosomes often comprise a multiple-modified histone protein octamer.

The artificial protein comprises a first histone modification binding domain and a second histone modification binding domain of 50 to 200 amino acids each. The term "histone modification binding domain" as used herein refers to any amino acid polymer that, when folded into its three-dimensional structure, forms a binding pocket that can specifically interact with one or more histone modifications. The term comprises naturally occurring as well as modified, engineered and/or de novo designed histone modification binding domains. The histone modification binding domain may be based on a human histone modification binding domain or on a histone modification binding domain from another species such as mouse, rat or yeast (e.g. *Schizosaccharomyces pombe*). Histone modification binding domains are also known as reading domains or histone modification interacting domains (HMIDs). Histone modification binding domains specifically bind one or more histone modifications in a non-covalent manner. Non-covalent binding is mediated for example by van der Waals forces, hydrophobic interactions or electrostatic interactions such as formation of hydrogen bonds. The binding comprises specific protein-protein-interactions between the modified histone proteins and the artificial protein.

Histone modification binding domains differ in their binding profiles. There are domains that bind a single histone modification such as bromodomains binding to an acetylated lysine residue. The binding of histone modification binding domains may also depend on more than a single histone modification. For example, the HP1 beta chromodomain binds H3K9me2/3 only if H3S10 is not phosphorylated. The ADD domain of ATRX binds H3K9me3 only if H3K4 is not modified. Further, histone modification binding domains binding to methylated lysine residues often bind to dimethylated as well as trimethylated lysine residues such as H3K9me2 and H3K9me3. Binding profiles may be even more manifold. For example, the PHD domain binds H3K4me3, H3K4me2 and H3K9me3.

Therefore, the term "histone modification" also refers to combinations of chemical entities that are covalently bound to amino acid residues of a histone protein in the histone protein octamer and that can be bound by a given histone modification binding domain.

The first and the second histone modification binding domain allow the artificial protein to interact with both the first and the second histone modification at the same time, thereby facilitating a dual readout of the two histone modifications. Accordingly, the artificial protein can be used to detect the presence of multiple histone modifications on one single nucleosome.

The first and the second histone modification binding domain may be copies of the same domain or different domains giving rise to homodimeric or heterodimeric artificial proteins, respectively.

The artificial protein further comprises a linker of 5 to 50 amino acids connecting the first and the second histone modification binding domain. The linker may be an artificially designed amino acid sequence or a linker derived from a naturally occurring amino acid sequence connecting two protein domains in a protein as for example the linker that connects the PWWP domain and the ADD domain in the DNA (cytosine-5-)-methyltransferase 3 alpha (Dnmt3a) protein. The linker can also be composed of a first portion corresponding to a naturally occurring amino acid sequence and a second portion being an artificially designed amino acid sequence. The linker preferably facilitates a flexible movement of the first and the second histone modification binding domain with respect to one another. Depending on the spatial arrangement of the first and the second histone modification within the histone protein octamer, a flexible connection of the two histone modification binding domains will enable independent interaction of the first and the second histone modification binding domain with their respective histone modifications on a single nucleosome. In other words, the linker should be sufficiently flexible to allow simultaneous entry of the first and the second histone modification from the same nucleosome in the respective histone modification binding pockets of the first and the second histone modification binding domain. This may be advantageous for the use of the artificial protein since histone modifications are generally located in flexible regions of histone proteins (so-called "histone tails") that stick out from the surface of the core of the nucleosome. In case the first and the second histone modification are located close to each other within the histone protein octamer, the linker may also be rigid.

The possibility of simultaneous entry of the first and the second histone modification from the same nucleosome in the respective histone modification binding pockets of the artificial protein can be verified for example by side by side comparison of next-generation sequencing data of DNA recovered from isolated nucleosomes. The latter may be obtained using the artificial protein and control proteins which comprise only one of the first and the second histone modification binding domains. Determination of the three-dimensional structure of the artificial protein, for example by X-ray structure analysis, may also be applied to determine the flexibility of the first and the second histone modification binding domain with respect to one another.

The artificial protein further comprises an affinity tag. The term "affinity tag" as used herein refers to any amino acid sequence that is suitable for protein purification and/or protein detection using an affinity technique. For example, the affinity tag can be a glutathione-S-transferase (GST) tag or a polyhistidine-tag. The affinity tag is preferably located at the N-terminus or at the C-terminus of the artificial protein. In a preferred embodiment, the artificial protein comprises more than one affinity tag. Additional affinity tags may enhance protein purification and/or protein detection. The artificial protein preferably comprises at least two different affinity tags. This broadens the range of affinity techniques that can be employed for purifying and/or detecting the artificial protein.

The inventors have successfully isolated nucleosomes comprising two defined histone modifications. To do so, the artificial protein was expressed in *Escherichia coli* and shown to be able to interact with native nucleosomes. It was found that the artificial protein favors binding to nucleosomes when both the first and the second histone modification are present. In line with this finding, the inventors successfully used the artificial protein for isolating nucleosomes which comprise both the first and the second histone modification in a single chromatin precipitation assay at the same time. This confirms that the artificial protein is a useful tool for detecting combinations of histone modifications that co-occur on the same nucleosome.

Thus, one advantage of the invention compared to consecutive ChIP assays is that the use of the artificial protein allows the detection of two or more co-occurring histone modifications on the same nucleosome at the same time in a single step. This is facilitated by specific binding of the artificial protein to multiple-modified histone protein octamers. Specific binding to multiple-modified histone protein octamers means that the artificial protein does not bind histone protein octamers having only one of the first and the second histone modification or neither of the two histone modifications. The inventors found that the bivalent binding of the artificial protein to multiple-modified histone protein octamers leads to a synergistic effect, which results in higher binding affinity of the artificial protein to nucleosomes comprising both the first and the second histone modification compared to nucleosomes comprising only one of two histone modifications. This is believed to be due to multidentate binding of the first and the second histone modification binding domain to their respective target histone modifications, which in turn leads to an increased avidity of the artificial protein to the first and the second histone modification.

The specific binding of the artificial protein to nucleosomes comprising both the first and the second histone modification can be verified for example by side by side comparison of next-generation sequencing data of DNA recovered from isolated nucleosomes. The latter may be obtained using the artificial protein and control proteins which comprise only one of the first and the second histone modification binding domains. Specific binding of the artificial protein to nucleosomes comprising both the first and the second histone modification allows the specific isolation of nucleosomes comprising multiple-modified histone protein octamers.

Another advantage of the use according to the invention is that only small amounts of nucleosome-comprising starting material are required. The term "small amount" as used herein refers to an amount of 10-30 µg of nucleosomes based on DNA absorbance. This is equivalent to chromatin isolated from 1-4 million human cells and typically used in a single ChIP assay. For consecutive ChIP assays, higher amounts of starting material are needed. Since the use of the artificial protein allows the isolation of a nucleosome having two or more co-occurring histone modifications in a single step, material is lost only once. Consecutive ChIP assays comprise at least two consecutive steps so that loss of material occurs at least twice. Thus, the use according to the invention requires less nucleosome-comprising starting material compared to consecutive ChIP assays.

Due to the use of the artificial protein, the isolation of nucleosomes is also technically easy to perform, for example by chromatin precipitation.

Further, DNA recovered from the isolated nucleosomes can be analysed by commonly used methods such as quantitative PCR. Importantly, the DNA can also be analysed by next-generation sequencing, which is not possible when nucleosomes are isolated by consecutive ChIP assays. Consecutive ChIP assays do not yield sufficient amounts of DNA for performing next-generation sequencing. The sequenced DNA can be mapped and used to study the co-occurrence of histone modifications on a genome-wide or locus-specific scale.

DNA analysis by quantitative PCR leads to quantitatively accurate results, however, it is limited to pre-selected DNA loci of around 150 base pairs. Therefore, quantitative PCR is almost always hypothesis-driven since the DNA loci for which information is generated need to be determined beforehand when primer sequences are selected. The same applies to simple sequencing techniques such as Sanger sequencing. In contrast, next-generation sequencing facilitates hypothesis-free DNA analysis as a signal can be present anywhere in the genome. In this way, a genome-wide overview of the co-occurrence of histone modifications is obtained.

Taken together, the use according to the invention provides an improved strategy for analysing complex patterns of histone modifications that co-occur on the same nucleosome. Given that specific combinations of histone modifications may be associated with unique biological functions, the use according to the invention will aid efforts to uncover the role of multiple-modified histone protein octamers in the regulation of gene expression and other chromatin-associated processes as well as in human disease.

In a preferred embodiment, the first and the second histone modification binding domain are different from each other. This provides a heterodimeric artificial protein recognizing two different histone modifications, for example on one single histone protein (in cis) or on different copies of the respective histone protein (in trans) in the histone protein octamer. In contrast, homodimeric artificial proteins can only detect the presence of a certain histone modification in trans, namely on the two different copies of the respective histone protein in the histone protein octamer.

In a preferred embodiment, the first and the second histone modification binding domain are copies of the same domain. This provides a homodimeric artificial protein for isolating nucleosomes comprising the respective histone modification in multiple copies. In addition, homodimeric artificial proteins are particularly useful if an enhanced binding strength and/or an enhanced specificity of a given histone modification binding domain are desired. Since histone modifications generally occur in clusters, homodimeric artificial proteins bind stronger and with a higher specificity to the respective histone modification compared to the corresponding single histone modification binding domain.

The dissociation constants of histone modification binding domains for binding to their respective histone modification are generally in the high nanomolar to low micromolar range. Antibodies have dissociation constants ranging from low nanomolar to low micromolar range. Nevertheless, the inventors found that the dissociation constants of histone modification binding domains are strong enough for isolating nucleosomes.

The dissociation constants of the first and the second histone modification binding domain may be considerably different from each other. For example, the inventors found that a difference in dissociation constants of about 100-fold between the first and the second histone modification binding domain does not interfere with the use according to the invention.

In a preferred embodiment, the artificial protein comprises a linker of 14 to 35 amino acids, more preferred 21 to 27 amino acids. The inventors found that linkers of this length are particularly suitable for the use of the artificial protein according to the invention. For example, the inventors have used linkers having 14, 21 and 27 amino acids, respectively, for obtaining a flexible connection of the two histone modification binding domains. Since histone modifications are generally located in flexible regions of histone proteins, a flexible linker may expedite simultaneous binding of the artificial protein to the first and the second histone modification.

The necessary minimum length of the linker will depend on the spatial arrangement of the histone modification binding pockets in the three-dimensional structure of the artificial protein and on the position at which the linker emerges from each three-dimensional histone modification binding domain. In general, one amino acid can bridge at most about 3.5 Angstrom (this is the case in beta-strands of proteins in which the peptide bonds between two amino acids are almost fully extended).

The linker may further serve to improve the solubility of the artificial protein. To this end, the amino acid sequence of the linker preferably comprises proline, alanine, glutamine, glutamic acid, lysine and/or serine. The solubility of the artificial protein is particularly important for efficient recombinant production and purification of the artificial protein.

In a preferred embodiment, the first and/or the second histone modification is selected from the group consisting of methylation, phosphorylation, acetylation, and ubiquitylation. Methylation, phosphorylation, acetylation, and ubiquitylation of amino acid residues are common histone modifications. For many of these modifications respective histone modification binding domains are known.

In a preferred embodiment, the first and/or the second histone modification binding domain is selected from the group consisting of 14-3-3 domain, ADD domain, ankyrin, BAH domain, BIR domain, BRCT domain, tandem BRCT domain, bromodomain, double bromodomain, chromobarrel, chromodomain, double chromodomain, double PHD finger domain, MBT domain, PID domain, PHD domain, double PH domain, PWWP domain, royal family domain, Tudor domain, tandem Tudor domain, WD40 domain, and zinc finger CW domain.

The term "BAH domain" refers to bromo adjacent homology domain. The term "royal family domain" refers to a subclass of histone modification binding domains comprising Tudor domains, chromodomains, MBT domains and PWWP domains.

In a preferred embodiment, the first histone modification binding domain is the PWWP domain of Dnmt3a and the second histone modification binding domain is the chromodomain of MPP8.

An overview of preferred combinations of the first and the second histone modification binding domain is shown in Table 1.

TABLE 1

Preferred combinations of the first and the second histone modification binding domain

| No. | First histone modification binding domain | Second histone modification binding domain |
|---|---|---|
| 1 | PWWP domain of Dnmt3a | chromodomain of MPP8 |
| 2 | chromodomain of MPP8 | PWWP domain of Dnmt3a |
| 3 | PWWP domain of Dnmt3a | PWWP domain of Dnmt3a |
| 4 | chromodomain of MPP8 | chromodomain of MPP8 |
| 5 | chromodomain of CBX7 | PHD domain of TAF3 |
| 6 | PHD domain of TAF3 | chromodomain of CBX7 |
| 7 | PWWP domain of Dnmt3a | PHD domain of TAF3 |
| 8 | PHD domain of TAF3 | PWWP domain of Dnmt3a |
| 9 | PWWP domain of Dnmt3a | chromodomain of CBX7 |
| 10 | chromodomain of CBX7 | PWWP domain of Dnmt3a |
| 11 | chromodomain of CBX7 | chromodomain of MPP8 |
| 12 | chromodomain of MPP8 | chromodomain of CBX7 |
| 13 | PWWP domain of Dnmt3a | ADD domain of ATRX |
| 14 | ADD domain of ATRX | PWWP domain of Dnmt3a |
| 15 | chromodomain of MPP8 | double Tudor domain of JMJD2A |
| 16 | double Tudor domain of JMJD2A | chromodomain of MPP8 |

Dnmt3a refers to DNA (cytosine-5-)-methyltransferase 3 alpha. MPP8 refers to M-Phase Phosphoprotein 8. CBX7 refers to chromobox homolog 7. TAF3 refers to TATA Box Binding Protein-Associated Factor 3. ATRX refers to Alpha thalassemia/mental retardation syndrome X-linked. JMJD2A is a member of the Jumonji domain 2 (JMJD2) family.

The artificial protein comprising the chromodomain of CBX7 and the PHD domain of TAF3 binds to H3K27me3 and H3K4me3. This combination of histone modifications is also known as "bivalent" state and has a high medical relevance. It was found to occur at developmental genes in embryonic stem cells and to be important for cell differentiation.

In a preferred embodiment, the first and the second histone modification are chemically different. For example, the first histone modification is a methylation while the second histone modification is an acetylation. This is particularly useful to further reveal the complex patterns of histone modifications that co-occur on the same nucleosome.

The use according to the invention may also be applied for identifying novel combinations of co-occurring histone modifications by selecting the first and the second histone modification binding domain accordingly. Therefore, in a preferred embodiment, the co-occurrence of the first and the second histone modification has not been described yet. As an example, the artificial protein comprising the PWWP domain of Dnmt3a and the chromodomain of CBX7 binds to H3K36me3 and H3K27me3. These two histone modifications were previously considered mutually exclusive.

In a second aspect, the present invention relates to a nucleic acid encoding an artificial protein, wherein the artificial protein comprises a first histone modification binding domain of 50 to 200 amino acids binding to a first histone modification, a second histone modification binding domain of 50 to 200 amino acids binding to a second histone modification, a linker of 5 to 50 amino acids connecting the first and the second histone modification binding domain, and an affinity tag.

The nucleic acid may be DNA or RNA. The nucleic acid is used to produce the artificial protein in transgenic host cells or transgenic organisms such as bacteria.

In a third aspect, the present invention relates to a host cell comprising the nucleic acid of the invention.

The host cell is used to produce the artificial protein. Therefore, the term "host cell" as used herein refers to any cell that is suitable for protein production. The host cell is preferably a bacterial cell such as *Escherichia coli* (*E. coli*).

In a further aspect, the invention relates to a kit for isolating a nucleosome, the nucleosome comprising a multiple-modified histone protein octamer, wherein the kit comprises an artificial protein, wherein the artificial protein comprises a first histone modification binding domain of 50 to 200 amino acids binding to a first histone modification, a second histone modification binding domain of 50 to 200 amino acids binding to a second histone modification, a linker of 5 to 50 amino acids connecting the first and the second histone modification binding domain, and an affinity tag.

The kit of the invention provides a tool for detecting two or more co-occurring histone modifications on the same nucleosome at the same time in a single step. Due to the higher binding affinity of the artificial protein to nucleosomes having both the first and the second histone modification compared to nucleosomes having only one of the two histone modifications, the kit facilitates the specific isolation of nucleosomes comprising multiple-modified histone protein octamers. The isolation of nucleosomes using the kit of the invention is technically easy to perform, for example by chromatin precipitation, and requires only small amounts of starting material. Accordingly, the kit of the invention is particularly suited for a comprehensive analysis of complex patterns of histone modifications that co-occur on the same nucleosome. The analysis can be complemented by next-generation sequencing of the DNA recovered from the isolated nucleosomes.

In a further aspect, the invention relates to an in-vitro method for isolating a nucleosome having a first and a second histone modification, the method comprising the steps of (a) providing an artificial protein, wherein the artificial protein comprises a first histone modification binding domain of 50 to 200 amino acids binding to the first histone modification, a second histone modification binding domain of 50 to 200 amino acids binding to the second histone modification, a linker of 5 to 50 amino acids connecting the first and the second histone modification binding domain, and an affinity tag; (b) contacting the artificial protein with a sample comprising nucleosomes to allow formation of a complex of the artificial protein and a nucleosome having the first and the second histone modification; and (c) isolating the complex.

The method of the invention is based on the inventors' finding that the artificial protein can be used for specifically isolating nucleosomes having multiple histone modifications at the same time in a single step with high efficiency. This is facilitated by the specific binding of the artificial protein to nucleosomes having both the first and the second histone modification compared to nucleosomes having only one of two histone modifications.

The method of the invention requires only small amounts of nucleosome-comprising starting material and is technically easy to perform. Further, DNA recovered from the isolated nucleosomes can be analysed by commonly used methods such as quantitative PCR, but also by next-generation sequencing.

The complex is formed by binding of the first histone modification binding domain to the first histone modification and binding of the second histone modification binding domain to the second histone modification. Complex-forming conditions may be adjusted, for example depending on the binding affinity of the histone modification binding domains and/or the technical approach used. In particular, the salt concentration of the solution in which the artificial protein is contacted with the sample and/or the salt concentration of the washing solutions used for removing unbound nucleosomes before isolating the complex may be adjusted. This also allows adapting the complex-forming conditions to a desired degree of stringency.

In a preferred embodiment, the complex is immobilized on a solid support such as beads. In this case, the complex can be isolated by a simple pull-down assay well known in the art. Immobilization of the complex is preferably mediated by the affinity tag of the artificial protein.

In a preferred embodiment, the sample is obtained from a patient suffering from a disease. The disease is preferably an autoimmune disease, a developmental disorder, a disease of the nervous system or cancer. Histone modifications are believed to play a role in various human diseases. Thus the analysis of the presence of the first and the second histone modification on nucleosomes from a respective patient is of particular interest.

In a preferred embodiment, the method further comprises the steps of (d) providing a first control protein and a second control protein, each control protein comprising a single histone modification binding domain, wherein the single histone modification binding domain of the first control protein is the same as the first histone modification binding domain of the artificial protein and the single histone modification binding domain of the second control protein is the same as the second histone modification binding domain of the artificial protein; and (e) contacting the first and the second control protein with a sample comprising nucleosomes to allow formation of a complex of the first control protein and a nucleosome having the first histone modification and/or formation of a complex of the second control protein and a nucleosome having the second histone modification; and (f) isolating the complex.

In a preferred embodiment, steps (d) to (f) are performed side-by-side with steps (a) to (c). The control proteins allow verifying the binding specificity of the artificial protein to double-modified nucleosomes by comparing the complex isolated in step (f) with the complex isolated in step (c). In this way, the specific binding of the artificial protein to nucleosomes having both the first and the second histone modification compared to nucleosomes having only one of two histone modifications can be confirmed.

The control proteins may also be used to verify that the artificial protein allows simultaneous entry of the first and the second histone modification from the same nucleosome in the respective histone modification binding pockets of the first and the second histone modification binding domain.

In a preferred embodiment, the method further comprises the step of (g) analysing the isolated complex.

In a preferred embodiment, the isolated complex is analysed by mass spectrometry. Mass spectrometry can be used to confirm the presence of the first and the second histone modification. More importantly, mass spectrometry can be used to identify further histone modifications which co-occur with the first and the second histone modification on the same nucleosome. It also facilitates the identification of proteins which are associated with nucleosomes having the first and the second histone modification. Taken together, information about the typical composition of chromatin comprising the double-modified nucleosomes may be obtained by mass spectrometry of the isolated complex.

In a preferred embodiment, the isolated complex is analysed by recovering DNA from the nucleosome and analysing the DNA. DNA can be easily recovered from the nucleosome by any method suitable for DNA purification from chromatin. DNA recovery is not affected by the additional presence of the artificial protein in the isolated complex.

The isolated complex can also be analysed by both mass spectrometry and DNA analysis of DNA recovered from the nucleosome of the isolated complex.

It is further preferred that the DNA is analysed by quantitative PCR and/or next-generation sequencing.

Quantitative PCR (polymerase chain reaction) can be used to determine the amount of recovered DNA. The amount of recovered DNA is a measure for the amount of nucleosomes that have been isolated, i.e. for the amount of nucleosomes having the first and the second histone modification in the sample.

In next-generation sequencing, the total number of times a DNA fragment is read during the sequencing process allows to determine the enrichment of a corresponding DNA region by the method according to the invention. The sequenced DNA can be mapped and used to study the co-occurrence of histone modifications on a genome-wide or a locus-specific scale.

Further described is the use of an artificial protein for determining whether a first and a second histone modification co-occur on the same copy of a histone protein or on different copies of the same histone protein in a nucleosome, wherein the artificial protein comprises a first histone modification binding domain of 50 to 200 amino acids binding to the first histone modification, a second histone modification binding domain of 50 to 200 amino acids binding to the second histone modification, wherein the first and the second histone modification binding domain are different from each other, a linker of 5 to 50 amino acids connecting the first and the second histone modification binding domain, and an affinity tag.

Modifications occurring at different amino acid residues in a given histone protein such as H3K9me3 and H3K36me3 (both located on histone H3) may co-occur either on the same copy of the histone protein, i.e. on one single histone protein (in cis) or on different copies of the same histone protein (in trans) in the histone protein octamer. Using a heterodimeric artificial protein, i.e. an artificial protein in which the first and the second histone modification binding domain are different from each other, the positioning of the first and the second histone modification in cis or in trans can be determined. To do so, the artificial protein is constructed in a way that allows specific binding of the two histone modifications in cis or in trans only. This can be achieved by adjusting the spatial orientation of the two histone modification binding domains and/or the characteristics of the linker. For example, the histone modification binding domains can be oriented in a manner in which their binding pockets are facing towards the same side of the artificial protein. If this orientation is combined with a rather rigid linker, the artificial protein will specifically bind to histone modifications co-occurring in cis. The rigid linker ensures that the spatial orientation of the two histone modification binding domains is maintained. The histone modification binding domains may also be oriented in a manner in which their binding pockets are facing towards opposite sides of the artificial protein. When combined with a rather rigid linker, this artificial protein will specifically bind to histone modifications co-occurring in trans. Simultaneous entry of two histone modifications into their respective binding pockets will not be feasible when the histone modifications are located in cis but the two binding pockets are facing towards opposite sides of the artificial protein. Therefore, only histone modifications co-occurring in trans will be bound. Thus, the artificial protein presents a useful tool for determining whether the first and the second histone modification co-occur in cis or in trans.

Further described is the use of a homodimeric artificial protein for isolating a symmetrically modified nucleosome. In a homodimeric artificial protein, the first and the second histone modification binding domain are copies of the same domain.

A given histone modification may occur on one copy of the histone protein or on both copies of the histone protein in the histone protein octamer. The term "symmetrically modified nucleosome" refers to a nucleosome in which both copies of the respective histone protein in the histone protein octamer have a given histone modification. The term "asymmetrically modified nucleosome" refers to a nucleosome in which only one of the two different copies of the respective histone protein in the histone protein octamer has a given histone modification. Using a homodimeric artificial protein, symmetrically modified nucleosomes will be isolated due to increased avidity of the artificial protein to the first and the second histone modification. In contrast, when the corresponding single domain is used, both symmetrically and asymmetrically modified nucleosomes will be isolated. By comparing the profiles of the nucleosomes isolated with the homodimeric artificial protein and its single domain counterpart, the distribution of symmetrically and asymmetrically modified mononucleosomes can be studied on a genome-wide or locus-specific scale. Thus, the artificial protein presents a useful tool for determining the distribution of symmetrically and asymmetrically modified nucleosomes. This is of particular importance since to date there is no alternative strategy for a locus-specific analysis of the presence of symmetrically and asymmetrically modified nucleosomes.

Further aspects of the invention will be apparent to the person skilled in the art by the enclosed description of the examples, in particular the scientific results.

EXAMPLES

Materials and Methods
Cloning, Site-Directed Mutagenesis, Expression and Purification The sequences encoding the chromodomain of MPP8 (also known as MPHOSPH8) (57-111 of NP_059990.2), the PWWP domain of DNMT3A (279-420 of NP_001258682) and other, with or without an artificial linker of 27 amino acids were subcloned from in house plasmids and cloned by overlap assembly of DNA fragments fusion into pGEX-6P-2 vector (GE Healthcare, Solingen, Germany) using ligase or ligase-independent methods. In brief, each neighboring fragment to be cloned shared an overlapping region. The overlapping regions were hybridized and extended by normal PCR steps to form a linear sequence. Once nucleic acids encoding the artificial proteins of interest were generated, they were digested with specific restriction enzymes (EcoRI and XmaI) and ligated with digested empty pGEX-6P-2 vector to obtain the final plasmids. The correct sizes of the inserts were confirmed by colony PCR and the correct sequences by Sanger DNA sequencing.

Artificial proteins comprising an N-terminal GST-tag as affinity tag were overexpressed in *E. coli* BL21 cells carrying the corresponding plasmids at 18° C. and purified essentially as described in Rathert et al. 2008, electrophoresed on 12% SDS-PAGE and stained with colloidal Coomassie Brilliant Blue G-250.

In case the first histone modification binding domain is the PWWP domain of Dnmt3a, the sequence selected for cloning also comprises a portion located at the C-terminus of the PWWP domain that is part of the naturally occurring flexible linker that connects the PWWP domain and the ADD domain in the Dnmt3a protein. This is derived from the crystal structure of the PWWP domain. Thus, in artificial proteins in which the first histone modification binding domain is the PWWP domain of Dnmt3a, such as PM, the linker is formed by the C-terminal portion of the PWWP domain. This linker has the following amino acid sequence:

```
                              (SEQ ID NO.: 1)
GGFQPSGPKGLEPPLERPHRD;
or
                              (SEQ ID NO.: 2)
GGFQPSGPKGLEPP
```

The artificial linker is also flexible and has the following amino acid sequence:

```
                              (SEQ ID NO.: 3)
SSGNSNANSRGPSFSSGLVPLSLRGSH
```

Site-directed mutagenesis was used to insert a defined mutation in the binding pocket of the relevant histone modification binding domain in order to generate a domain unable to bind its respective histone modification. Mutated histone modification binding domains served as controls. In the mutated chromodomain of MPP8 (designated M*), the mutation is an F59A exchange that renders the domain unable to bind to H3K9me3. In the mutated PWWP domain of Dnmt3a (designated P*), the mutation is a D329A exchange that renders the domain unable to bind to H3K36me3.

Mutations were introduced using the megaprimer method described in Jeltsch and Lanio 2002 and successful mutagenesis was confirmed by restriction analysis and Sanger DNA sequencing.

Binding of Histone Modification Binding Domains on CelluSpots Histone Peptide Arrays and Far-Western Blotting Experiments to determine the binding specificity of the artificial proteins were performed using the CelluSpots peptide array platform as described in Bock et al. 2011a and Bock et al. 2011b.

For western blot, the peptide array protocol was adapted. Native histones were isolated by acid extraction from HEK293 cells and recombinant histones H3 and H4 were purchased from New England Biolabs (New England Biolabs, Frankfurt a.M., Germany) or purified from *E. coli*. Five micrograms of native histones and 2.5 µg of recombinant histones were loaded and electrophoresed on 16% SDS-PAGE and transferred on nitrocellulose membranes by semi-dry western blotting with transfer buffer (300 mM Tris, 300 mM glycine, pH 9.2) for 10-15 minutes. The membrane was stained with Ponceau S for around 15 minutes to assess the quality of the transfer. Afterwards the membrane was incubated overnight with 5% skim milk at 4° C. The next day the membrane was washed two times with TTBS and once with interaction buffer (100 mM KCl, 20 mM HEPES pH 7.5, 1 mM EDTA, 0.1 mM DTT and 10% glycerol). The membrane was incubated with artificial protein or the respective single histone modification binding domains in interaction buffer for 2 hours at room temperature, washed three times with TTBS and incubated with anti-GST antibody for 1 hour. After three washings with TTBS the membrane was incubated with horseradish peroxidase conjugated with anti-goat antibody for 1 hour at room temperature. After three times washing with TBS, the membrane was immersed in ECL solution and chemiluminescence was detected.

The amounts of artificial proteins (wild type and single domain mutants) used in CelluSpots and western blot analyses were equimolar (10 nM).

H3-GST Tagged Methyl Lysine Analogs and Pull-Downs

The first 60 amino acids of human histone H3 were cloned with C-terminal GST tag with Gibson assembly into pGEX-6p-2 vector where all cysteines belonging to GST were replaced with serine. Afterwards, the targeted lysine residues belonging to histone H3 were replaced with cysteine and alkylated with (2-bromoethyl) trimethylammonium bromide to the respective trimethyl analog as described in Simon et al., 2007. The efficiency of conversion was verified by MALDI-TOF mass spectrometry.

For pull-downs, 25 µg of modified H3-GST was incubated with 0.5 µM of MBP-tagged PM overnight in DP buffer (16.7 mM Tris-Cl, 167 mM NaCl, 1.1% Triton X-100, 1.2 mM EDTA and protease inhibitors) at 4° C. with rotation. Next, the bound complexes were immobilized with 20-40 µl glutathione sepharose 4B beads (GE Healthcare, Solingen, Germany) for 2 hours at 4° C. with rotation, washed with 1× low salt buffer (20 mM Tris-Cl, 150 mM NaCl, 1% Triton X-100, 0.1% SDS and 2 mM EDTA), 1× high salt buffer (20 mM Tris-Cl, 500 mM NaCl, 1% Triton X-100, 0.1% SDS and 2 mM EDTA), 1× LiCl buffer (10 mM Tris-Cl, 250 mM LiCl, 1% NP-40, 1% DOC and 1 mM EDTA) and 2×TE buffer (10 mM Tris-CI pH 8.0 and 1 mM EDTA), with 5 min rotation and centrifugation for 2 min at 4° C. at 2000 rcf after each washing step. The precipitated histones were eluted with LAP (160 mM Tris-Cl pH 6.8, 2% (w/v) SDS, 5% mercaptoethanol, 40% glycerin and 0.1% bromophenol blue), electrophoresed on 18% SDS-PAGE, transferred on a nitrocellulose membrane and probed with anti-H3 antibody (ab1791, Abcam, Cambridge, UK).

Isolation of Nucleosomes by Native Chromatin Interacting Domain Precipitation (nCIDOP) Coupled with Quantitative PCR and Next-Generation Sequencing Native chromatin comprising nucleosomes were isolated from around 20 million HepG2 cells (which was sufficient for 5-15 CIDOP/ChIP experiments) by micrococcal nuclease digestion of nuclei as described in Brand et al. 2008 with minor modifications. In brief, following MNase digestion, the nuclei were centrifuged at 13000 g for 10 minutes and the resulting supernatant which contained the soluble nucleosomal fraction was collected and snap frozen. Then, a sample of native chromatin (10-30 μg based on DNA absorbance) was pre-cleared for 1 hour at 4° C. with 20 μl glutathione sepharose 4B beads (GE Healthcare, Solingen, Germany) in DP buffer (16.7 mM Tris-CI, 167 mM NaCl, 1.1% Triton X-100, 1.2 mM EDTA and protease inhibitors) filled up to 500 μl. The beads were removed and the supernatant (pre-cleared chromatin) was incubated overnight with the artificial protein (10-30 μg or equimolar concentration when compared to single domains with different size) at 4° C. The next day, the artificial protein-nucleosome complexes were immobilized for 2 hours on 20 μl glutathione sepharose 4B beads (GE Healthcare, Solingen, Germany) with rotation at 4° C. and washed for 10 minutes with rotation under stringent conditions with: 1× Low Salt Buffer (20 mM Tris-CI pH 8.0, 150 mM NaCl, 1% Triton X-100, 0.1% SDS and 2 mM EDTA), 1× High Salt Buffer (20 mM Tris-CI pH 8.0, 500 mM NaCl, 1% Triton X-100, 0.1% SDS and 2 mM EDTA), 1× LiCl buffer (10 mM Tris-CI pH 8.0, 250 mM LiCl, 1% NP-40, 1% sodium deoxycholate and 1 mM EDTA) and 2×TE buffer (10 mM Tris-CI pH 8.0 and 1 mM EDTA). In case of less stringent conditions, washing was performed with: 3×PB buffer (50 mM Tris-CI, 200 mM NaCl, 1 mM EDTA, 0.5% NP-40 and 2 mM DTT) and 2×TE buffer. Between each washing step, the complexes were spun down for 2 min at 2000 g at 4° C. Bound nucleosomes were eluted in 200 μl elution buffer (50 mM Tris-CI, 50 mM NaCl, 1 mM EDTA and 1% SDS) and 1 μl proteinase K (20 mg/ml) for 45 minutes at room temperature with rotation. After incubation and centrifugation for 3 minutes at 3000 g the supernatant was transferred into a new tube and incubated for 1 hour at 55° C. with additional 1 μl proteinase K. The DNA was recovered from the nucleosomes using Chromatin IP DNA purification columns (Active Motif, La Hulpe, Belgium).

The recovered DNA was quantified by real-time PCR. The quantitative PCR assays were performed on a CFX96 Touch or CFX96 Real-Time detection system (Bio-Rad, Munich, Germany) using SYBR fast qPCR mix (Kapa Biosystems, London, UK) or SsoFast EvaGreen supermix (Bio-Rad, Munich, Germany). The PCR protocol used was: 3 minutes at 95° C., 39 cycles of 95° C. for 3 seconds, followed by 20 seconds at 58-60° C. and 72° C. for 3 seconds. The primers used are listed in Table 2. A standard curve was generated to calculate the percent of precipitated DNA and test the efficiency of each primer set.

TABLE 2

Primers used in quantitative PCR assays

| Genome region | Associated histone modifications | Sequence of forward primer | Sequence of reverse primer | Size of PCR product (bp) |
| --- | --- | --- | --- | --- |
| PM-PM1 chr2 | H3K36me3 and H3K9me3 | GTCTTAACCGTCTGCCTAGA (SEQ ID NO.: 4) | TGGTAGATTGGCAAATGGAA (SEQ ID NO.: 5) | 127 |
| PM-PM2 chr12 | H3K36me3 and H3K9me3 | GCCTCTGCATTCAGCATTTC (SEQ ID NO.: 6) | AGGTTGGCCAAAGACACATC (SEQ ID NO.: 7) | 124 |
| PM-PM3 chr7 | H3K36me3 and H3K9me3 | CCAGACCAGTGCAATAAGGAA (SEQ ID NO.: 8) | TGACCTTTGAGGGTTCAAG (SEQ ID NO.: 9) | 132 |
| PM-PM5 chr5 | H3K36me3 and H3K9me3 | CTGCTCCCATGTCTGCTACA (SEQ ID NO.: 10) | TGGAAGGACTGCAGAGAAAA (SEQ ID NO.: 11) | 119 |
| PM-P1 chr12 | H3K36me3 | CAATGACCCCTTCATTGACC (SEQ ID NO.: 12) | GGGGGAATACGTGAGGGTAT (SEQ ID NO.: 13) | 119 |
| PM-P3 chr1 | H3K36me3 | TGCAAAGAAAAGGAGCAGAA (SEQ ID NO.: 14) | CCAACAAGCAAAAGAAGGAAA (SEQ ID NO.: 15) | 90 |
| PM-P5 chr9 | H3K36me3 | TGCTCCTTTTTCCCATCTTTT (SEQ ID NO.: 16) | GCAAAACCAAGTCGAATGCT (SEQ ID NO.: 17) | 99 |
| PM-M2 chr5 | H3K9me3 | TGCATGATGTTTTCCTCAGC (SEQ ID NO.: 18) | ATCTTGCGCAAATGCTCTG (SEQ ID NO.: 19) | 119 |
| PM-M3 chr19 | H3K9me3 | TTGTCACCACTGTCCAGGAA (SEQ ID NO.: 20) | CAGCTGCCTCAGAGACACAC (SEQ ID NO.: 21) | 123 |
| PM-M4 chr5 | H3K9me3 | AGAACACCATGGACCACCAG (SEQ ID NO.: 22) | TTTCTGAATTGGTTCTGGGTTT (SEQ ID NO.: 23) | 113 |

The genomic regions have the first and the second histone modification (H3K36me3 and H3K9me3, genomic regions designated PM-PM), only the first histone modification (H3K36me3, genomic regions designated PM-P) or only the second histone modification (H3K9me3, genomic regions designated PM-M).

Around 50 million, 100-nucleotide sequence reads obtained with Illumina's HiSeq 2500 were mapped to the human reference genome hg19 with Bowtie (Langmead et al. 2009) from the Chipster software tool (Kallio et al. 2011). Only uniquely mapped reads were retained and all duplicates were removed. The genome coverage files normalized to reads per kilobase per million (RPKM) and the Spearman's rank correlation coefficient in window sizes of 10 kb were calculated with deepTools (Ramirez et al. 2014). The genome browser snapshots were taken with the Integrative Genomics Viewer (IGV).

For definition of no H3K9me3 and H3K36me2/3, H3K9me3-only, H3K36me2/3-only and overlap of H3K36me2/3 and H3K9me3 chromatin states, the genome was divided in 3-kb bins or in 1-kb bins and the number of normalized (to the highest dataset) reads per million (RPM) was quantified using the SeqMonk software. After subtraction of background signal, the four chromatin states were defined by using the IF condition in Microsoft Excel and then the overlap of the signal obtained with PM with all four states was calculated.

Analysis of H3K9Me3-H3K36Me2/3 Bivalent State

The distribution of genes per chromosome, peaks and overlap with chromatin segments was determined with Epi-Explorer (Halachev et al., 2012) and seqMINER was used for k-means clustering and heatmap generation (Ye et al. 2011). The Spearman correlation of raw data in 10-kb bins and the metagene profiles were generated in DeepTools (Ramirez et al. 2014). The GO analysis of clusters obtained by k-means clustering was carried out in ChIP-Enrich (Welch et al. 2014). For GO analyses, the first 10-15 categories termed "biological process" were selected.

The ChIP-seq datasets of H3K4me1, ZNF274, SetDB1 and KAP1 were downloaded from ENCODE (ENCODE-consortium 2012) and further mapped to Hg38 following the inventors' ChIP-seq bioinformatics pipeline. The ZNF274, SetDB1 and Trim28 peaks were directly downloaded from ENCODE and lift-Overed to Hg38 (Kent et al. 2002).

For RNA-seq, available datasets from HepG2 cells (ENCODE-consortium 2012) produced by Caltech were used. The reads were mapped with TopHat from the Tuxedo Suite package (Trapnell et al. 2012) using default settings. The transcript assembly from both replicates was carried out in the RNA pipeline in SeqMonk and the transcript list from both replicates was merged. All transcripts were ranked based on FPKM (fragments per kilobase of exon per million fragments mapped) and segregated in four groups based on their frequency distribution: no expression, low expression-1, low expression-2, medium expression, high expression.

Results

Production and Characterization of Artificial Proteins

Artificial proteins produced are listed in Table 3. For example, PM is an artificial protein comprising the PWWP domain of Dnmt3a binding to H3K36me3, the chromodomain of MPP8 binding to H3K9me3, a linker connecting the PWWP domain and the chromodomain, and a GST tag.

Variants of the artificial protein PM with pocket mutations in the first or the second histone modification binding domain were also produced and are listed in Table 4. The mutated domain is indicated by a "*". The mutated variants were used as controls since the mutation inactivated binding of the domain to its respective histone modification.

Each artificial protein produced comprises an N-terminal GST tag as affinity tag.

The naturally occurring linker is derived from the linker connecting the PWWP domain and the ADD domain in the Dnmt3a protein. In some proteins such as PM this linker has 21 amino acids (SEQ ID NO.: 1). In some proteins such as PT it has 14 amino acids (SEQ ID NO.: 2).

TABLE 3

Artificial proteins

| Name | First histone modification binding domain | First histone modification | Linker (number of amino acids) | Second histone modification binding domain | Second histone modification | DNA sequence encoding the artificial protein | Amino acid sequence of artificial protein |
|---|---|---|---|---|---|---|---|
| PM | PWWP domain of Dnmt3a | H3K36me3 | Naturally occurring linker (21) | chromodomain of MPP8 | H3K9me3 | SEQ ID NO.: 24 | SEQ ID NO.: 25 |
| C7LT | chromodomain of CBX7 | H3K27me3 | Artificial linker (27) | PHD domain of TAF3 | H3K4me3 | SEQ ID NO.: 26 | SEQ ID NO.: 27 |
| PT | PWWP domain of Dnmt3a | H3K36me3 | Naturally occurring linker (14) | PHD domain of TAF3 | H3K4me3 | SEQ ID NO.: 28 | SEQ ID NO.: 29 |
| MLM | chromodomain of MPP8 | H3K9me3 | Artificial linker (27) | chromodomain of MPP8 | H3K9me3 | SEQ ID NO.: 30 | SEQ ID NO.: 31 |
| MLP | chromodomain of MPP8 | H3K9me3 | Artificial linker (27) | PWWP domain of Dnmt3a | H3K36me3 | SEQ ID NO.: 32 | SEQ ID NO.: 33 |
| PLM | PWWP domain of Dnmt3a | H3K36me3 | Artificial linker (27) | chromodomain of MPP8 | H3K9me3 | SEQ ID NO.: 34 | SEQ ID NO.: 35 |
| PLP | PWWP domain of Dnmt3a | H3K36me3 | Artificial linker (27) | PWWP domain of Dnmt3a | H3K36me3 | SEQ ID NO.: 36 | SEQ ID NO.: 37 |
| PP | PWWP domain of Dnmt3a | H3K36me3 | Naturally occurring linker (21) | PWWP domain of Dnmt3a | H3K36me3 | SEQ ID NO.: 38 | SEQ ID NO.: 39 |
| MLdT | chromodomain of MPP8 | H3K9me3 | Artificial linker (27) | double Tudor domain of JMJD2A | H4K20me3 | SEQ ID NO.: 40 | SEQ ID NO.: 41 |

TABLE 3-continued

Artificial proteins

| Name | First histone modification binding domain | First histone modification | Linker (number of amino acids) | Second histone modification binding domain | Second histone modification | DNA sequence encoding the artificial protein | Amino acid sequence of artificial protein |
|---|---|---|---|---|---|---|---|
| dTLM | double Tudor domain of JMJD2A | H4K20me3 | Artificial linker (27) | chromodomain of MPP8 | H3K9me3 | SEQ ID NO.: 42 | SEQ ID NO.: 43 |
| PC7 | PWWP domain of Dnmt3a | H3K36me3 | Naturally occurring linker (14) | chromodomain of CBX7 | H3K27me3 | SEQ ID NO.: 44 | SEQ ID NO.: 45 |
| C7LP | chromodomain of CBX7 | H3K27me3 | Artificial linker (27) | PWWP domain of Dnmt3a | H3K36me3 | SEQ ID NO.: 46 | SEQ ID NO.: 47 |
| C7LM | chromodomain of CBX7 | H3K27me3 | Artificial linker (27) | chromodomain of MPP8 | H3K9me3 | SEQ ID NO.: 48 | SEQ ID NO.: 49 |
| MLC7 | chromodomain of MPP8 | H3K9me3 | Artificial linker (27) | chromodomain of CBX7 | H3K27me3 | SEQ ID NO.: 50 | SEQ ID NO.: 51 |
| TLC7 | PHD domain of TAF3 | H3K4me3 | Artificial linker (27) | chromodomain of CBX7 | H3K27me3 | SEQ ID NO.: 52 | SEQ ID NO.: 53 |
| PA | PWWP domain of Dnmt3a | H3K36me3 | Naturally occurring linker (14) | ADD domain of ATRX | H3K9me3 when H3K4 unmodified | SEQ ID NO.: 54 | SEQ ID NO.: 55 |
| PLA | PWWP domain of Dnmt3a | H3K36me3 | Artificial linker (27) | ADD domain of ATRX | H3K9me3 when H3K4 unmodified | SEQ ID NO.: 56 | SEQ ID NO.: 57 |
| ALP | ADD domain of ATRX | H3K9me3 when H3K4 unmodified | Artificial linker (27) | PWWP domain of Dnmt3a | H3K36me3 | SEQ ID NO.: 58 | SEQ ID NO.: 59 |
| TLP | PHD domain of TAF3 | H3K4me3 | Artificial linker (27) | PWWP domain of Dnmt3a | H3K36me3 | SEQ ID NO.: 60 | SEQ ID NO.: 61 |
| PLT | PWWP domain of Dnmt3a | H3K36me3 | Artificial linker (27) | PHD domain of TAF3 | H3K4me3 | SEQ ID NO.: 62 | SEQ ID NO.: 63 |
| PLC7 | PWWP domain of Dnmt3a | H3K36me3 | Artificial linker (27) | chromodomain of CBX7 | H3K27me3 | SEQ ID NO.: 64 | SEQ ID NO.: 65 |

TABLE 4

Variants of PM with pocket mutations

| Name | First histone modification binding domain | First histone modification | Linker (number of amino acids) | Second histone modification binding domain | Second histone modification |
|---|---|---|---|---|---|
| P*M | Mutated PWWP domain of Dnmt3a (D329A) | — | Naturally occurring linker (21) | chromodomain of MPP8 | H3K9me3 |
| PM* | PWWP domain of Dnmt3a | H3K36me3 | Naturally occurring linker (21) | Mutated chromodomain of MPP8 (F59A) | — |

The proteins from which the histone modification binding domains have been derived have the following protein identifiers in Universal Protein Resource (UniProt) databases (amino acids in the protein sequence that correspond to the respective histone modification binding domain are also indicated):
Dnmt3a Q9Y6K1 (PWWP domain: amino acids 292-350);
MMP8 Q99549 (chromodomain: amino acids 59-118);
CBX7 O95931 (chromodomain: amino acids 11-69);
TAF3 Q5VWG9 (PHD domain: amino acids 865-915);
JMJD2A O75164 (double Tudor domain: amino acids 897-1011); and
ATRX P46100 (ADD domain: amino acids 159-296).

FIG. 1 shows an SDS-PAGE of purified artificial proteins and variants of PM stained with Coomassie Brilliant Blue.

The binding specificity of the artificial proteins and variants with a pocket mutation in the first or the second histone modification binding domain to the first and/or the second histone modification was confirmed by peptide arrays. It was confirmed that PM harbors the binding specificity of P (binding to H3K36me2/3) and M (binding to H3K9me2/3 and H3K27me3, however, binding to H3K27me3 is only observed in vitro). As expected, P*M retained binding to H3K9me2/3 and H3K27me3 and exhibited loss of binding to H3K36me3. Likewise, PM* showed binding to H3K36me2/3 only. This is in agreement with the binding profiles of the non-mutated corresponding single domains.

It was further confirmed that C7LT harbors the specificity of C7 (binding to H3K9me3 and H3K27me3, however, binding to H3K9me3 is only observed in vitro) and T (binding to H3K4me3), while PT harbors the specificity of P (binding to H3K36me2/3) and T (binding to H3K4me3). Binding specificity of MLM to H3K9me3 and H3K27me3 was also confirmed, however, binding to H3K27me3 is only observed in vitro.

Binding specificity of PLP to H3K36me2/3 was also confirmed. It was found that in peptide arrays, PLP binds stronger to H3K36me2/3-modified peptides than its single domain counterpart P.

Binding of the Artificial Protein to Modified Histone Proteins

Figure 2:
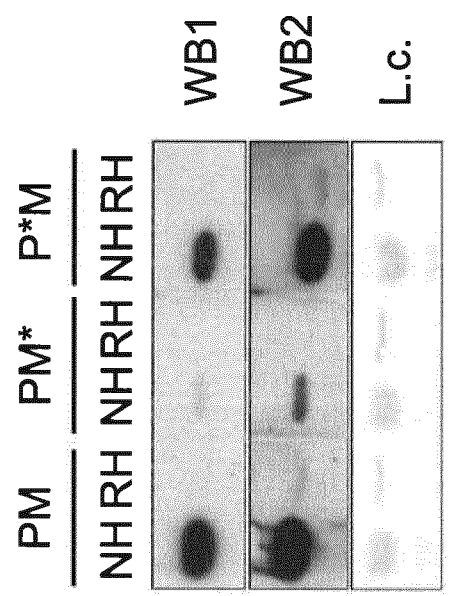
FIG. 2 shows far-western blot analyses of the binding of the artificial protein PM in which the first histone modification binding domain is the PWWP domain of Dnmt3a (P) and the second histone modification binding domain is the chromodomain of MPP8 (M) to native and recombinant histone proteins (NH, native histone proteins; RH, recombinant histone proteins; L.c., loading control). Analysis of variants of PM having a pocket mutation either in the first histone modification binding domain (P*M) or in the second histone modification binding domain (PM*) are also shown.

FIG. 2 shows two far-western blot analyses (designated WB1 and WB2) using the artificial protein PM and its respective variants with a pocket mutation in the first (P*M) or the second (PM*) histone modification binding domain. Binding to native histone proteins (NH) and to recombinant histone proteins (RH) was tested. L.c. designates the loading control (Ponceau S staining). In contrast to native histones, recombinant histones do not have any post-translational modifications. Accordingly, none of PM, P*M and PM* bound to recombinant histones. As expected, binding to native histones was observed. Binding of PM is strongest, indicating enhanced binding of PM to histone modifications compared to its variants P*M and PM*. This is likely due to multi-dentate binding of the two (non-mutated) binding domains in PM to their target histone modifications, which in turn leads to an increased avidity of PM to its target histone modifications. Binding of PM* is weakest due to the weak binding of P to its respective histone modification.

Using the same assay, binding to native histones but not to recombinant histones was also found for C7LT, PT, MLM and PLP. Of interest, MLM bound to histones having its target modifications with much stronger affinity compared to the single domain counterpart M. Likewise, PLP bound to histones having its target modifications with much stronger affinity compared to the single domain counterpart P.

Figure 3:
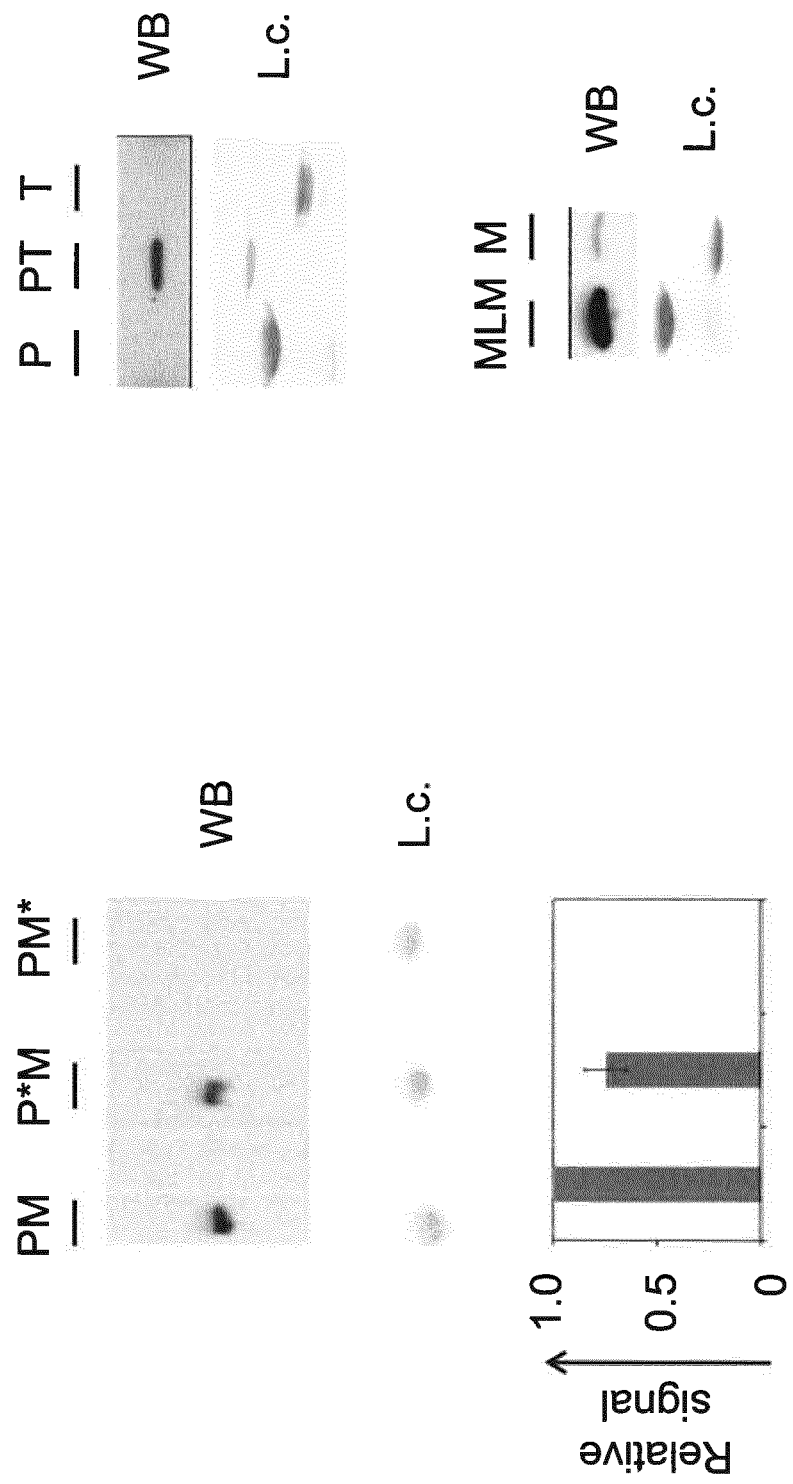
FIG. 3 shows western blot analysis of nucleosomes isolated using (i) the artificial protein PM or one of its variants having a pocket mutation; (ii) PT or its single domain counterparts P and T; (iii) MLM or its single domain counterpart M. isolated nucleosomes were detected with anti-histone H3 antibody (L.c., loading control).

Isolation of Nucleosomes by Native Chromatin Interacting Domain Precipitation (nCIDOP) and Analysis of Recovered DNA Mononucleosomes prepared from human cells were isolated by chromatin interacting domain precipitation (CIDOP) using PM, P*M and PM*. Washing was performed under stringent conditions. Precipitated mononucleosomes were detected by western blot (WB) with anti-histone H3 antibody as shown in FIG. 3. L.c. designates the loading control (Ponceau S staining). The bar diagram shows a quantification of the data based on two repetitions. Error bars represent the standard error of mean (SEM). The results show that PM was more efficient in nucleosome precipitation than its variants P*M and PM*. The results further indicate that, under stringent washing conditions, a higher amount of nucleosomes can be retained by PM due to bivalent binding to mononucleosomes in comparison to P*M and PM*, which exhibit only monovalent interactions, similarly as observed in the far-western blot analysis. These results are particularly striking since the amount of H3K9me3-H3K36me2/3 double modified mononucleosomes in the input by definition must be smaller than the total amount of mononucleosomes carrying H3K9me3 regardless of the modification state of H3K36.

Using the same assay, mononucleosomes were isolated using PT, P and T or using MLM and M and detected by western blot (WB) with anti-histone H3 antibody (FIG. 3). The results show that PT was able to precipitate mononucleosomes under conditions in which the single domain counterparts P and T did not. The results further show that MLM was more efficient in nucleosome precipitation than its single domain counterpart M. The results indicate that a higher amount of nucleosomes can be retained by PT and MLM due to bivalent binding to mononucleosomes in comparison to their respective single domain counterparts, which exhibit only monovalent interactions.

For DNA analysis, nucleosomes comprising the first and/or the second histone modification were isolated by CIDOP using PM, P*M and PM* as well as the single histone modification binding domains P (PWWP domain of Dnmt3a) and M (chromodomain of MPP8). Washing was performed under stringent conditions except for P and PM* which were washed under less stringent conditions due to the weak binding affinity of P to its target histone modification compared to M.

DNA was recovered from the isolated complexes and analysed by quantitative PCR using amplicons associated with both H3K9me3 and H3K36me3 modifications (based on H3K9me3 and H3K36me3 peak overlap) ("K9me3+K36me3") and amplicons associated with H3K9me3 only ("K9me3") or H3K36me3 only ("K36me3"). Four genome regions associated with both H3K9me3 and H3K36me3 (PM-PM1 chr2, PM-PM2 chr12, PM-PM3 chr 7 and PM-PM5 chr 5), three regions associated with H3K9me3 only (PM-M2 chr5, PM-M3 chr19 and PM-M4 chr5) and three regions associated with H3K36me3 only (PM-P1 chr12, PM-P3 chr1 and PM-P5 chr9) were tested.

Figure 4:
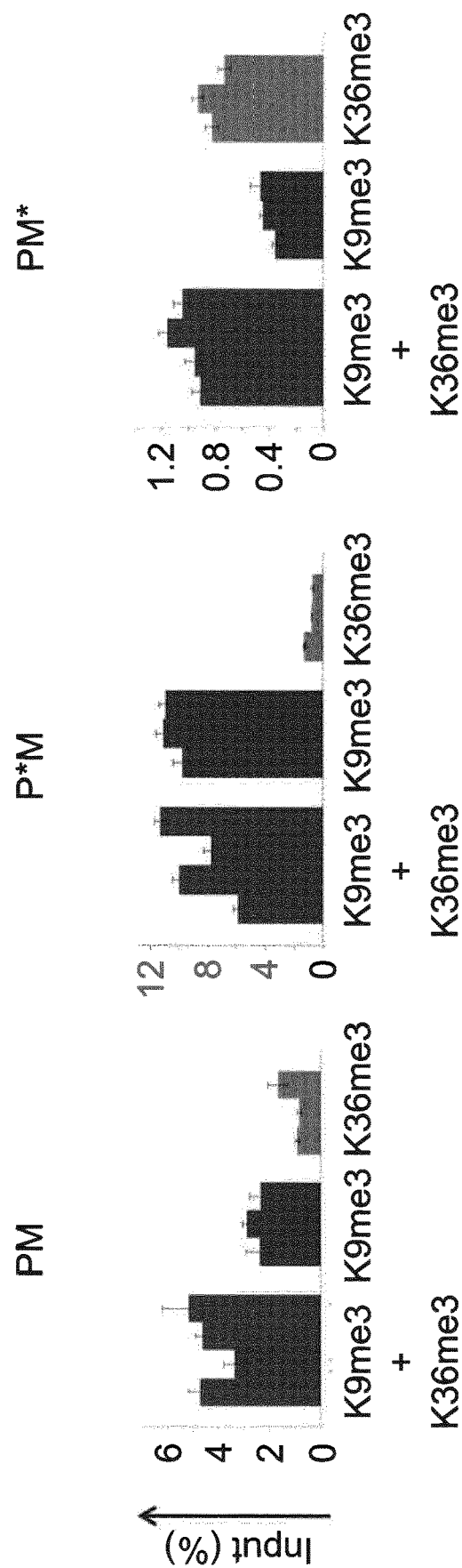
FIG. 4 shows the results of analysing recovered DNA by quantitative PCR. The DNA was recovered from nucleosomes isolated using the artificial protein PM or one of its variants having a pocket mutation.

The results obtained for PM, P*M and PM* are shown in FIG. 4. Error bars represent the standard error of mean (SEM). The results show that artificial proteins are able to interact with native nucleosomes. The results further indicate that PM has a different binding profile than its respective variants P*M and PM*. PM shows preferred binding to nucleosomes comprising both the first and the second histone modification. The variants P*M and PM* bind roughly equally to nucleosomes comprising both histone modifications and to nucleosomes comprising only H3K9me3 in the case of P*M and H3K36me3 in the case of PM*.

The single domains P and M differ in their binding affinities. M has a higher binding affinity to its target histone modification than P on a peptide level. This may explain the differences observed on the chromatin level such as the different values on the y-axis between PM, PM* and P*M.

PM is highly selective for doubly modified nucleosomes which are not as common as singly modified nucleosomes. This might explain the lower value on the y-axis when compared to P*M.

Using the same assay, stronger binding to nucleosomes comprising both the first and the second histone modification compared to nucleosomes having only one of the two histone modifications was also found for C7LT and PT.

Thus, the artificial protein favors binding to nucleosomes when both the first and the second histone modification are present.

Figure 5:
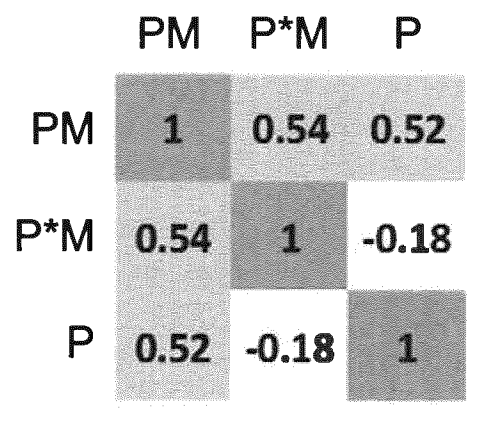

DNA recovered from the isolated nucleosomes was further analysed by next-generation sequencing. FIG. 5 shows the Spearman correlation coefficient which was calculated in bins of 10-kb and indicates that the profile of PM is different from the profile of P*M (M active) and P (which is analogous to PM*).

Figure 6:
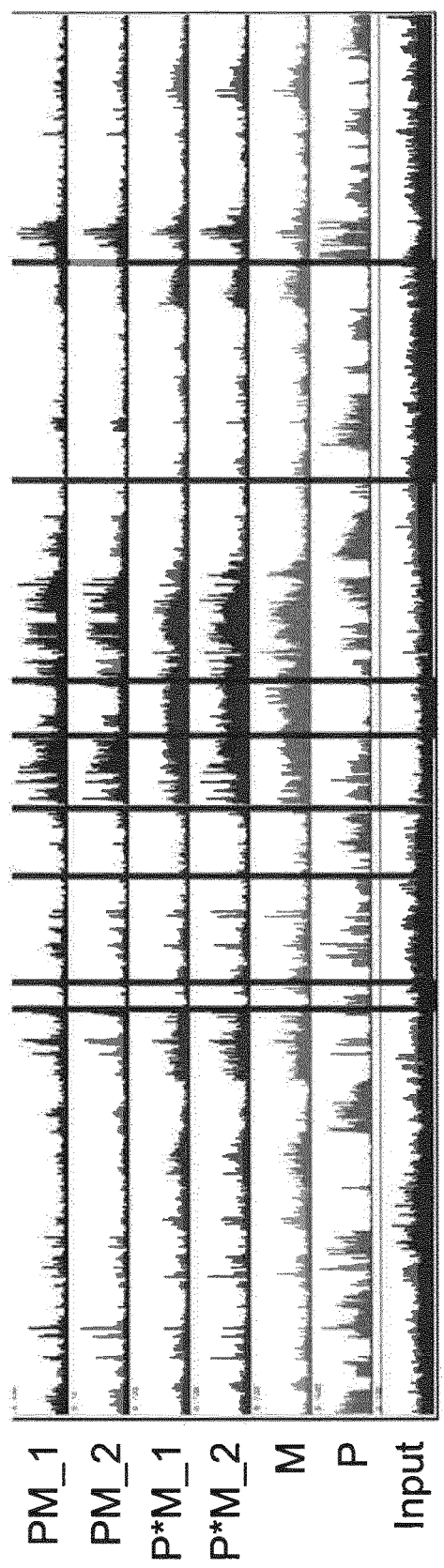
FIG. 6 shows genome browser tracks of sections of chromosome 19 obtained by next-generation sequencing of recovered DNA. The DNA was recovered from nucleosomes isolated using the artificial protein PM, its variant having a pocket mutation in the first histone modification binding domain (P*M), a single chromodomain of MPP8 (M), or a single PWWP domain of Dnmt3a (P).

FIG. 6 shows genome browser tracks of sections of chromosome 19 obtained by next-generation sequencing using PM (in two repeats designated PM_1 and PM_2), P*M (in two repeats designated P*M_1 and P*M_2), M and P. The y-axis indicates the number of reads. The signal obtained with PM is only present when both P*M (and its analogous single domain M) and P (analogous to PM*) overlap, i.e. when the first and the second histone modification co-occur. If only one of the two histone modifications is present, PM only yields a background signal. This can be seen for example in the regions highlighted by the black boxes. Thus, the presence of only one of H3K36me3 and H3K9me3 is not sufficient for binding of PM to the nucleosome.

This indicates that PM is highly selective for nucleosomes having both the first and the second histone modification. It also confirms that the single histone modification binding domains have distinct binding profiles compared to the artificial protein.

Whole Genome Analysis of Nucleosomes Isolated with PM

The inventors further analyzed the next-generation sequencing results obtained from nucleosomes isolated with PM by chromatin interacting domain precipitation at whole genome level. The genome was segmented into pieces of 3000 base pairs, the obtained reads averaged and background subtracted. Analysis of the M and P data allows to annotate regions of the whole genome that contain only H3K9me3 (M signal but not P signal), only H3K36me3 (P signal but no M signal), none of the two histone modifications or both of them. It is thus possible to define the fraction of recovered DNA located in the respective regions.

Figure 7:
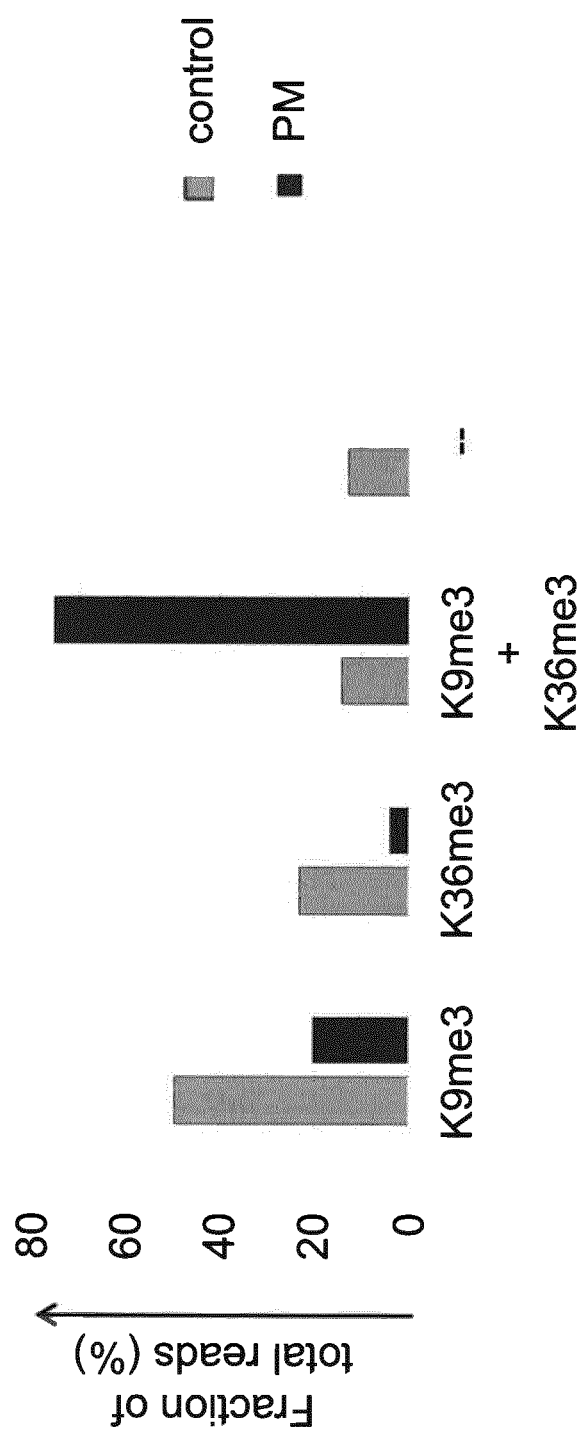
FIG. 7 shows the genomic localization of DNA recovered from nucleosomes isolated using PM compared to DNA recovered from control nucleosomes. DNA was analysed by next-generation sequencing.

In FIG. 7, the genomic localization of DNA recovered from nucleosomes isolated with PM ("PM", black bars) is compared to DNA recovered from control nucleosomes ("control", grey bars). Control nucleosomes were directly subjected to next-generation sequencing, i.e. without any native chromatin interacting domain precipitation. The fraction of total reads in regions that are annotated as H3K9me3-only regions ("K9me3"), H3K36me3-only regions ("K36me3"), regions annotated as having both H3K9me3 and H3K36me3 ("K9me3+K36me3") and regions annotated as having neither H3K9me3 nor H3K36me3 ("--") is shown.

For example, the inventors found that 50% of the genomic fragments identified in next-generation sequencing of DNA recovered from control nucleosomes are located in regions that are annotated as H3K9me3-only regions (first column on the left). Based on DNA recovered from control nucleosomes, the inventors further found that 16.6% of the genome carries both H3K9me3 and H3K36me3. Analysis of DNA recovered from nucleosomes isolated with PM shows that nucleosomes having both H3K9me3 and H3K36me3 are strongly enriched. This demonstrates successful use of PM for isolating nucleosomes comprising the double-modified histone protein octamer having both H3K9me3 and H3K36me3.

For a genome-wide scale, the inventors binned the genome in 3 kb windows and defined four chromatin states based on the distribution of H3K9me3 signals (merged M and P*M data) and H3K36me2/3 signals (P data):
  (i) without H3K9me3 and H3K36me2/3 (153,184 3-kb regions),
  (ii) H3K36me2/3-only (108,714 3-kb regions),
  (iii) H3K9me3-only (427,762 3-kb regions), and
  (iv) overlap of H3K36me2/3 and H3K9me3 (171,127 3-kb regions).

Equivalent results were obtained using 1-kb bins.

Figure 8:
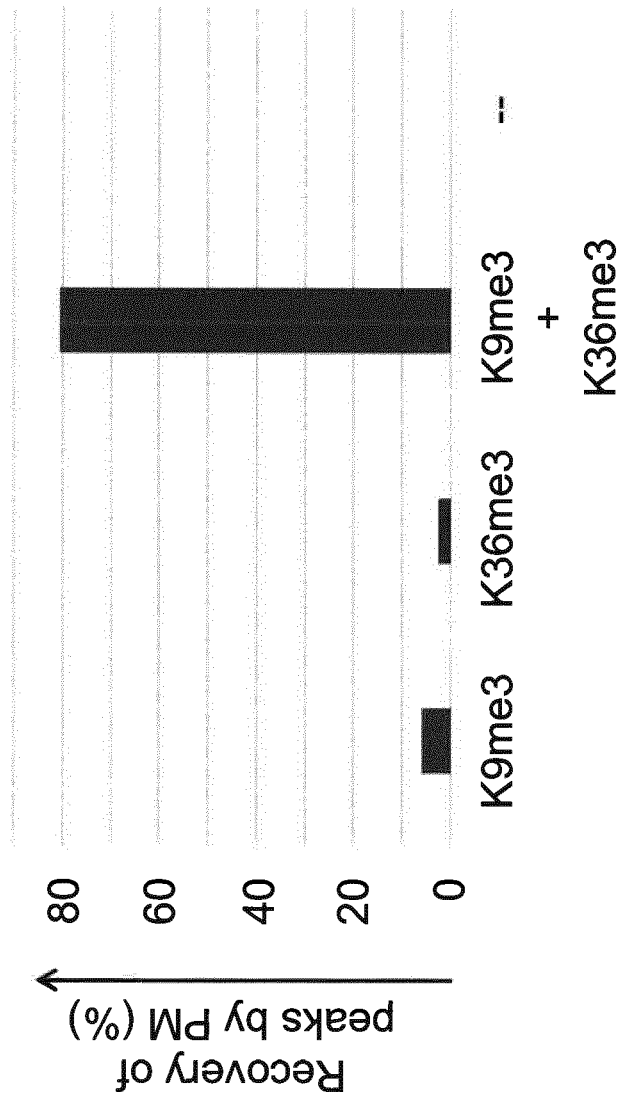
FIG. 8 shows the recovery of peaks obtained with PM based on next-generation sequencing of DNA recovered from nucleosomes isolated using PM.

Recovery of the peaks obtained with PM was also analyzed. Results are shown in FIG. 8. 80.87% of all regions of the genome known to have both H3K9me3 and H3K36me3 modifications ("K9me3+K36me3") were detected by PM. Only 6.2% of the H3K9me3-only regions ("K9me3"), 6.66% of the H3K36me3-only regions ("K36me3") and 0.04% of the regions having neither H3K9me3 nor H3K36me3 ("--") were isolated by PM. Therefore, PM is a powerful tool for the specific readout of nucleosomes comprising the double-modified histone protein octamer at the whole genome level. In the following, the PM signal is referred to as H3K9me3-H3K36me2/3 bivalent state.

Analysis of H3K9Me3-H3K36Me2/3 Bivalent State

The distribution of nucleosomes with bivalent H3K9me3-H3K36me2/3 marks in HepG2 cells was investigated on a genome-wide scale. A non-random distribution would indicate that the bivalent H3K9me3-H3K36me2/3 modification represents a novel chromatin state. To this end, peaks obtained from both CIDOP-sequencing replicates were merged and the EpiExplorer database (Halachev et al. 2012) was used for data mining. By comparing the distribution of H3K9me3-H3K36me2/3 peaks and using the same number of randomized peaks as control, an enrichment of H3K9me3-H3K36me2/3 in distinct chromatin states was observed, all of them defined by weak transcription. Thus, the genome-wide distribution of H3K9me3-H3K36me2/3 is not random. Therefore, the co-occurrence of H3K9me3 and H3K36me2/3 on the same nucleosome represents a novel bivalent chromatin state in human cells which is enriched in weakly transcribed chromatin segments.

Substantial enrichment was observed in the chromatin segment annotated as "weak transcribed" (Ernst et al. 2011). In addition, segments such as "weak enhancer-2" (designated as weak/poised enhancer-7 in Ernst et al. 2011), and "strong enhancers-2" (designated as strong enhancers-5 in Ernst et al. 2011) also showed enrichment of H3K9me3-H3K36me2/3 when compared to "weak enhancer-1" (designated as weak/poised enhancer-6 in Ernst et al. 2011) and strong enhancer-1 (designated as strong enhancer-4 in Ernst et al. 2011).

According to the definitions in Ernst et al., 2011, strong enhancers-1 (SE-1) are defined by low levels of H3K36me3, high levels of H3K4me1, H3K4me2, H3K4me3, H3K27ac, H3K9ac and high DNA accessibility. Strong enhancers-2 (SE-2) are defined by high levels of H3K4me1 and H3K27ac, medium levels of H3K4me2 and no H3K4me3, low levels of H3K36me3 and H3K9ac and a two-fold lower DNA accessibility in comparison to strong enhancers-1. Weak/poised enhancers-1 (WE-1) are defined by medium levels of H3K4me1, high levels of H3K4me2 and almost no H3K36me3, H3K4me3, H3K9ac and H3K27ac, with DNA accessibility similar to strong enhancers-2. Weak/poised enhancers-2 (WE-2) are defined by medium levels of H3K4me1 and almost no H3K36me3, H3K4me2, H3K4me3, H3K9ac and H3K27ac, with DNA accessibility two fold lower than SE-2 or WE-1. Weak transcribed states are defined by little H3K36me3, no H3K4me1/2/3, no H3K27ac, no H3K9ac, low DNA accessibility and weak transcription.

The inventors further plotted the H3K9me3-H3K36me2/3, H3K9me3 and H3K36me2/3 signals over the promoters and bodies of all genes binned by their expression levels and observed a strong preference of the H3K9me3-H3K36me2/3 bivalent state for genes with low expression, while the distribution of signal over highly expressed and unexpressed genes was similar to each other and lower than over lowly expressed genes. This was in contrast to the H3K9me3 signal, which was highly enriched in unexpressed genes, but not in genes with high, medium and low expression, and the H3K36me2/3 signal, which was enriched in expressed genes (correlated with levels of expression), but not in unexpressed genes.

To further dissect the chromatin state of genes with the lowest expression (low expression-2), k-means clustering was performed and it was re-affirmed that these genes are overlaid with H3K9me3-H3K36me2/3, H3K36me2/3 and H3K9me3. The strongest H3K9me3-H3K36me2/3 signal was found in clusters 3, 5, 6, and 7, which encode for gene ontology (GO) categories associated with biological processes such as cell cycle transition, metabolism of nucleotides, morphogenesis and development (especially of bones) and hormone metabolism. Collectively these data indicate that the H3K9me3-H3K36me2/3 state is enriched in genes with low expression levels in HepG2 cells and that these genes might have a role in cell cycle regulation, hormone signalling or morphogenesis genes.

In addition to "weak transcribed" chromatin segments and genes, an enrichment of the H3K9me3-H3K36me2/3 bivalent state was also observed in certain subtypes of enhancers, decorated only with lower methylation states of H3K4, as defined by chromatin segmentation (Ernst et al. 2011). To verify these observations, the inventors selected H3K4me1 ChIP-seq peaks associated with weak/poised enhancers-1 (WE-1), weak/poised enhancers-2 (WE-2), strong enhancers-1 (SE-1) and strong enhancer-2 (SE-2) and plotted their H3K9me3-H3K36me2/3, H3K9me3 and H3K36me3 signals. Stronger enrichment of H3K9me3-H3K36me2/3 in WE-2 and SE-2 in comparison to WE-1 and SE-1, respectively, was detected. The corresponding single marks were enriched as well. To functionally dissect the two subtypes of enhancers, the inventors performed k-means clustering, centered around the midpoints of H3K4me1 peaks associated with WE-2 or SE-2, respectively, and found 5 clusters (out of ten) with very high enrichment of H3K9me3-H3K36me2/3 in WE-2 and 3 clusters (out of ten) in SE-2. Then, the H3K4me1 peaks from each cluster were linked to the closest TSS in a distance of at least 10-kb (to associate enhancers with putative target genes but exclude promoters) and GO analyses was carried out with these genes. The WE-2 enhancers (cluster 4-8) were associated with genes involved in biological processes such as metabolism of xenobiotics, alcohols, vitamins, lipids and nucleotides, regulation of microtubules, cell cycle and regulation of collagen. The SE-2 enhancers (clusters 5-7) were associated with genes involved in biological processes such as regulation of protein localization and transport, skeletal, cartilage and connective tissue morphogenesis and metabolism of xenobiotics, alcohols, lipids, vitamins and nucleotides.

The data indicate that the bivalent H3K9me3-H3K36me2/3 chromatin state is associated with weakly expressed genes, which are regulated in a cell type dependent manner. Therefore, it was further investigated if these regions contain binding sites for regulatory factors. The Re-Map database (Griffon et al. 2015) was used to search for overlap of H3K9me3-H3K36me2/3 peaks with the binding sites of DNA-interacting factors in tens of cell types from hundreds of ChIP-seq experiments. A very significant overlap of the H3K9me3-H3K36me2/3 bivalent state with binding sites of ZNF274, Trim28, CBX3 and SetDB1, all of which are members of the zinc finger-Trim28-SetDB1 pathway, was found. The inventors further searched for available ChIP-seq datasets of any of these proteins in HepG2 cells, and found one for ZNF274. Co-localization of H3K9me3-H3K36me2/3 and ZNF274 signals was observed, which was additionally corroborated by apparent enrichment of H3K9me3-H3K36me2/3 around ZNF274 binding sites, showing that around 60% of all ZNF274 sites are overlaid with H3K9me3-H3K36me2/3 in HepG2 cells.

Since no SetDB1 and KAP1 (also known as Trim28) ChIP-seq datasets were available from HepG2 cells, the inventors reasoned that some of their binding sites might be constitutive and still partially overlap with constitutive H3K9me3-H3K36me2/3 bivalent states obtained from HepG2. Thus, the inventors collected SetDB1 and KAP1 ChIP-seq data from K562 and U2-OS cells, performed k-means clustering around SetDB1 peaks, and observed clusters enriched with the H3K9me3-H3K36me2/3 state.

Taken together, the data indicate a potential link between zinc finger-Trim28-SetDB1 pathway and the H3K9me3-H3K36me2/3 bivalent chromatin state.

Analysis of Cis/Trans Binding of PM to Double Modified Nucleosomes

Figure 9:
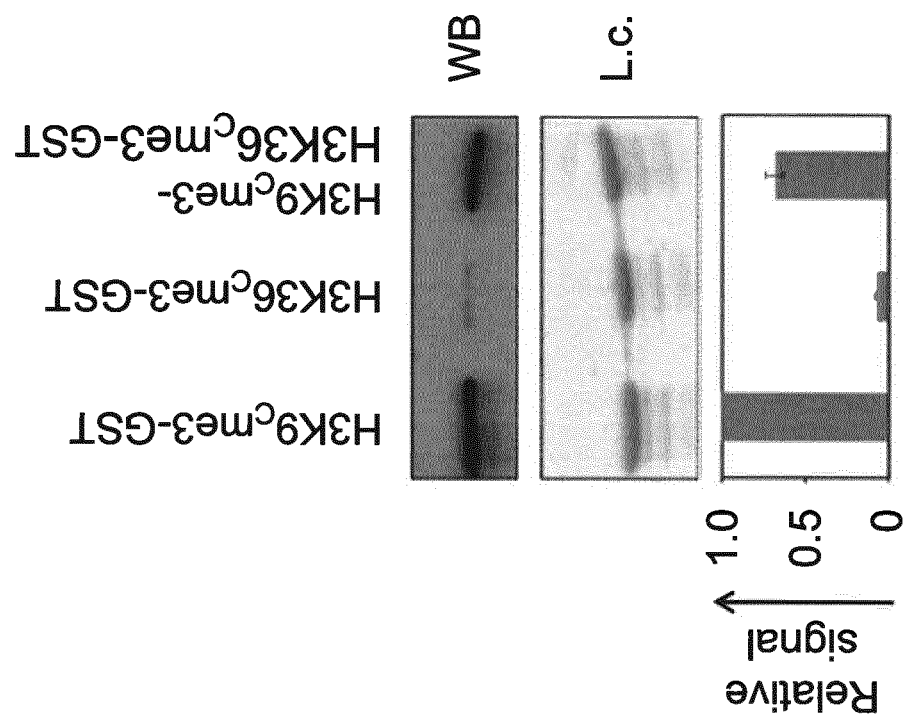
FIG. 9 shows pull-down analysis of MBP tagged PM with H3-GST proteins having trimethyllysine analogs at positions 9 (H3K9$_c$me3-GST), 36 (H3K36$_c$me3-GST) or both (H3K9$_c$me3K36$_c$me3-GST). Precipitated PM proteins were detected with anti-MBP antibody (L.c., loading control).

The inventors found that the affinity of PM to mononucleosomes is higher than the affinity of each of its domains (FIG. 3). The synergistic recognition of H3K36me2/3 and H3K9me3 could be due to binding of PM to the H3K9me3 and H3K36me2/3 modifications on two different histone H3 tails of the same nucleosome (in trans) or to both modifications located next to each other on the same histone H3 tail (in cis). To discriminate these binding modes, a recombinant H3 fragment consisting of the first 60 amino acids N-terminally fused to GST (H3-GST) was generated. Using the methyl-lysine analog technology (Simon et al. 2007), lysine 9, lysine 36 or both from H3-GST were replaced by cysteine (H3K9$_c$, H3K36c, and H3K9$_c$K36$_c$) and subsequently converted to the respective trimethyl analogs (H3K9$_c$me3, H3K36$_c$me3, and H3K9$_c$me3K36$_c$me3). Mass spectrometry analyses indicated a similarly high (almost 100%) efficiency of conversion of methyl lysine analogs. The GST tagged H3 proteins were used as bait for maltose binding protein (MBP) tagged PM pulldown. Washing was performed under stringent conditions. Precipitated proteins were detected by western blot (WB) with anti-MBP antibody as shown in FIG. 9. L.c. designates the loading control (Coomassie Brilliant Blue staining). The bar diagram shows a quantification of the data based on three repetitions. Error bars represent the standard error of mean (SEM). The results show that PM exhibited strongest binding to H3K9$_c$me3, weaker to H3K9$_c$me3-H3K36$_c$me3, and even lower to H3K36$_c$me3 modified H3-GST. The lack of improved binding of PM to double modified H3K9$_c$me3-H3K36$_c$me3 H3-GST when compared to single modified H3K9$_c$me3 H3-GST indicates that PM is not able to bind both modifications in cis. Binding of PM in cis is probably sterically precluded. Hence, the binding of PM to H3K9me3-H3K36me2/3 double modified mononucleosomes observed for example in FIG. 3 is likely to occur in trans. By modifying the design of PM, an artificial protein that is able to bind both modifications in cis may be obtained. The weaker binding of PM to double modified H3K9$_c$me3-H3K36$_c$me3 H3-GST as compared to only H3K9$_c$me3 modified H3-GST might be explained by the fact that in this case an averaged binding affinity to H3K9$_c$me3 and H3K36$_c$me3 was detected. Weaker binding of PM to H3K36$_c$me3 modified H3-GST is in agreement with previous data showing that binding of PM to H3K36me2/3 alone is weakest (FIG. 2).

Figure 10:
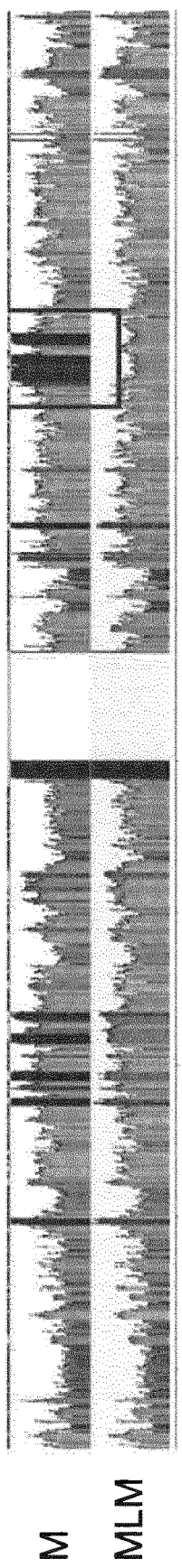
FIG. 10 shows read densities in a section of chromosome 1 obtained by next-generation sequencing of recovered DNA. The DNA was recovered from nucleosomes isolated using the artificial protein MLM, or a single chromodomain of MPP8 (M).

Analysis of the Distribution of Symmetrically and Asymmetrically Modified Nucleosomes To determine the distribution of symmetrically and asymmetrically modified nucleosomes, the inventors compared the next-generation sequencing results obtained from nucleosomes isolated by CIDOP using MLM and M. Read densities were averaged over 100 kb bins and the read densities displayed using SeqMonk (FIG. 10). On average, the results show a very high concordance of the profiles of MLM and M. This was expected given that both MLM and M are specific for H3K9me3. Interestingly, specific regions were identified in which M showed strong binding, but MLM did not, for example the region highlighted by the black box. These regions are candidate regions for having H3K9me3 asymmetrically modified nucleosomes, which for that reason could not be as efficiently precipitated with MLM. This demonstrates successful use of MLM for isolating symmetrically modified nucleosomes, which allows analyzing the distribution of symmetrically and asymmetrically modified nucleosomes.

REFERENCES

Bock, I.; Kudithipudi, S.; Tamas, R.; Kungulovski, G.; Dhayalan, A.; Jeltsch, A., Application of Celluspots peptide arrays for the analysis of the binding specificity of epigenetic reading domains to modified histone tails. *BMC Biochemistry* 2011, 12, 48-59.

Bock, I.; Dhayalan, A.; Kudithipudi, S.; Brandt, O.; Rathert, P.; Jeltsch, A., Detailed specificity analysis of antibodies binding to modified histone tails with peptide arrays. *Epigenetics* 2011, 6(2), 256-263.

Brand, M.; Rampalli, S.; Chaturvedi, C.-P.; F Jeffrey Dilworth, F. J., Analysis of epigenetic modifications of chromatin at specific gene loci by native chromatin immunoprecipitation of nucleosomes isolated using hydroxyapatite chromatography. *Nature Protocols* 2008, 3(3), 398-409.

ENCODE-consortium, An integrated encyclopedia of DNA elements in the human genome. *Nature* 2012, 489, 57-74.

Ernst, J.; Kheradpour, P.; Mikkelsen, T. S.; Shoresh, N.; Ward, L. D.; Epstein, C. B.; Zhang, X.; Wang, L.; Issner, R.; Coyne, M.; et al., Mapping and analysis of chromatin state dynamics in nine human cell types. *Nature* 2011, 473, 43-49.

Griffon, A.; Barbier, Q.; Dalino, J.; van Heiden, J.; Spicuglia, S.; Ballester, B., Integrative analysis of public ChIP-seq experiments reveals a complex multi-cell regulatory landscape. *Nucleic Acids Research* 2015, 43, e27.

Halachev, K.; Bast, H.; Albrecht, F.; Lengauer, T.; Bock, C., EpiExplorer: live exploration and global analysis of large epigenomic datasets. *Genome Biology* 2012, 13, R96.

Jeltsch, A. and Lanio, T., Site-Directed Mutagenesis by Polymerase Chain Reaction. Methods in Molecular Biology 2002, 182: *In Vitro Mutagenesis Protocols,* 2nd ed., 85-94.

Kallio M. A.; Tuimala, J. T.; Hupponen, T.; Klemelä, P.; Gentile, M.; Scheinin, I.; Koski, M.; Kaki, J.; Korpelainen, E. I., Chipster: user-friendly analysis software for microarray and other high-throughput data. *BMC Genomics* 2011, 12, 507-521.

Kent, W. J.; Sugnet, C. W.; Furey, T. S.; Roskin, K. M.; Pringle, T. H.; Zahler, A. M.; Haussler, D., The human genome browser at UCSC. *Genome Research* 2002, 12, 996-1006.

Langmead, B.; Trapnell, C.; Pop, M.; Salzberg, S. L., Ultrafast and memory-efficient alignment of short DNA sequences to the human genome. *Genome Biology* 2009, 10, R25.

Ramirez, F.; Dander, F.; Diehl, S.; Grüning, B. A.; Manke, T., deepTools: a flexible platform for exploring deep-sequencing data. *Nucleic Acids Research* 2014, 42, W187-W191.

Rathert, P.; Dhayalan, A.; Murakami, M.; Zhang, X.; Tamas, R.; Jurkowska, R.; Komatsu, Y.; Shinkai, Y.; Cheng, X.; Jeltsch, A., Protein lysine methyltransferase G9a acts on non-histone targets. *Nature Chemical Biology* 2008, 4(6), 344-346.

Simon, M. D.; Chu, F.; Racki, L. R.; de la Cruz, C. C.; Burlingame, A. L.; Panning, B.; Narlikar, G. J.; Shokat, K. M., The site-specific installation of methyl-lysine analogs into recombinant histones. *Cell* 2007, 128, 1003-1012.

Trapnell, C.; Roberts, A.; Goff, L.; Pertea, G.; Kim, D.; Kelley, D. R.; Pimentel, H.; Salzberg, S. L.; Rinn, J. L.; Pachter, L., Differential gene and transcript expression analysis of RNA-seq experiments with TopHat and Cufflinks. *Nature Protocols* 2012, 7, 562-578.

Welch, R. P.; Lee, C.; Imbriano, P. M.; Patil, S.; Weymouth, T. E.; Smith, R. A.; Scott, L. J.; Sartor, M. A., ChIP-Enrich: gene set enrichment testing for ChIP-seq data. *Nucleic Acids Research* 2014, 42, e105.

Ye, T.; Krebs, A. R.; Choukrallah, M. A.; Keime, C.; Plewniak, F.; Davidson, I.; Tora, L., seqMINER: an integrated ChIP-seq data interpretation platform. *Nucleic Acids Research* 2011 39, e35.

The invention claimed is:

1. An in-vitro method for isolating a nucleosome having a first and a second histone modification, the method comprising the steps of:
   (a) providing an artificial protein, wherein the artificial protein comprises
      a first histone modification binding domain of 50 to 200 amino acids binding to the first histone modification,
      a second histone modification binding domain of 50 to 200 amino acids binding to the second histone modification,
      a linker of 5 to 50 amino acids connecting the first and the second histone modification binding domain, and
      an affinity tag,
      wherein the first histone modification binding domain is the PWWP domain of Dnmt3a and the second histone modification binding domain is the chromodomain of MPP8,
   (b) contacting the artificial protein with a sample comprising nucleosomes to allow formation of a complex of the artificial protein and a nucleosome having the first and the second histone modification; and
   (c) isolating the complex.

2. An in-vitro method for isolating a nucleosome having a first and a second histone modification, the method comprising the steps of:
   (a) providing an artificial protein, wherein the artificial protein comprises
      a first histone modification binding domain of 50 to 200 amino acids binding to the first histone modification,
      a second histone modification binding domain of 50 to 200 amino acids binding to the second histone modification,
      a linker of 5 to 50 amino acids connecting the first and the second histone modification binding domain, and
      an affinity tag;
      wherein the first and/or the second histone modification binding domain is selected from the group consisting of 14-3-3 domain, ADD domain, ankyrin, BAH domain, BIR domain, BRCT domain, tandem BRCT domain, bromodomain, double bromodomain, chromobarrel, chromodomain, double chromodomain, double PHD finger domain, MBT domain, PID domain, PHD domain, double PH domain, PWWP domain, royal family domain, Tudor domain, tandem Tudor domain, WD40 domain, and zinc finger CW domain,
   (b) contacting the artificial protein with a sample comprising nucleosomes to allow formation of a complex of the artificial protein and a nucleosome having the first and the second histone modification;
   (c) isolating the complex;
   (d) providing a first control protein and a second control protein, each control protein comprising a single histone modification binding domain, wherein the single histone modification binding domain of the first control protein is the same as the first histone modification binding domain of the artificial protein and the single histone modification binding domain of the second control protein is the same as the second histone modification binding domain of the artificial protein; and
   (e) contacting the first and the second control protein with a sample comprising nucleosomes to allow formation of a complex of the first control protein and a nucleosome having the first histone modification and/or formation of a complex of the second control protein and a nucleosome having the second histone modification; and
   (f) isolating the complex.

3. The method of claim 2, wherein the first and the second histone modification binding domains are different from each other.

4. The method of claim 2, wherein the first and the second histone modification binding domains are copies of the same domain.

5. The method of claim 2, wherein the first and/or the second histone modification is selected from the group consisting of methylation, phosphorylation, acetylation, and ubiquitylation.

6. The method of claim 2, further comprising the step of:
   (d) analysing the isolated complex.

7. The method of claim 6, wherein the isolated complex is analysed by mass spectrometry.

8. The method of claim 6, wherein the isolated complex is analysed by recovering DNA from the nucleosome and analysing the DNA.

9. The method of claim 8, wherein the DNA is analysed by quantitative PCR and/or next-generation sequencing.

* * * * *

```
                          SEQUENCE LISTING

<160> NUMBER OF SEQ ID NOS: 65

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker of 21 amino acids

<400> SEQUENCE: 1

Gly Gly Phe Gln Pro Ser Gly Pro Lys Gly Leu Glu Pro Pro Leu Glu
1               5                   10                  15

Arg Pro His Arg Asp
            20

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker of 14 amino acids
```

```
<400> SEQUENCE: 2

Gly Gly Phe Gln Pro Ser Gly Pro Lys Gly Leu Glu Pro Pro
1               5                   10

<210> SEQ ID NO 3
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker of 27 amino acids

<400> SEQUENCE: 3

Ser Ser Gly Asn Ser Asn Ala Asn Ser Arg Gly Pro Ser Phe Ser Ser
1               5                   10                  15

Gly Leu Val Pro Leu Ser Leu Arg Gly Ser His
            20                  25

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: forward primer PM-PM1 chr2

<400> SEQUENCE: 4
gtcttaaccg tctgcctaga                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: reverse primer PM-PM1 chr2

<400> SEQUENCE: 5
tggtagattg gcaaatggaa                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: forward primer PM-PM2 chr12

<400> SEQUENCE: 6
gcctctgcat tcagcatttc                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: reverse primer PM-PM2 chr12
```

<400> SEQUENCE: 7
aggttggcca aagacacatc					20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: forward primer PM-PM3 chr7

<400> SEQUENCE: 8
ccagaccagt gcaataagga a					21

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: reverse primer PM-PM3 chr7

<400> SEQUENCE: 9
tgacctttga gggttcaag					19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: forward primer PM-PM5 chr5

<400> SEQUENCE: 10
ctgctcccat gtctgctaca					20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: reverse primer PM-PM5 chr5

<400> SEQUENCE: 11
tggaaggact gcagagaaaa a					21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: forward primer PM-P1 chr12

<400> SEQUENCE: 12
caatgacccc ttcattgacc					20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: reverse primer PM-P1 chr12

<400> SEQUENCE: 13
gggggaatac gtgagggtat                                           20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: forward primer PM-P3 chr1

<400> SEQUENCE: 14
tgcaaagaaa aaggagcaga a                                         21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: reverse primer PM-P3 chr1

<400> SEQUENCE: 15
ccaacaagca aaagaaggaa a                                         21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: forward primer PM-P5 chr9

<400> SEQUENCE: 16
tgctcctttt tcccatcttt t                                         21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: reverse primer PM-P5 chr9

<400> SEQUENCE: 17
gcaaaaccaa gtcgaatgct                                           20

<210> SEQ ID NO 18
<211> LENGTH: 20

<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: forward primer PM-M2 chr5

<400> SEQUENCE: 18
tgcatgatgt tttcctcagc                                               20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: reverse primer PM-M2 chr5

<400> SEQUENCE: 19
atcttgcgca aatgctctg                                                19

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: forward primer PM-M3 chr19

<400> SEQUENCE: 20
ttgtcaccac tgtccaggaa                                               20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: reverse primer PM-M3 chr19

<400> SEQUENCE: 21
cagctgcctc agagacacac                                               20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: forward primer PM-M4 chr5

<400> SEQUENCE: 22
agaacaccat ggaccaccag                                               20

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic

```
primer
<220> FEATURE:
<223> OTHER INFORMATION: reverse primer PM-M4 chr5

<400> SEQUENCE: 23
tttctgaatt ggttctgggt tt                                              22

<210> SEQ ID NO 24
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: nucleic acid PM

<400> SEQUENCE: 24
atgtccccta tactaggtta ttggaaaatt aagggccttg tgcaacccac tcgacttctt     60
ttggaatatc ttgaagaaaa atatgaagag catttgtatg agcgcgatga aggtgataaa    120
tggcgaaaca aaaagtttga attgggtttg agtttccca atcttcctta ttatattgat    180
ggtgatgtta aattaacaca gtctatggcc atcatacgtt atatagctga caagcacaac    240
atgttgggtg gttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgtttttаaa    540 aaacgtattg aagctatccc acaaattgat aagtacttga atccagcaa gtatatagca    600 tggcctttgc agggctggca agccacgttt ggtggtggcg accatcctcc aaaatcggat    660
ctggaagttc tgttccaggg gcccctggga tccccaggaa tcctcggatc cgagtatgag    720
gatggccggg gctttggcat tggagagctg gtgtggggga acttcgggg cttctcctgg    780 tggccaggcc gaattgtgtc ttggtggatg acaggccgga gccgagcagc tgaaggcact    840
cgctgggtca tgtggttcgg agatggcaag ttctcagtgg tgtgtgtgga agcctcatg    900 ccgctgagct ccttctgcag tgcattccac caggccacct acaacaagca gcccatgtac    960
cgcaaagcca tctacgaagt cctccaggtg ccagcagcc gtgccgggaa gctgttttcca   1020 gcttgccatg acagtgatga aagtgacagt ggcaaggctg tggaagtgca gaacaagcag   1080
atgattgaat gggcccctcgg tggcttccag ccctcgggtc ctaagggcct ggagccacca   1140
ctcgagcggc cgcatcgtga cgtgttcgag gtggagaaga tcctggacat gaagaccgag   1200
gggggtaaag ttctttacaa agttcgctgg aaaggctata catcggatga tgatacctgg   1260
gagcccgaga ttcacctgga ggactgtaaa gaagtgcttc ttgaatttag gaagaaaatt   1320
gcagagcccg ggtcgactcg agcggccgca tcgtga                              1356

<210> SEQ ID NO 25
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein PM

<400> SEQUENCE: 25
```

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
        20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
210                 215                 220

Phe Gln Gly Pro Leu Gly Ser Pro Gly Ile Leu Gly Ser Glu Tyr Glu
225                 230                 235                 240

Asp Gly Arg Gly Phe Gly Ile Gly Glu Leu Val Trp Gly Lys Leu Arg
                245                 250                 255

Gly Phe Ser Trp Trp Pro Gly Arg Ile Val Ser Trp Trp Met Thr Gly
                260                 265                 270

Arg Ser Arg Ala Ala Glu Gly Thr Arg Trp Val Met Trp Phe Gly Asp
        275                 280                 285

Gly Lys Phe Ser Val Val Cys Val Glu Lys Leu Met Pro Leu Ser Ser
        290                 295                 300

Phe Cys Ser Ala Phe His Gln Ala Thr Tyr Asn Lys Gln Pro Met Tyr
305                 310                 315                 320

Arg Lys Ala Ile Tyr Glu Val Leu Gln Val Ala Ser Ser Arg Ala Gly
                325                 330                 335

Lys Leu Phe Pro Ala Cys His Asp Ser Asp Glu Ser Asp Ser Gly Lys
                340                 345                 350

Ala Val Glu Val Gln Asn Lys Gln Met Ile Glu Trp Ala Leu Gly Gly
            355                 360                 365

Phe Gln Pro Ser Gly Pro Lys Gly Leu Glu Pro Pro Leu Glu Arg Pro
370                 375                 380

His Arg Asp Val Phe Glu Val Glu Lys Ile Leu Asp Met Lys Thr Glu
385                 390                 395                 400

Gly Gly Lys Val Leu Tyr Lys Val Arg Trp Lys Gly Tyr Thr Ser Asp
                405                 410                 415

Asp Asp Thr Trp Glu Pro Glu Ile His Leu Glu Asp Cys Lys Glu Val
            420                 425                 430

Leu Leu Glu Phe Arg Lys Lys Ile Ala Glu Pro Gly Ser Thr Arg Ala
        435                 440                 445

Ala Ala Ser
    450

<210> SEQ ID NO 26
<211> LENGTH: 1192
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: nucleic acid C7LT

<400> SEQUENCE: 26

```
atgtcccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg agtttcccca atcttcctta ttatattgat    180
ggtgatgtta aattaacaca gtctatggcc atcatacgtt atatagctga caagcacaac    240
atgttgggtg gttgtccaaa agagcgtgca gagatttcaa tgcttgaagg agcggttttg    300 gatattgat acggtgtttc gagaattgca tatagtaaag actttgaaac tctcaaagtt    360 gatttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aaaatcggat    660
ctggaagttc tgttccaggg gcccctggga tccgagcagg tgttcgccgt ggagagcatc    720
cggaagaagc gcgtgcggaa gggtaaagtc gagtatctgg tgaagtggaa aggatggccc    780
ccaaagtaca gcacgtggga gccagaagag cacatcttgg accccgcct cgtcatggcc    840 tacgaggaga aggaggagtc tagcggcaat agtaacgcta acagccgcgg gccgagcttc    900
agcagcggcc tggtgccgtt aagcttgcgc ggcagccatg tgatccgaga tgagtggggc    960
aatcagatct ggatctgccc tgggtgtaac aagcctgacg atgggagtcc catgattggg    1020
tgtgacgact gcgatgactg gtaccactgg ccctgtgttg gaatcatgac tgcaccccca    1080
gaagagatgc agtggttctg ccccaagtgt gcgaacaaga gaaggacaa aaagcacaag    1140 aagaggaagc atcgagccca ctgactcgag cggccgcatc gtgactgact ga           1192
```

<210> SEQ ID NO 27
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein C7LT

<400> SEQUENCE: 27

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu 20                  25                  30
Tyr Glu Arg Asp Glu Gly Asp Lys Trp Arg Asn Lys Lys Phe Glu Leu
        35                  40                  45
Gly Leu Glu Phe Pro Asn Leu Pro Tyr Tyr Ile Asp Gly Asp Val Lys
 50                  55                  60
Leu Thr Gln Ser Met Ala Ile Ile Arg Tyr Ile Ala Asp Lys His Asn
 65                  70                  75                  80
Met Leu Gly Gly Cys Pro Lys Glu Arg Ala Glu Ile Ser Met Leu Glu
                85                  90                  95
Gly Ala Val Leu Asp Ile Arg Tyr Gly Val Ser Arg Ile Ala Tyr Ser
            100                 105                 110
Lys Asp Phe Glu Thr Leu Lys Val Asp Phe Leu Ser Lys Leu Pro Glu
        115                 120                 125
Met Leu Lys Met Phe Glu Asp Arg Leu Cys His Lys Thr Tyr Leu Asn
    130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
            180                 185                 190
Leu Lys Ser Ser Lys Tyr Ile Ala Trp Pro Leu Gln Gly Trp Gln Ala
        195                 200                 205
Thr Phe Gly Gly Gly Asp His Pro Pro Lys Ser Asp Leu Glu Val Leu
    210                 215                 220
Phe Gln Gly Pro Leu Gly Ser Glu Gln Val Phe Ala Val Glu Ser Ile
225                 230                 235                 240
Arg Lys Lys Arg Val Arg Lys Gly Lys Val Glu Tyr Leu Val Lys Trp
                245                 250                 255
Lys Gly Trp Pro Pro Lys Tyr Ser Thr Trp Glu Pro Glu Glu His Ile
            260                 265                 270
Leu Asp Pro Arg Leu Val Met Ala Tyr Glu Glu Lys Glu Glu Ser Ser
        275                 280                 285
Gly Asn Ser Asn Ala Asn Ser Arg Gly Pro Ser Phe Ser Ser Gly Leu
    290                 295                 300
Val Pro Leu Ser Leu Arg Gly Ser His Val Ile Arg Asp Glu Trp Gly
305                 310                 315                 320
Asn Gln Ile Trp Ile Cys Pro Gly Cys Asn Lys Pro Asp Asp Gly Ser
                325                 330                 335
Pro Met Ile Gly Cys Asp Asp Cys Asp Asp Trp Tyr His Trp Pro Cys
            340                 345                 350
Val Gly Ile Met Thr Ala Pro Pro Glu Glu Met Gln Trp Phe Cys Pro
        355                 360                 365
Lys Cys Ala Asn Lys Lys Asp Lys Lys His Lys Lys Arg Lys His
    370                 375                 380
Arg Ala His
385

<210> SEQ ID NO 28
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide <220> FEATURE:
<223> OTHER INFORMATION: nucleic acid PT

<400> SEQUENCE: 28

```
atgtcccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg agtttccca atcttcctta ttatattgat     180
ggtgatgtta aattaacaca gtctatggcc atcatacgtt atatagctga caagcacaac    240
atgttgggtg ttgtccaaa agagcgtgca gagatttcaa tgcttgaagg agcggttttg     300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca     600
tggcctttgc agggctggca agccacgttt ggtggtggcg accatcctcc aaaatcggat    660
ctggaagttc tgttccaggg gccccctggga tccccaggaa tcctcggatc cgagtatgag   720
gatggccggg gctttggcat ggagagctg tgtggggga acttcgggg cttctcctgg       780
tggccaggcc gaattgtgtc ttggtggatg acaggccga gccgagcagc tgaaggcact    840
cgctgggtca tgtggttcgg agatggcaag ttctcagtgg tgtgtgtgga agctcatg     900
ccgctgagct ccttctgcag tgcattccac caggccacct acaacaagca gcccatgtac   960
cgcaaagcca tctacgaagt cctccaggtg gccagcagcc gtgccgggaa gctgtttcca  1020
gcttgccatg acagtgatga agtgacagt ggcaaggctg tggaagtgca gaacaagcag    1080
atgattgaat gggccctcgg tggcttccag ccctcgggtc ctaagggcct ggagccacca   1140
ctcgagcggc cgcatcgtga cgtgatccga gatgagtggg gcaatcagat ctggatctgc   1200
cctgggtgta acaagcctga cgatgggagt cccatgattg ggtgtgacga ctgcgatgac   1260
tggtaccact ggccctgtgt tggaatcatg actgcacccc cagaagagat gcagtggttc   1320
tgccccaagt gtgcgaacaa gaagaaggac aaaaagcaca gaagaggaa gcatcgagcc    1380
cactga                                                              1386
```

<210> SEQ ID NO 29
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: protein PT

<400> SEQUENCE: 29

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
```

Met Leu Gly Gly Cys Pro Lys Glu Arg Ala Glu Ile Ser Met Leu Glu
65                  70                  75                  80

Gly Ala Val Leu Asp Ile Arg Tyr Gly Val Ser Arg Ile Ala Tyr Ser
            85                  90                  95

Lys Asp Phe Glu Thr Leu Lys Val Asp Phe Leu Ser Lys Leu Pro Glu
100                 105                 110

Met Leu Lys Met Phe Glu Asp Arg Leu Cys His Lys Thr Tyr Leu Asn
        115                 120                 125

Gly Asp His Val Thr His Pro Asp Phe Met Leu Tyr Asp Ala Leu Asp
130                 135                 140

Val Val Leu Tyr Met Asp Pro Met Cys Leu Asp Ala Phe Pro Lys Leu
145                 150                 155                 160

Val Cys Phe Lys Lys Arg Ile Glu Ala Ile Pro Gln Ile Asp Lys Tyr
            165                 170                 175

Leu Lys Ser Ser Lys Tyr Ile Ala Trp Pro Leu Gln Gly Trp Gln Ala
        180                 185                 190

Thr Phe Gly Gly Gly Asp His Pro Pro Lys Ser Asp Leu Glu Val Leu
    195                 200                 205

Phe Gln Gly Pro Leu Gly Ser Glu Tyr Glu Asp Gly Arg Gly Phe Gly
210                 215                 220

Ile Gly Glu Leu Val Trp Gly Lys Leu Arg Gly Phe Ser Trp Trp Pro
225                 230                 235                 240

Gly Arg Ile Val Ser Trp Trp Met Thr Gly Arg Ser Arg Ala Ala Glu
            245                 250                 255

Gly Thr Arg Trp Val Met Trp Phe Gly Asp Gly Lys Phe Ser Val Val
        260                 265                 270

Cys Val Glu Lys Leu Met Pro Leu Ser Ser Phe Cys Ser Ala Phe His
    275                 280                 285

Gln Ala Thr Tyr Asn Lys Gln Pro Met Tyr Arg Lys Ala Ile Tyr Glu
290                 295                 300

Val Leu Gln Val Ala Ser Ser Arg Ala Gly Lys Leu Phe Pro Ala Cys
305                 310                 315                 320

His Asp Ser Asp Glu Ser Asp Ser Gly Lys Ala Val Glu Val Gln Asn
            325                 330                 335

Lys Gln Met Ile Glu Trp Ala Leu Gly Gly Phe Gln Pro Ser Gly Pro
        340                 345                 350

Lys Gly Leu Glu Pro Pro Val Ile Arg Asp Glu Trp Gly Asn Gln Ile
    355                 360                 365

Trp Ile Cys Pro Gly Cys Asn Lys Pro Asp Asp Gly Ser Pro Met Ile
370                 375                 380

Gly Cys Asp Asp Cys Asp Asp Trp Tyr His Trp Pro Cys Val Gly Ile
385                 390                 395                 400

Met Thr Ala Pro Pro Glu Glu Met Gln Trp Phe Cys Pro Lys Cys Ala
            405                 410                 415

Asn Lys Lys Lys Asp Lys Lys His Lys Arg Lys His Arg Ala His
        420                 425                 430

435                 440                 445

<210> SEQ ID NO 30
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: nucleic acid MLM

<400> SEQUENCE: 30

```
atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg gttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600
tggcctttgc agggctggca agccacgttt ggtggtggcg accatcctcc aaaatcggat    660
ctggaagttc tgttccaggg gcccctggga tccgtgttcg aggtggagaa gatcctggac    720
atgaagaccg agggggggtaa agttctttac aaagttcgct ggaaaggcta tacatcggat    780
gatgataacct gggagcccga gattcacctg gaggactgta agaagtgct tcttgaattt    840
aggaagaaaa ttgcagagtc tagcggcaat agtaacgcta acagccgcgg gccgagcttc    900
agcagcggcc tggtgccgtt aagcttgcgc ggcagccatg tgttcgaggt ggagaagatc    960
ctggacatga agaccgaggg gggtaaagtt ctttacaaag ttcgctggaa aggctataca   1020
tcggatgatg atacctggga gcccgagatt cacctggagg actgtaaaga agtgcttctt   1080
gaatttagga agaaaattgc agagctcgag cggccgcatc gtgactga                1128
```

<210> SEQ ID NO 31
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein MLM

<400> SEQUENCE: 31

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125
```

```
Met Leu Lys Met Phe Glu Asp Arg Leu Cys His Lys Thr Tyr Leu Asn
            130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
210                 215                 220

Phe Gln Gly Pro Leu Gly Ser Val Phe Glu Val Glu Lys Ile Leu Asp
225                 230                 235                 240

Met Lys Thr Glu Gly Gly Lys Val Leu Tyr Lys Val Arg Trp Lys Gly
                245                 250                 255

Tyr Thr Ser Asp Asp Asp Thr Trp Glu Pro Glu Ile His Leu Glu Asp
            260                 265                 270

Cys Lys Glu Val Leu Leu Glu Phe Arg Lys Lys Ile Ala Glu Ser Ser
        275                 280                 285

Gly Asn Ser Asn Ala Asn Ser Arg Gly Pro Ser Phe Ser Ser Gly Leu
290                 295                 300

Val Pro Leu Ser Leu Arg Gly Ser His Val Phe Glu Val Glu Lys Ile
305                 310                 315                 320

Leu Asp Met Lys Thr Glu Gly Gly Lys Val Leu Tyr Lys Val Arg Trp
                325                 330                 335

Lys Gly Tyr Thr Ser Asp Asp Asp Thr Trp Glu Pro Glu Ile His Leu
            340                 345                 350

Glu Asp Cys Lys Glu Val Leu Leu Glu Phe Arg Lys Lys Ile Ala Glu
        355                 360                 365

Leu Glu Arg Pro His Arg Asp
370                 375

<210> SEQ ID NO 32
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: nucleic acid MLP

<400> SEQUENCE: 32 atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg ttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttatatga cgctcttgat    480
gttgttttat acatggaccc aatgtgcctg gatgcgttcc caaaattagt ttgttttaaa    540
```

```
aaacgtattg aagctatccc acaaattgat aagtacttga aatccagcaa gtatatagca    600
tggcctttgc agggctggca agccacgttt ggtggtggcg accatcctcc aaaatcggat    660
ctggaagttc tgttccaggg gcccctggga tccccaggaa tcctcgtgtt cgaggtggag    720
aagatcctgg acatgaagac cgaggggggt aaagttcttt acaaagttcg ctggaaaggc    780
tatacatcgg atgatgatac ctgggagccc gagattcacc tggaggactg taaagaagtg    840
cttcttgaat ttaggaagaa aattgcagag tctagcggca atagtaacgc taacagccgc    900
gggccgagct tcagcagcgg cctggtgccg ttaagcttgc gcggcagcca tggatccgag    960
tatgaggatg ccgggggctt tggcattgga gagctggtgt gggggaaact tcggggcttc   1020
tcctggtggc caggccgaat tgtgtcttgg tggatgacag gccggagccg agcagctgaa   1080
ggcactcgct gggtcatgtg gttcggagat ggcaagttct cagtggtgtg tgtgagaaag   1140
ctcatgccgc tgagctcctt ctgcagtgca ttccaccagg ccacctacaa caagcagccc   1200
atgtaccgca aagccatcta cgaagtcctc caggtggcca gcagccgtgc cgggaagctg   1260
tttccagctt gccatgacag tgatgaaagt gacagtggca aggctgtgga agtgcagaac   1320
aagcagatga ttgaatgggc cctcggtggc ttccagccct cgggtcctaa gggcctggag   1380
ccaccactcg agcggccgca tcgtgactga                                    1410
```

<210> SEQ ID NO 33
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein MLP

<400> SEQUENCE: 33

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190
```

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Glu Val Leu
        210                 215                 220

Phe Gln Gly Pro Leu Gly Ser Pro Gly Ile Leu Val Phe Glu Val Glu
225                 230                 235                 240

Lys Ile Leu Asp Met Lys Thr Glu Gly Gly Lys Val Leu Tyr Lys Val
                245                 250                 255

Arg Trp Lys Gly Tyr Thr Ser Asp Asp Thr Trp Glu Pro Glu Ile
            260                 265                 270

His Leu Glu Asp Cys Lys Glu Val Leu Leu Glu Phe Arg Lys Lys Ile
        275                 280                 285

Ala Glu Ser Ser Gly Asn Ser Asn Ala Asn Ser Arg Gly Pro Ser Phe
290                 295                 300

Ser Ser Gly Leu Val Pro Leu Ser Leu Arg Gly Ser His Gly Ser Glu
305                 310                 315                 320

Tyr Glu Asp Gly Arg Gly Phe Gly Ile Gly Glu Leu Val Trp Gly Lys
                325                 330                 335

Leu Arg Gly Phe Ser Trp Trp Pro Gly Arg Ile Val Ser Trp Trp Met
            340                 345                 350

Thr Gly Arg Ser Arg Ala Ala Glu Gly Thr Arg Trp Val Met Trp Phe
        355                 360                 365

Gly Asp Gly Lys Phe Ser Val Val Cys Val Glu Lys Leu Met Pro Leu
370                 375                 380

Ser Ser Phe Cys Ser Ala Phe His Gln Ala Thr Tyr Asn Lys Gln Pro
385                 390                 395                 400

Met Tyr Arg Lys Ala Ile Tyr Glu Val Leu Gln Val Ala Ser Ser Arg
                405                 410                 415

Ala Gly Lys Leu Phe Pro Ala Cys His Asp Ser Asp Glu Ser Asp Ser
            420                 425                 430

Gly Lys Ala Val Glu Val Gln Asn Lys Gln Met Ile Glu Trp Ala Leu
        435                 440                 445

Gly Gly Phe Gln Pro Ser Gly Pro Lys Gly Leu Glu Pro Pro Leu Glu
    450                 455                 460

Arg Pro His Arg Asp
465

<210> SEQ ID NO 34
<211> LENGTH: 1437
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: nucleic acid PLM

<400> SEQUENCE: 34 atgtcccta tactaggtta ttggaaaatt aagggccttg tgcaacccac tcgacttctt    60
ttggaatatc ttgaagaaaa atatgaagag catttgtatg agcgcgatga aggtgataaa   120
tggcgaaaca aaagtttga attgggtttg gagtttccca atcttcctta ttatattgat   180
ggtgatgtta aattaacaca gtctatggcc atcatacgtt atatagctga caagcacaac   240
atgttgggtg ttgtcccaaa agagcgtgca gagatttcaa tgcttgaagg agcggttttg   300
gatattagat acggtgtttc gagaattgca tatagtaaag actttgaaac tctcaaagtt   360

```
gatttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600
tggcctttgc agggctggca agccacgttt ggtggtggcg accatcctcc aaaatcggat    660
ctggaagttc tgttccaggg gcccctggga tccccaggaa tcctcggatc cgagtatgag    720
gatggccggg gctttggcat tggagagctg gtgtggggga acttcgggg cttctcctgg    780
tggccaggcc gaattgtgtc ttggtggatg acaggccgga gccgagcagc tgaaggcact    840
cgctgggtca tgtggttcgg agatggcaag ttctcagtgg tgtgtgtgga aagctcatg    900
ccgctgagct ccttctgcag tgcattccac caggccacct acaacaagca gcccatgtac    960
cgcaaagcca tctacgaagt cctccaggtg gccagcagcc gtgccgggaa gctgtttcca   1020
gcttgccatg acagtgatga aagtgacagt ggcaaggctg tggaagtgca gaacaagcag   1080
atgattgaat gggccctcgg tggcttccag ccctcgggtc ctaagggcct ggagccacca   1140
ctcgagcggc cgcatcgtga ctctagcggc aatagtaacg ctaacagccg cgggccgagc   1200
ttcagcagcg gcctggtgcc gttaagcttg cgcggcagcc atgtgttcga ggtggagaag   1260
atcctggaca tgaagaccga gggggtaaa gttcttaca aagttcgctg aaaggctat    1320
acatcggatg atgatacctg ggagcccgag attcacctgg aggactgtaa agaagtgctt   1380
cttgaattta ggaagaaaat tgcagagccc gggtcgactc gagcggccgc atcgtga       1437
```

<210> SEQ ID NO 35
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein PLM

<400> SEQUENCE: 35

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
            165                 170                 175

Val Cys Phe Lys Lys Arg Ile Glu Ala Ile Pro Gln Ile Asp Lys Tyr
        180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Glu Val Leu
        210                 215                 220

Phe Gln Gly Pro Leu Gly Ser Pro Gly Ile Leu Gly Ser Glu Tyr Glu
225                 230                 235                 240

Asp Gly Arg Gly Phe Gly Ile Gly Glu Leu Val Trp Gly Lys Leu Arg
            245                 250                 255

Gly Phe Ser Trp Trp Pro Gly Arg Ile Val Ser Trp Trp Met Thr Gly
        260                 265                 270

Arg Ser Arg Ala Ala Glu Gly Thr Arg Trp Val Met Trp Phe Gly Asp
    275                 280                 285

Gly Lys Phe Ser Val Val Cys Val Glu Lys Leu Met Pro Leu Ser Ser
        290                 295                 300

Phe Cys Ser Ala Phe His Gln Ala Thr Tyr Asn Lys Gln Pro Met Tyr
305                 310                 315                 320

Arg Lys Ala Ile Tyr Glu Val Leu Gln Val Ala Ser Ser Arg Ala Gly
            325                 330                 335

Lys Leu Phe Pro Ala Cys His Asp Ser Asp Glu Ser Asp Ser Gly Lys
        340                 345                 350

Ala Val Glu Val Gln Asn Lys Gln Met Ile Glu Trp Ala Leu Gly Gly
            355                 360                 365

Phe Gln Pro Ser Gly Pro Lys Gly Leu Glu Pro Pro Leu Glu Arg Pro
        370                 375                 380

His Arg Asp Ser Ser Gly Asn Ser Asn Ala Asn Ser Arg Gly Pro Ser
385                 390                 395                 400

Phe Ser Ser Gly Leu Val Pro Leu Ser Leu Arg Gly Ser His Val Phe
            405                 410                 415

Glu Val Glu Lys Ile Leu Asp Met Lys Thr Gly Gly Lys Val Leu
            420                 425                 430

Tyr Lys Val Arg Trp Lys Gly Tyr Thr Ser Asp Asp Thr Trp Glu
            435                 440                 445

Pro Glu Ile His Leu Glu Asp Cys Lys Glu Val Leu Leu Glu Phe Arg
450                 455                 460

Lys Lys Ile Ala Glu Pro Gly Ser Thr Arg Ala Ala Ser
465                 470                 475

<210> SEQ ID NO 36
<211> LENGTH: 1730
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: nucleic acid PLP

<400> SEQUENCE: 36 atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaaagtttga attgggtttg gagtttccca atcttcctta ttatattgat    180

```
ggtgatgtta aattaacaca gtctatggcc atcatacgtt atatagctga caagcacaac    240
atgttgggtg ttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aaaatcggat    660
ctggaagttc tgttccaggg gcccctggga tccccaggaa tcctcggatc cgagtatgag    720
gatggccggg gctttggcat ggagagctg gtgtggggga acttcgggg cttctcctgg    780 tggccaggcc gaattgtgtc ttggtggatg acaggccgga gccgagcagc tgaaggcact    840
cgctgggtca tgtggttcgg agatggcaag ttctcagtgg tgtgtgtgga aagctcatg    900 ccgctgagct ccttctgcag tgcattccac caggccacct acaacaagca gcccatgtac    960
cgcaaagcca tctacgaagt cctccaggtg ccagcagcc gtgccgggaa gctgtttcca   1020
gcttgccatg acagtgatga agtgacagt ggcaaggctg tggaagtgca gaacaagcag   1080
atgattgaat gggccctcgg tggcttccag ccctcgggtc ctaagggcct ggagccacca   1140
ctcgagcggc cgcatcgtga ctctagcggc aatagtaacg ctaacagccg cgggccgagc   1200
ttcagcagag ccaccactcg agcggccgca tcgtgaccgg cctggtgccg ttaagcttgc   1260
gcggcagcca tggatccgag tatgaggatg gccggggctt tggcattgga gagctggtgt   1320
gggggaaact tcggggcttc tcctggtggc aggccgaat tgtgtcttgg tggatgacag   1380
gccggagccg agcagctgaa ggcactcgct gggtcatgtg gttcggagat ggcaagttct   1440
cagtggtgtg tgtggagaag ctcatgccgc tgagctcctt ctgcagtgca ttccaccagg   1500
ccacctacaa caagcagccc atgtaccgca aagccatcta cgaagtcctc caggtggcca   1560
gcagccgtgc cgggaagctg tttccagctt gccatgacag tgatgaaagt gacagtggca   1620
aggctgtgga agtgcagaac aagcagatga ttgaatgggc cctcggtggc ttccagcccc   1680
cgggtcctaa gggcctggag ccaccactcg agcggccgca tcgtgactga                1730
```

<210> SEQ ID NO 37
<211> LENGTH: 566
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: protein PLP

<400> SEQUENCE: 37

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
```

-continued

```
                65                  70                  75                  80
        Met Leu Gly Gly Cys Pro Lys Glu Arg Ala Glu Ile Ser Met Leu Glu
                            85                  90                  95

Gly Ala Val Leu Asp Ile Arg Tyr Gly Val Ser Arg Ile Ala Tyr Ser
                        100                 105                 110

Lys Asp Phe Glu Thr Leu Lys Val Asp Phe Leu Ser Lys Leu Pro Glu
                    115                 120                 125

Met Leu Lys Met Phe Glu Asp Arg Leu Cys His Lys Thr Tyr Leu Asn
                130                 135                 140

Gly Asp His Val Thr His Pro Asp Phe Met Leu Tyr Asp Ala Leu Asp
        145                 150                 155                 160

Val Val Leu Tyr Met Asp Pro Met Cys Leu Asp Ala Phe Pro Lys Leu
                            165                 170                 175

Val Cys Phe Lys Lys Arg Ile Glu Ala Ile Pro Gln Ile Asp Lys Tyr
                        180                 185                 190

Leu Lys Ser Ser Lys Tyr Ile Ala Trp Pro Leu Gln Gly Trp Gln Ala
                    195                 200                 205

Thr Phe Gly Gly Gly Asp His Pro Pro Lys Ser Asp Leu Glu Val Leu
                210                 215                 220

Phe Gln Gly Pro Leu Gly Ser Pro Gly Ile Leu Gly Ser Glu Tyr Glu
        225                 230                 235                 240

Asp Gly Arg Gly Phe Gly Ile Gly Glu Leu Val Trp Gly Lys Leu Arg
                            245                 250                 255

Gly Phe Ser Trp Trp Pro Gly Arg Ile Val Ser Trp Trp Met Thr Gly
                        260                 265                 270

Arg Ser Arg Ala Ala Glu Gly Thr Arg Trp Val Met Trp Phe Gly Asp
                    275                 280                 285

Gly Lys Phe Ser Val Val Cys Val Glu Lys Leu Met Pro Leu Ser Ser
                290                 295                 300

Phe Cys Ser Ala Phe His Gln Ala Thr Tyr Asn Lys Gln Pro Met Tyr
        305                 310                 315                 320

Arg Lys Ala Ile Tyr Glu Val Leu Gln Val Ala Ser Ser Arg Ala Gly
                            325                 330                 335

Lys Leu Phe Pro Ala Cys His Asp Ser Asp Glu Ser Asp Ser Gly Lys
                        340                 345                 350

Ala Val Glu Val Gln Asn Lys Gln Met Ile Glu Trp Ala Leu Gly Gly
                    355                 360                 365

Phe Gln Pro Ser Gly Pro Lys Gly Leu Glu Pro Pro Leu Glu Arg Pro
                370                 375                 380

His Arg Asp Ser Ser Gly Asn Ser Asn Ala Asn Ser Arg Gly Pro Ser
        385                 390                 395                 400

Phe Ser Ser Gly Leu Val Pro Leu Ser Leu Arg Gly Ser His Gly Ser
                            405                 410                 415

Glu Tyr Glu Asp Gly Arg Gly Phe Gly Ile Gly Glu Leu Val Trp Gly
                        420                 425                 430

Lys Leu Arg Gly Phe Ser Trp Trp Pro Gly Arg Ile Val Ser Trp Trp
                    435                 440                 445

Met Thr Gly Arg Ser Arg Ala Ala Glu Gly Thr Arg Trp Val Met Trp
                450                 455                 460

Phe Gly Asp Gly Lys Phe Ser Val Val Cys Val Glu Lys Leu Met Pro
        465                 470                 475                 480

Leu Ser Ser Phe Cys Ser Ala Phe His Gln Ala Thr Tyr Asn Lys Gln
                            485                 490                 495
```

Pro Met Tyr Arg Lys Ala Ile Tyr Glu Val Leu Gln Val Ala Ser Ser
                500                 505                 510

Arg Ala Gly Lys Leu Phe Pro Ala Cys His Asp Ser Asp Glu Ser Asp
        515                 520                 525

Ser Gly Lys Ala Val Glu Val Gln Asn Lys Gln Met Ile Glu Trp Ala
    530                 535                 540

Leu Gly Gly Phe Gln Pro Ser Gly Pro Lys Gly Leu Glu Pro Pro Leu
545                 550                 555                 560

Glu Arg Pro His Arg Asp
                565

<210> SEQ ID NO 38
<211> LENGTH: 1602
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: nucleic acid PP

<400> SEQUENCE: 38 atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg gttgtccaaa agagcgtgca gagatttcaa tgcttgaagg agcggttttg    300
gatattagat acgtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aaaatcggat    660
ctggaagttc tgttccaggg gccccctgga tccgagtatg aggatggccg gggctttggc    720
attggagagc tggtgtgggg gaaacttcgg gcttctcct ggtggccagg ccgaattgtg    780
tcttggtgga tgacaggccg gagccgagca gctgaaggca ctcgctgggt catgtggttc    840
ggagatggca agttctcagt ggtgtgtgtg agaagctca tgccgctgag ctccttctgc    900
agtgcattcc accaggccac ctacaacaag cagcccatgt accgcaaagc catctacgaa    960
gtcctccagg tggccagcag ccgtgccggg aagctgtttc agcttgcca tgacagtgat   1020 gaaagtgaca gtggcaaggc tgtggaagtg cagaacaagc agatgattga atgggccctc   1080
ggtggcttcc agccctcggg tcctaagggc ctggagccac cactcgagcg gccgcatcgt   1140
gacggatccg agtatgagga tggccggggc tttggcattg gagagctggt gtgggggaaa   1200
cttcggggct ctcctggtg gccaggccga attgtgtctt ggtggatgac aggccggagc   1260
cgagcagctg aaggcactcg ctgggtcatg tggttcggag atggcaagtt ctcagtggtg   1320
tgtgtggaga agctcatgcc gctgagctcc ttctgcagtg cattccacca ggccacctac   1380
aacaagcagc ccatgtaccg caaagccatc tacgaagtcc tccaggtggc cagcagccgt   1440
gccgggaagc tgtttccagc ttgccatgac agtgatgaaa gtgacagtgg caaggctgtg   1500

```
gaagtgcaga acaagcagat gattgaatgg gccctcggtg gcttccagcc ctcgggtcct    1560
aagggcctgg agccaccact cgagcggccg catcgtgact ga                       1602
```

<210> SEQ ID NO 39
<211> LENGTH: 533
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein PP

<400> SEQUENCE: 39

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
    210                 215                 220

Phe Gln Gly Pro Leu Gly Ser Glu Tyr Glu Asp Gly Arg Gly Phe Gly
225                 230                 235                 240

Ile Gly Glu Leu Val Trp Gly Lys Leu Arg Gly Phe Ser Trp Trp Pro
                245                 250                 255

Gly Arg Ile Val Ser Trp Trp Met Thr Gly Arg Ser Arg Ala Ala Glu
            260                 265                 270

Gly Thr Arg Trp Val Met Trp Phe Gly Asp Gly Lys Phe Ser Val Val
        275                 280                 285

Cys Val Glu Lys Leu Met Pro Leu Ser Ser Phe Cys Ser Ala Phe His
    290                 295                 300

Gln Ala Thr Tyr Asn Lys Gln Pro Met Tyr Arg Lys Ala Ile Tyr Glu
305                 310                 315                 320

Val Leu Gln Val Ala Ser Ser Arg Ala Gly Lys Leu Phe Pro Ala Cys
                325                 330                 335
```

```
His Asp Ser Asp Glu Ser Asp Ser Gly Lys Ala Val Glu Val Gln Asn
                340                 345                 350

Lys Gln Met Ile Glu Trp Ala Leu Gly Gly Phe Gln Pro Ser Gly Pro
            355                 360                 365

Lys Gly Leu Glu Pro Pro Leu Glu Arg Pro His Arg Asp Gly Ser Glu
        370                 375                 380

Tyr Glu Asp Gly Arg Gly Phe Gly Ile Gly Glu Leu Val Trp Gly Lys
385                 390                 395                 400

Leu Arg Gly Phe Ser Trp Trp Pro Gly Arg Ile Val Ser Trp Trp Met
                405                 410                 415

Thr Gly Arg Ser Arg Ala Ala Glu Gly Thr Arg Trp Val Met Trp Phe
            420                 425                 430

Gly Asp Gly Lys Phe Ser Val Val Cys Val Glu Lys Leu Met Pro Leu
        435                 440                 445

Ser Ser Phe Cys Ser Ala Phe His Gln Ala Thr Tyr Asn Lys Gln Pro
    450                 455                 460

Met Tyr Arg Lys Ala Ile Tyr Glu Val Leu Gln Val Ala Ser Ser Arg
465                 470                 475                 480

Ala Gly Lys Leu Phe Pro Ala Cys His Asp Ser Asp Glu Ser Asp Ser
                485                 490                 495

Gly Lys Ala Val Glu Val Gln Asn Lys Gln Met Ile Glu Trp Ala Leu
            500                 505                 510

Gly Gly Phe Gln Pro Ser Gly Pro Lys Gly Leu Glu Pro Pro Leu Glu
        515                 520                 525

Arg Pro His Arg Asp
    530

<210> SEQ ID NO 40
<211> LENGTH: 1524
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: nucleic acid MLdT

<400> SEQUENCE: 40
atgtcccctg tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg agtttcccca tcttccttta ttatattgat     180
ggtgatgtta aattaacaca gtctatggcc atcatacgtt atatagctga caagcacaac     240
atgttgggtg ttgtccaaa agagcgtgca gagatttcaa tgcttgaagg agcggttttg     300
gatattagat acgtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgttttaaa     540
aaacgtattg aagctatccc acaaattgat aagtacttga atccagcaa gtatatagca     600 tggcctttgc agggctggca agccacgttt ggtggtggcg accatcctcc aaaatcggat     660
ctggaagttc tgttccaggg gcccctggga tccgtgttcg aggtggagaa gatcctggac     720
atgaagaccg aggggggtaa agttcttac aaagttcgct ggaaaggcta acatcggat     780
```

```
gatgatacct gggagcccga gattcacctg gaggactgta agaagtgct tcttgaattt    840 aggaagaaaa ttgcagagtc tagcggcaat agtaacgcta acagccgcgg gccgagcttc    900
agcagcggcc tggtgccgtt aagcttgcgc ggcagccata ctgccttcca tgtgagctgc    960
gcccaggctg ccggtgtgat gatgcagcct gacgactggc cttttgtggt cttcattacc    1020
tgctttcggc acaagattcc taatttggag cgtgccaagg gggccttgca aagcatcact    1080
gcaggccaga agtcattag caagcataag aacgggcgct tctaccagtg tgaagtggtc    1140
aggctcacca ccgagacctt ctatgaagtc aactttgatg atggctcctt cagcgacaat    1200
ctttatcctg aggacatagt gagccaggac tgtctccagt ttggtcctcc tgctgaaggg    1260
gaagtggtcc aagtgagatg gacagacggc caagtctatg gagccaagtt tgtggcctcc    1320
caccctatcc aaatgtacca ggtggagttt gaggatggct acaacttgt ggttaagaga    1380 gatgatgtat acacactgga tgaagagctt cccaagagag tcaaatctag actgtcagta    1440
gcctcagaca tgcgcttcaa tgagattttc acagagaaag aggttaagca agaaaagaaa    1500
cggcaacgag ttatcaactc atga                                            1524
```

<210> SEQ ID NO 41
<211> LENGTH: 507
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein MLdT

<400> SEQUENCE: 41

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu

```
            210                 215                 220
Phe Gln Gly Pro Leu Gly Ser Val Phe Glu Val Glu Lys Ile Leu Asp
225                 230                 235                 240

Met Lys Thr Glu Gly Gly Lys Val Leu Tyr Lys Val Arg Trp Lys Gly
                245                 250                 255

Tyr Thr Ser Asp Asp Thr Trp Glu Pro Glu Ile His Leu Glu Asp
                260                 265                 270

Cys Lys Glu Val Leu Leu Glu Phe Arg Lys Lys Ile Ala Glu Ser Ser
                275                 280                 285

Gly Asn Ser Asn Ala Asn Ser Arg Gly Pro Ser Phe Ser Ser Gly Leu
                290                 295                 300

Val Pro Leu Ser Leu Arg Gly Ser His Thr Ala Phe His Val Ser Cys
305                 310                 315                 320

Ala Gln Ala Ala Gly Val Met Met Gln Pro Asp Asp Trp Pro Phe Val
                325                 330                 335

Val Phe Ile Thr Cys Phe Arg His Lys Ile Pro Asn Leu Glu Arg Ala
                340                 345                 350

Lys Gly Ala Leu Gln Ser Ile Thr Ala Gly Gln Lys Val Ile Ser Lys
                355                 360                 365

His Lys Asn Gly Arg Phe Tyr Gln Cys Glu Val Val Arg Leu Thr Thr
                370                 375                 380

Glu Thr Phe Tyr Glu Val Asn Phe Asp Asp Gly Ser Phe Ser Asp Asn
385                 390                 395                 400

Leu Tyr Pro Glu Asp Ile Val Ser Gln Asp Cys Leu Gln Phe Gly Pro
                405                 410                 415

Pro Ala Glu Gly Glu Val Val Gln Val Arg Trp Thr Asp Gly Gln Val
                420                 425                 430

Tyr Gly Ala Lys Phe Val Ala Ser His Pro Ile Gln Met Tyr Gln Val
                435                 440                 445

Glu Phe Glu Asp Gly Ser Gln Leu Val Val Lys Arg Asp Asp Val Tyr
450                 455                 460

Thr Leu Asp Glu Glu Leu Pro Lys Arg Val Lys Ser Arg Leu Ser Val
465                 470                 475                 480

Ala Ser Asp Met Arg Phe Asn Glu Ile Phe Thr Glu Lys Glu Val Lys
                485                 490                 495

Gln Glu Lys Lys Arg Gln Arg Val Ile Asn Ser
                500                 505

<210> SEQ ID NO 42
<211> LENGTH: 1524
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: nucleic acid dTLM

<400> SEQUENCE: 42
atgtccccta ctactaggtta ttggaaaatt aagggccttg tgcaacccac tcgacttctt     60
ttggaatatc ttgaagaaaa atatgaagag catttgtatg agcgcgatga aggtgataaa    120
tggcgaaaca aaaagtttga attgggtttg gagtttccca atcttcctta ttatattgat    180
ggtgatgtta aattaacaca gtctatggcc atcatacgtt atagctga caagcacaac    240 atgttgggtg ttgtccaaa agagcgtgca gagatttcaa tgcttgaagg agcggtttg    300
```

```
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600
tggcctttgc agggctggca agccacgttt ggtggtggcg accatcctcc aaaatcggat    660
ctggaagttc tgttccaggg gcccctggga tccactgcct tccatgtgag ctgcgcccag    720
gctgccggtg tgatgatgca gcctgacgac tggccttttg tggtcttcat tacctgcttt    780
cggcacaaga ttcctaattt ggagcgtgcc aaggggggcct tgcaaagcat cactgcaggc    840
cagaaagtca ttagcaagca taagaacggg cgcttctacc agtgtgaagt ggtcaggctc    900
accaccgaga ccttctatga agtcaacttt gatgatggc ccttcagcga caatctttat    960
cctgaggaca tagtgagcca ggactgtctc cagtttggtc ctcctgctga agggaagtg    1020
gtccaagtga gatggacaga cggccaagtc tatggagcca gtttgtggc ctcccaccct    1080
atccaaatgt accaggtgga gtttgaggat ggctcacaac ttgtggttaa gagagatgat    1140
gtatacacac tggatgaaga gcttcccaag agagtcaaat ctagactgtc agtagcctca    1200
gacatgcgct tcaatgagat tttcacagag aaagaggtta gcaagaaaa gaaacggcaa    1260
cgagttatca actcatctag cggcaatagt aacgctaaca gccgcgggcc gagcttcagc    1320
agcggcctgg tgccgttaag cttgcgcggc agccatgtgt tcgaggtgga aagatcctg    1380
gacatgaaga ccgaggggggg taaagttctt tacaaagttc gctggaaagg ctatacatcg    1440
gatgatgata cctgggagcc cgagattcac ctggaggact gtaaagaagt gcttcttgaa    1500
tttaggaaga aaattgcaga gtga                                          1524
```

<210> SEQ ID NO 43
<211> LENGTH: 507
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein dTLM

<400> SEQUENCE: 43

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125
```

```
Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
210                 215                 220

Phe Gln Gly Pro Leu Gly Ser Thr Ala Phe His Val Ser Cys Ala Gln
225                 230                 235                 240

Ala Ala Gly Val Met Met Gln Pro Asp Asp Trp Pro Phe Val Val Phe
                245                 250                 255

Ile Thr Cys Phe Arg His Lys Ile Pro Asn Leu Glu Arg Ala Lys Gly
            260                 265                 270

Ala Leu Gln Ser Ile Thr Ala Gly Gln Lys Val Ile Ser Lys His Lys
        275                 280                 285

Asn Gly Arg Phe Tyr Gln Cys Glu Val Val Arg Leu Thr Thr Glu Thr
290                 295                 300

Phe Tyr Glu Val Asn Phe Asp Asp Gly Ser Phe Ser Asp Asn Leu Tyr
305                 310                 315                 320

Pro Glu Asp Ile Val Ser Gln Asp Cys Leu Gln Phe Gly Pro Pro Ala
                325                 330                 335

Glu Gly Glu Val Val Gln Val Arg Trp Thr Asp Gly Gln Val Tyr Gly
            340                 345                 350

Ala Lys Phe Val Ala Ser His Pro Ile Gln Met Tyr Gln Val Glu Phe
        355                 360                 365

Glu Asp Gly Ser Gln Leu Val Val Lys Arg Asp Asp Val Tyr Thr Leu
370                 375                 380

Asp Glu Glu Leu Pro Lys Arg Val Lys Ser Arg Leu Ser Val Ala Ser
385                 390                 395                 400

Asp Met Arg Phe Asn Glu Ile Phe Thr Glu Lys Glu Val Lys Gln Glu
                405                 410                 415

Lys Lys Arg Gln Arg Val Ile Asn Ser Ser Gly Asn Ser Asn Ala
            420                 425                 430

Asn Ser Arg Gly Pro Ser Phe Ser Gly Leu Val Pro Leu Ser Leu
        435                 440                 445

Arg Gly Ser His Val Phe Glu Val Glu Lys Ile Leu Asp Met Lys Thr
450                 455                 460

Glu Gly Gly Lys Val Leu Tyr Lys Val Arg Trp Lys Gly Tyr Thr Ser
465                 470                 475                 480

Asp Asp Asp Thr Trp Glu Pro Glu Ile His Leu Glu Asp Cys Lys Glu
                485                 490                 495

Val Leu Leu Glu Phe Arg Lys Lys Ile Ala Glu
            500                 505
```

<210> SEQ ID NO 44
<211> LENGTH: 1290
<212> TYPE: DNA
<213> ORGANISM: Artificial Sequence
<220> FEATURE:
<223> OTHER INFORMATION: Description of Artificial Sequence: Synthetic -continued

```
            polynucleotide
<220> FEATURE:
<223> OTHER INFORMATION: nucleic acid PC7

<400> SEQUENCE: 44 atgtcccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg gttgtccaaa agagcgtgca gagatttcaa tgcttgaagg agcggttttg     300
gatattagat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgttttaaa     540
aaacgtattg aagctatccc acaaattgat aagtacttga atccagcaa gtatatagca     600 tggcctttgc agggctggca agccacgttt ggtggtggcg accatcctcc aaaatcggat     660
ctggaagttc tgttccaggg gcccctggga tccgagtatg aggatggccg gggctttggc     720
attggagagc tggtgtgggg gaaacttcgg ggcttctcct ggtggccagg ccgaattgtg     780
tcttggtgga tgacaggccg gagccgagca gctgaaggca ctcgctgggt catgtggttc     840
ggagatggca agttctcagt ggtgtgtgtg gagaagctca tgccgctgag ctccttctgc     900
agtgcattcc accaggccac ctacaacaag cagcccatgt accgcaaagc catctacgaa     960
gtcctccagg tggccagcag ccgtgccggg aagctgtttc agcttgccca tgacagtgat    1020
gaaagtgaca gtggcaaggc tgtggaagtg cagaacaagc agatgattga atgggccctc    1080
ggtggcttcc agccctcggg tcctaagggc ctggagccac cagagcaggt gttcgccgtg    1140
gagagcatcc ggaagaagcg cgtgcggaag ggtaaagtcg agtatctggt gaagtggaaa    1200
ggatggcccc caaagtacag cacgtgggag ccagaagagc acatcttgga cccccgcctc    1260
gtcatggcct acgaggagaa ggaggagtga                                     1290
```

```
<210> SEQ ID NO 45
<211> LENGTH: 429
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein PC7

<400> SEQUENCE: 45
```

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu

Gly Ala Val Leu Asp Ile Arg Tyr Gly Val Ser Arg Ile Ala Tyr Ser
                85                  90                  95

Lys Asp Phe Glu Thr Leu Lys Val Asp Phe Leu Ser Lys Leu Pro Glu
            100                 105                 110

Met Leu Lys Met Phe Glu Asp Arg Leu Cys His Lys Thr Tyr Leu Asn
        115                 120                 125

Gly Asp His Val Thr His Pro Asp Phe Met Leu Tyr Asp Ala Leu Asp
130                 135                 140

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
    210                 215                 220

Phe Gln Gly Pro Leu Gly Ser Glu Tyr Glu Asp Gly Arg Gly Phe Gly
225                 230                 235                 240

Ile Gly Glu Leu Val Trp Gly Lys Leu Arg Gly Phe Ser Trp Trp Pro
                245                 250                 255

Gly Arg Ile Val Ser Trp Trp Met Thr Gly Arg Ser Arg Ala Ala Glu
            260                 265                 270

Gly Thr Arg Trp Val Met Trp Phe Gly Asp Gly Lys Phe Ser Val Val
        275                 280                 285

Cys Val Glu Lys Leu Met Pro Leu Ser Ser Phe Cys Ser Ala Phe His
    290                 295                 300

Gln Ala Thr Tyr Asn Lys Gln Pro Met Tyr Arg Lys Ala Ile Tyr Glu
305                 310                 315                 320

Val Leu Gln Val Ala Ser Ser Arg Ala Gly Lys Leu Phe Pro Ala Cys
                325                 330                 335

His Asp Ser Asp Glu Ser Asp Ser Gly Lys Ala Val Glu Val Gln Asn
            340                 345                 350

Lys Gln Met Ile Glu Trp Ala Leu Gly Gly Phe Gln Pro Ser Gly Pro
        355                 360                 365

Lys Gly Leu Glu Pro Pro Glu Gln Val Phe Ala Val Glu Ser Ile Arg
    370                 375                 380

Lys Lys Arg Val Arg Lys Gly Lys Val Glu Tyr Leu Val Lys Trp Lys
385                 390                 395                 400

Gly Trp Pro Pro Lys Tyr Ser Thr Trp Glu Pro Glu His Ile Leu
                405                 410                 415

Asp Pro Arg Leu Val Met Ala Tyr Glu Glu Lys Glu Glu
            420                 425

<210> SEQ ID NO 46
<211> LENGTH: 1371
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: nucleic acid C7LP

<400> SEQUENCE: 46
atgtccccta tactaggtta ttggaaaatt aagggccttg tgcaacccac tcgacttctt    60

```
ttggaatatc ttgaagaaaa atatgaagag catttgtatg agcgcgatga aggtgataaa      120
tggcgaaaca aaaagtttga attgggtttg gagtttccca atcttcctta ttatattgat      180
ggtgatgtta aattaacaca gtctatggcc atcatacgtt atatagctga caagcacaac      240
atgttgggtg gttgtccaaa agagcgtgca gagatttcaa tgcttgaagg agcggttttg      300
gatattagat acggtgtttc gagaattgca tatagtaaag actttgaaac tctcaaagtt      360
gattttctta gcaagctacc tgaaatgctg aaaatgttcg aagatcgttt atgtcataaa      420
acatatttaa atggtgatca tgtaacccat cctgacttca tgttgtatga cgctcttgat      480
gttgttttat acatggaccc aatgtgcctg atgcgttcc caaaattagt ttgttttaaa       540
aaacgtattg aagctatccc acaaattgat aagtacttga atccagcaa gtatatagca       600
tggcctttgc agggctggca agccacgttt ggtggtggcg accatcctcc aaaatcggat      660
ctggaagttc tgttccaggg gcccctggga tccgagcagg tgttcgccgt ggagagcatc      720
cggaagaagc gcgtgcggaa gggtaaagtc gagtatctgg tgaagtggaa aggatggccc      780
ccaaagtaca gcacgtggga gccagaagag cacatcttgg accccgcct cgtcatggcc       840
tacgaggaga aggaggagtc tagcggcaat agtaacgcta acagccgcgg gccgagcttc      900
agcagcggcc tggtgccgtt aagcttgcgc ggcagccatg agtatgagga tggccggggc      960
tttggcattg agagctggt gtgggggaaa cttcggggct ctcctggtg gccaggccga       1020
attgtgtctt ggtggatgac aggccggagc cgagcagctg aaggcactcg ctgggtcatg     1080
tggttcggag atggcaagtt ctcagtggtg tgtgtggaga agctcatgcc gctgagctcc     1140
ttctgcagtg cattccacca ggccacctac aacaagcagc ccatgtaccg caaagccatc     1200
tacgaagtcc tccaggtggc cagcagccgt gccgggaagc tgtttccagc ttgccatgac     1260
agtgatgaaa gtgacagtgg caaggctgtg gaagtgcaga acaagcagat gattgaatgg     1320
gccctcggtg gcttccagcc ctcgggtcct aagggcctgg agccaccatg a              1371
```

<210> SEQ ID NO 47
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein C7LP

<400> SEQUENCE: 47

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
    210                 215                 220

Phe Gln Gly Pro Leu Gly Ser Glu Gln Val Phe Ala Val Glu Ser Ile
225                 230                 235                 240

Arg Lys Lys Arg Val Arg Lys Gly Lys Val Glu Tyr Leu Val Lys Trp
                245                 250                 255

Lys Gly Trp Pro Pro Lys Tyr Ser Thr Trp Glu Pro Glu Glu His Ile
            260                 265                 270

Leu Asp Pro Arg Leu Val Met Ala Tyr Glu Glu Lys Glu Glu Ser Ser
        275                 280                 285

Gly Asn Ser Asn Ala Asn Ser Arg Gly Pro Ser Phe Ser Ser Gly Leu
    290                 295                 300

Val Pro Leu Ser Leu Arg Gly Ser His Glu Tyr Glu Asp Gly Arg Gly
305                 310                 315                 320

Phe Gly Ile Gly Glu Leu Val Trp Gly Lys Leu Arg Gly Phe Ser Trp
                325                 330                 335

Trp Pro Gly Arg Ile Val Ser Trp Trp Met Thr Gly Arg Ser Arg Ala
            340                 345                 350

Ala Glu Gly Thr Arg Trp Val Met Trp Phe Gly Asp Gly Lys Phe Ser
        355                 360                 365

Val Val Cys Val Glu Lys Leu Met Pro Leu Ser Ser Phe Cys Ser Ala
370                 375                 380

Phe His Gln Ala Thr Tyr Asn Lys Gln Pro Met Tyr Arg Lys Ala Ile
385                 390                 395                 400

Tyr Glu Val Leu Gln Val Ala Ser Ser Arg Ala Gly Lys Leu Phe Pro
                405                 410                 415

Ala Cys His Asp Ser Asp Glu Ser Asp Ser Gly Lys Ala Val Glu Val
            420                 425                 430

Gln Asn Lys Gln Met Ile Glu Trp Ala Leu Gly Gly Phe Gln Pro Ser
        435                 440                 445

Gly Pro Lys Gly Leu Glu Pro Pro
450                 455

<210> SEQ ID NO 48
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: nucleic acid C7LM

<400> SEQUENCE: 48

```
atgtccccta tactaggtta ttggaaaatt aagggccttg tgcaacccac tcgacttctt    60
ttggaatatc ttgaagaaaa atatgaagag catttgtatg agcgcgatga aggtgataaa   120
tggcgaaaca aaaagtttga attgggtttg agtttcccca atcttcctta ttatattgat   180
ggtgatgtta aattaacaca gtctatggcc atcatacgtt atatagctga caagcacaac   240
atgttgggtg gttgtccaaa agagcgtgca gagatttcaa tgcttgaagg agcggttttg   300
gatattagat acggtgtttc gagaattgca tatagtaaag actttgaaac tctcaaagtt   360
gattttctta gcaagctacc tgaaatgctg aaaatgttcg aagatcgttt atgtcataaa   420
acatatttaa atggtgatca tgtaacccat cctgacttca tgttgtatga cgctcttgat   480
gttgttttat acatggaccc aatgtgcctg gatgcgttcc caaaattagt ttgttttaaa   540
aaacgtattg aagctatccc acaaattgat aagtacttga atccagcaa gtatatagca   600
tggcctttgc agggctggca agccacgttt ggtggtggcg accatcctcc aaaatcggat   660
ctggaagttc tgttccaggg gcccctggga tccgagcagg tgttcgccgt ggagagcatc   720
cggaagaagc gcgtgcggaa gggtaaagtc gagtatctgg tgaagtggaa aggatggccc   780
ccaaagtaca gcacgtggga ccagaagag cacatcttgg accccgcct cgtcatggcc   840
tacgaggaga aggaggagtc tagcggcaat agtaacgcta acagccgcgg gccgagcttc   900
agcagcggcc tggtgccgtt aagcttgcgc ggcagccatg tgttcgaggt ggagaagatc   960
ctggacatga agaccgaggg gggtaaagtt ctttacaaag ttcgctggaa aggctataca  1020
tcggatgatg atacctggga gcccgagatt cacctggagg actgtaaaga agtgcttctt  1080
gaatttagga agaaaattgc agagtga                                     1107
```

<210> SEQ ID NO 49
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein C7LM

<400> SEQUENCE: 49

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp

```
            145                 150                 155                 160
Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
                195                 200                 205

Thr Phe Gly Gly Gly Asp His Pro Pro Lys Ser Asp Leu Glu Val Leu
    210                 215                 220

Phe Gln Gly Pro Leu Gly Ser Glu Gln Val Phe Ala Val Glu Ser Ile
225                 230                 235                 240

Arg Lys Lys Arg Val Arg Lys Gly Lys Val Glu Tyr Leu Val Lys Trp
                245                 250                 255

Lys Gly Trp Pro Pro Lys Tyr Ser Thr Trp Glu Pro Glu Glu His Ile
                260                 265                 270

Leu Asp Pro Arg Leu Val Met Ala Tyr Glu Glu Lys Glu Glu Ser Ser
            275                 280                 285

Gly Asn Ser Asn Ala Asn Ser Arg Gly Pro Ser Phe Ser Ser Gly Leu
        290                 295                 300

Val Pro Leu Ser Leu Arg Gly Ser His Val Phe Glu Val Glu Lys Ile
305                 310                 315                 320

Leu Asp Met Lys Thr Glu Gly Gly Lys Val Leu Tyr Lys Val Arg Trp
                325                 330                 335

Lys Gly Tyr Thr Ser Asp Asp Asp Thr Trp Glu Pro Glu Ile His Leu
            340                 345                 350

Glu Asp Cys Lys Glu Val Leu Leu Glu Phe Arg Lys Lys Ile Ala Glu
            355                 360                 365

<210> SEQ ID NO 50
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: nucleic acid MLC7

<400> SEQUENCE: 50
atgtccccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg gttgtccaaa agagcgtgca gagatttcaa tgcttgaagg agcggttttg     300
gatattagat acgtgttttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg atgcgttcc caaaattagt tgtgttttaaa     540 aaacgtattg aagctatccc acaaattgat aagtacttga atccagcaa gtatatagca     600 tggcctttgc agggctggca agccacgttt ggtggtggcg accatcctcc aaaatcggat     660
ctggaagttc tgttccaggg gcccctggga tccgtgttcg aggtggagaa gatcctggac     720
atgaagaccg agggggtaa agttctttac aaagttcgct ggaaaggcta tacatcggat     780
```

-continued

```
gatgatacct gggagcccga gattcacctg gaggactgta aagaagtgct tcttgaattt    840
aggaagaaaa ttgcagagtc tagcggcaat agtaacgcta cagccgcgg gccgagcttc     900 agcagcggcc tggtgccgtt aagcttgcgc ggcagccatg agcaggtgtt cgccgtggag    960
agcatccgga gaagcgcgt gcggaagggt aaagtcgagt atctggtgaa gtggaaagga   1020
tggcccccaa agtacagcac gtgggagcca agagcacac tcttggaccc ccgcctcgtc   1080
atggcctacg aggagaagga ggagtga                                       1107
```

<210> SEQ ID NO 51
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein MLC7

<400> SEQUENCE: 51

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Glu Val Leu
    210                 215                 220

Phe Gln Gly Pro Leu Gly Ser Val Phe Glu Val Glu Lys Ile Leu Asp
225                 230                 235                 240

Met Lys Thr Glu Gly Gly Lys Val Leu Tyr Lys Val Arg Trp Lys Gly
                245                 250                 255

Tyr Thr Ser Asp Asp Asp Thr Trp Glu Pro Glu Ile His Leu Glu Asp
            260                 265                 270

Cys Lys Glu Val Leu Leu Glu Phe Arg Lys Lys Ile Ala Glu Ser Ser
        275                 280                 285
```

Gly Asn Ser Asn Ala Asn Ser Arg Gly Pro Ser Phe Ser Ser Gly Leu
        290                 295                 300

Val Pro Leu Ser Leu Arg Gly Ser His Glu Gln Val Phe Ala Val Glu
305                 310                 315                 320

Ser Ile Arg Lys Lys Arg Val Arg Lys Gly Lys Val Glu Tyr Leu Val
                325                 330                 335

Lys Trp Lys Gly Trp Pro Pro Lys Tyr Ser Thr Trp Glu Pro Glu Glu
                340                 345                 350

His Ile Leu Asp Pro Arg Leu Val Met Ala Tyr Glu Glu Lys Glu Glu
                355                 360                 365

<210> SEQ ID NO 52
<211> LENGTH: 1164
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: nucleic acid TLC7

<400> SEQUENCE: 52
atgtccccta tactaggtta ttggaaaatt aagggccttg tgcaacccac tcgacttctt     60
ttggaatatc ttgaagaaaa atatgaagag catttgtatg agcgcgatga aggtgataaa    120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg gttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aaaatcggat    660
ctggaagttc tgttccaggg gcccctggga tccgtgatcc gagatgagtg gggcaatcag    720
atctggatct gccctgggtg taacaagcct gacgatggga gtcccatgat tgggtgtgac    780
gactgcgatg actggtacca ctggccctgt gttggaatca tgactgcacc cccagaagag    840
atgcagtggt tctgccccaa gtgtgcgaac aagaagaagg acaaaaagca caagaagagg    900
aagcatcgag cccactctag cggcaatagt aacgctaaca gccgcgggcc gagcttcagc    960
agcggcctgg tgccgttaag cttgcgcggc agccatgagc aggtgttcgc cgtggagagc   1020
atccggaaga agcgcgtgcg gaagggtaaa gtcgagtatc tggtgaagtg gaaaggatgg   1080 ccccaaagt acagcacgtg ggagccagaa gagcacatct ggaccccgc cctcgtcatg   1140 gcctacgagg agaaggagga gtga                                         1164

<210> SEQ ID NO 53
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein TLC7

<400> SEQUENCE: 53

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
    210                 215                 220

Phe Gln Gly Pro Leu Gly Ser Val Ile Arg Asp Glu Trp Gly Asn Gln
225                 230                 235                 240

Ile Trp Ile Cys Pro Gly Cys Asn Lys Pro Asp Asp Gly Ser Pro Met
                245                 250                 255

Ile Gly Cys Asp Asp Cys Asp Asp Trp Tyr His Trp Pro Cys Val Gly
            260                 265                 270

Ile Met Thr Ala Pro Pro Glu Glu Met Gln Trp Phe Cys Pro Lys Cys
        275                 280                 285

Ala Asn Lys Lys Asp Lys Lys His Lys Lys Arg Lys His Arg Ala
    290                 295                 300

His Ser Ser Gly Asn Ser Asn Ala Asn Ser Arg Gly Pro Ser Phe Ser
305                 310                 315                 320

Ser Gly Leu Val Pro Leu Ser Leu Arg Gly Ser His Glu Gln Val Phe
                325                 330                 335

Ala Val Glu Ser Ile Arg Lys Lys Arg Val Arg Lys Gly Lys Val Glu
            340                 345                 350

Tyr Leu Val Lys Trp Lys Gly Trp Pro Pro Lys Tyr Ser Thr Trp Glu
        355                 360                 365

Pro Glu Glu His Ile Leu Asp Pro Arg Leu Val Met Ala Tyr Glu Glu
    370                 375                 380

Lys Glu Glu
385
```

<210> SEQ ID NO 54
<211> LENGTH: 1530
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: nucleic acid PA

<400> SEQUENCE: 54

```
atgtccccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg ttgtccaaa agagcgtgca gagatttcaa tgcttgaagg agcggttttg     300
gatattagat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg atgcgttcc caaaattagt ttgttttaaa      540
aaacgtattg aagctatccc acaaattgat aagtacttga atccagcaa gtatatagca     600
tggcctttgc agggctggca agccacgttt ggtggtggcg accatcctcc aaaatcggat     660
ctggaagttc tgttccaggg gcccctggga tccgagtatg aggatggccg gggctttggc     720
attggagagc tggtgtgggg gaaacttcgg ggcttctcct ggtggccagg ccgaattgtg     780
tcttggtgga tgacaggccg gagccgagca gctgaaggca ctcgctgggt catgtggttc     840
ggagatggca agttctcagt ggtgtgtgtg agaagctca tgccgctgag ctccttctgc     900
agtgcattcc accaggccac ctacaacaag cagcccatgt accgcaaagc catctacgaa     960
gtcctccagg tggccagcag ccgtgccggg aagctgtttc agcttgcca tgacagtgat    1020
gaaagtgaca gtggcaaggc tgtggaagtg cagaacaagc agatgattga atgggccctc    1080
ggtggcttcc agccctcggg tcctaagggc ctggagccac acatatggga agatgggctt    1140
catgggattg tgagctgcac tgcttgtgga caacaggtca atcattttca aaaagattcc    1200
atttatagac cccttcatt gcaagttctt atttgtaaga attgctttaa gtattacatg    1260
agtgatgata ttagccgtga ctcagatgga atggatgaac aatgtaggtg gtgtgcggaa    1320
ggtgaaaact tgatttgttg tgacttttgc cataatgctt tctgcaagaa atgcattcta    1380
cgcaaccttg gtcgaaagga gttgtccaca ataatggatg aaaacaacca atggtattgc    1440
tacatttgtc acccagagcc tttgttggac ttggtcactg catgtaacag cgtatttgag    1500
aatttagaac agttgttgca gctcgactga                                    1530
```

<210> SEQ ID NO 55
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein PA

<400> SEQUENCE: 55

```
Met Ser Pro Ile Leu Gly Tyr Trp Lys Ile Lys Gly Leu Val Gln Pro
1               5                   10                  15
```

```
Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
210                 215                 220

Phe Gln Gly Pro Leu Gly Ser Glu Tyr Glu Asp Gly Arg Gly Phe Gly
225                 230                 235                 240

Ile Gly Glu Leu Val Trp Gly Lys Leu Arg Gly Phe Ser Trp Trp Pro
                245                 250                 255

Gly Arg Ile Val Ser Trp Trp Met Thr Gly Arg Ser Arg Ala Ala Glu
            260                 265                 270

Gly Thr Arg Trp Val Met Trp Phe Gly Asp Gly Lys Phe Ser Val Val
        275                 280                 285

Cys Val Glu Lys Leu Met Pro Leu Ser Ser Phe Cys Ser Ala Phe His
290                 295                 300

Gln Ala Thr Tyr Asn Lys Gln Pro Met Tyr Arg Lys Ala Ile Tyr Glu
305                 310                 315                 320

Val Leu Gln Val Ala Ser Ser Arg Ala Gly Lys Leu Phe Pro Ala Cys
                325                 330                 335

His Asp Ser Asp Glu Ser Asp Ser Gly Lys Ala Val Glu Val Gln Asn
            340                 345                 350

Lys Gln Met Ile Glu Trp Ala Leu Gly Gly Phe Gln Pro Ser Gly Pro
        355                 360                 365

Lys Gly Leu Glu Pro Pro His Met Glu Asp Gly Leu His Gly Ile Val
370                 375                 380

Ser Cys Thr Ala Cys Gly Gln Gln Val Asn His Phe Gln Lys Asp Ser
385                 390                 395                 400

Ile Tyr Arg His Pro Ser Leu Gln Val Leu Ile Cys Lys Asn Cys Phe
                405                 410                 415

Lys Tyr Tyr Met Ser Asp Asp Ile Ser Arg Asp Ser Asp Gly Met Asp
            420                 425                 430
```

Glu Gln Cys Arg Trp Cys Ala Glu Gly Gly Asn Leu Ile Cys Cys Asp
            435                 440                 445

Phe Cys His Asn Ala Phe Cys Lys Lys Cys Ile Leu Arg Asn Leu Gly
        450                 455                 460

Arg Lys Glu Leu Ser Thr Ile Met Asp Glu Asn Asn Gln Trp Tyr Cys
465                 470                 475                 480

Tyr Ile Cys His Pro Glu Pro Leu Leu Asp Leu Val Thr Ala Cys Asn
                485                 490                 495

Ser Val Phe Glu Asn Leu Glu Gln Leu Leu Gln Leu Asp
            500                 505

<210> SEQ ID NO 56
<211> LENGTH: 1611
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: nucleic acid PLA

<400> SEQUENCE: 56

```
atgtcccctg tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg gttgtccaaa agagcgtgca gagatttcaa tgcttgaagg agcggtttg      300 gatattagat acgtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgttttaaa     540
aaacgtattg aagctatccc acaaattgat aagtacttga atccagcaa gtatatagca      600 tggcctttgc agggctggca agccacgttt ggtggtggcg accatcctcc aaaatcggat     660
ctggaagttc tgttccaggg gcccctggga tccgagtatg aggatggccg gggctttggc     720
attggagagc tggtgtgggg gaaacttcgg ggcttctcct ggtggccagg ccgaattgtg     780
tcttggtgga tgacaggccg gagccgagca gctgaaggca ctcgctgggt catgtggttc     840
ggagatggca gttctcagt ggtgtgtgtg gagaagctca tgccgctgag ctccttctgc      900
agtgcattcc accaggccac ctacaacaag cagcccatgt accgcaaagc catctacgaa     960
gtcctccagg tggccagcag ccgtgccggg aagctgtttc agcttgcca tgacagtgat     1020 gaaagtgaca gtggcaaggc tgtggaagtg cagaacaagc agatgattga atgggccctc     1080
ggtggcttcc agccctcggg tcctaagggc ctggagccac atctagcgg caatagtaac      1140 gctaacagcc gcgggccgag cttcagcagc ggcctggtgc cgttaagctt gcgcggcagc     1200
catcatatgg aagatgggct tcatgggatt gtgagctgca ctgcttgtgg acaacaggtc     1260
aatcattttc aaaagattc catttataga caccttcat tgcaagttct tatttgtaag      1320
aattgcttta gtattacat gagtgatgat attagccgtg actcagatgg aatggatgaa     1380
caatgtaggt ggtgtgcgga aggtggaaac ttgatttgtt gtgactttgt ccataatgct     1440
ttctgcaaga aatgcattct acgcaacctt ggtcgaaagg agttgtccac aataatggat     1500
gaaaacaacc aatggtattg ctacatttgt cacccagagc cttgttggta cttggtcact     1560
```
gcatgtaaca gcgtatttga gaatttagaa cagttgttgc agctcgactg a                1611

<210> SEQ ID NO 57
<211> LENGTH: 536
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein PLA

<400> SEQUENCE: 57

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
    210                 215                 220

Phe Gln Gly Pro Leu Gly Ser Glu Tyr Glu Asp Gly Arg Gly Phe Gly
225                 230                 235                 240

Ile Gly Glu Leu Val Trp Gly Lys Leu Arg Gly Phe Ser Trp Trp Pro
                245                 250                 255

Gly Arg Ile Val Ser Trp Trp Met Thr Gly Arg Ser Arg Ala Ala Glu
            260                 265                 270

Gly Thr Arg Trp Val Met Trp Phe Gly Asp Gly Lys Phe Ser Val Val
        275                 280                 285

Cys Val Glu Lys Leu Met Pro Leu Ser Ser Phe Cys Ser Ala Phe His
    290                 295                 300

Gln Ala Thr Tyr Asn Lys Gln Pro Met Tyr Arg Lys Ala Ile Tyr Glu
305                 310                 315                 320

Val Leu Gln Val Ala Ser Ser Arg Ala Gly Lys Leu Phe Pro Ala Cys
                325                 330                 335
```

```
His Asp Ser Asp Glu Ser Asp Ser Gly Lys Ala Val Glu Val Gln Asn
            340                 345                 350

Lys Gln Met Ile Glu Trp Ala Leu Gly Gly Phe Gln Pro Ser Gly Pro
        355                 360                 365

Lys Gly Leu Glu Pro Pro Ser Ser Gly Asn Ser Asn Ala Asn Ser Arg
    370                 375                 380

Gly Pro Ser Phe Ser Ser Gly Leu Val Pro Leu Ser Leu Arg Gly Ser
385                 390                 395                 400

His His Met Glu Asp Gly Leu His Gly Ile Val Ser Cys Thr Ala Cys
                405                 410                 415

Gly Gln Gln Val Asn His Phe Gln Lys Asp Ser Ile Tyr Arg His Pro
            420                 425                 430

Ser Leu Gln Val Leu Ile Cys Lys Asn Cys Phe Lys Tyr Tyr Met Ser
        435                 440                 445

Asp Asp Ile Ser Arg Asp Ser Asp Gly Met Asp Glu Gln Cys Arg Trp
    450                 455                 460

Cys Ala Glu Gly Gly Asn Leu Ile Cys Cys Asp Phe Cys His Asn Ala
465                 470                 475                 480

Phe Cys Lys Lys Cys Ile Leu Arg Asn Leu Gly Arg Lys Glu Leu Ser
                485                 490                 495

Thr Ile Met Asp Glu Asn Asn Gln Trp Tyr Cys Tyr Ile Cys His Pro
            500                 505                 510

Glu Pro Leu Leu Asp Leu Val Thr Ala Cys Asn Ser Val Phe Glu Asn
        515                 520                 525

Leu Glu Gln Leu Leu Gln Leu Asp
    530                 535

<210> SEQ ID NO 58
<211> LENGTH: 1611
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: nucleic acid ALP

<400> SEQUENCE: 58
atgtccccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg ttgtccaaa agagcgtgca gagatttcaa tgcttgaagg agcggttttg     300
gatattagat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgttttaaa     540
aaacgtattg aagctatccc acaaattgat aagtacttga atccagcaa gtatatagca     600 tggcctttgc agggctggca agccacgttt ggtggtggcg accatcctcc aaaatcggat     660
ctggaagttc tgttccaggg gccctggga tcccatatgg aagatgggct tcatgggatt     720
gtgagctgca ctgcttgtgg acaacaggtc aatcattttc aaaagattc catttataga     780 caccctttcat tgcaagttct tatttgtaag aattgcttta gtattacat gagtgatgat     840
```

```
attagccgtg actcagatgg aatggatgaa caatgtaggt ggtgtgcgga aggtggaaac    900
ttgatttgtt gtgactttg ccataatgct ttctgcaaga aatgcattct acgcaacctt    960
ggtcgaaagg agttgtccac aataatggat gaaacaacc aatggtattg ctacatttgt   1020
cacccagagc ctttgttgga cttggtcact gcatgtaaca gcgtatttga gaatttagaa   1080
cagttgttgc agctcgactc tagcggcaat agtaacgcta acagccgcgg gccgagcttc   1140
agcagcggcc tggtgccgtt aagcttgcgc ggcagccatg agtatgagga tggccggggc   1200
tttggcattg agagctggt gtggggggaaa cttcggggct tctcctggtg gccaggccga   1260
attgtgtctt ggtggatgac aggccggagc cgagcagctg aaggcactcg ctgggtcatg   1320
tggttcggag atggcaagtt ctcagtggtg tgtgtggaga agctcatgcc gctgagctcc   1380
ttctgcagtg cattccacca ggccacctac aacaagcagc ccatgtaccg caaagccatc   1440
tacgaagtcc tccaggtggc cagcagccgt gccgggaagc tgtttccagc ttgccatgac   1500
agtgatgaaa gtgacagtgg caaggctgtg gaagtcagac aaagcagat gattgaatgg   1560 gccctcggtg gcttccagcc ctcgggtcct aagggcctgg agccaccatg a         1611
```

<210> SEQ ID NO 59
<211> LENGTH: 536
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein ALP

<400> SEQUENCE: 59

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205
```

```
Thr Phe Gly Gly Gly Asp His Pro Pro Lys Ser Asp Leu Glu Val Leu
    210                 215                 220
Phe Gln Gly Pro Leu Gly Ser His Met Glu Asp Gly Leu His Gly Ile
225                 230                 235                 240
Val Ser Cys Thr Ala Cys Gly Gln Gln Val Asn His Phe Gln Lys Asp
                245                 250                 255
Ser Ile Tyr Arg His Pro Ser Leu Gln Val Leu Ile Cys Lys Asn Cys
            260                 265                 270
Phe Lys Tyr Tyr Met Ser Asp Asp Ile Ser Arg Asp Ser Asp Gly Met
        275                 280                 285
Asp Glu Gln Cys Arg Trp Cys Ala Glu Gly Gly Asn Leu Ile Cys Cys
290                 295                 300
Asp Phe Cys His Asn Ala Phe Cys Lys Lys Cys Ile Leu Arg Asn Leu
305                 310                 315                 320
Gly Arg Lys Glu Leu Ser Thr Ile Met Asp Glu Asn Asn Gln Trp Tyr
                325                 330                 335
Cys Tyr Ile Cys His Pro Glu Pro Leu Leu Asp Leu Val Thr Ala Cys
            340                 345                 350
Asn Ser Val Phe Glu Asn Leu Glu Gln Leu Leu Gln Leu Asp Ser Ser
        355                 360                 365
Gly Asn Ser Asn Ala Asn Ser Arg Gly Pro Ser Phe Ser Ser Gly Leu
370                 375                 380
Val Pro Leu Ser Leu Arg Gly Ser His Glu Tyr Glu Asp Gly Arg Gly
385                 390                 395                 400
Phe Gly Ile Gly Glu Leu Val Trp Gly Lys Leu Arg Gly Phe Ser Trp
                405                 410                 415
Trp Pro Gly Arg Ile Val Ser Trp Trp Met Thr Gly Arg Ser Arg Ala
            420                 425                 430
Ala Glu Gly Thr Arg Trp Val Met Trp Phe Gly Asp Gly Lys Phe Ser
        435                 440                 445
Val Val Cys Val Glu Lys Leu Met Pro Leu Ser Ser Phe Cys Ser Ala
450                 455                 460
Phe His Gln Ala Thr Tyr Asn Lys Gln Pro Met Tyr Arg Lys Ala Ile
465                 470                 475                 480
Tyr Glu Val Leu Gln Val Ala Ser Ser Arg Ala Gly Lys Leu Phe Pro
                485                 490                 495
Ala Cys His Asp Ser Asp Glu Ser Asp Ser Gly Lys Ala Val Glu Val
            500                 505                 510
Gln Asn Lys Gln Met Ile Glu Trp Ala Leu Gly Gly Phe Gln Pro Ser
        515                 520                 525
Gly Pro Lys Gly Leu Glu Pro Pro
530                 535

<210> SEQ ID NO 60
<211> LENGTH: 1428
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: nucleic acid TLP

<400> SEQUENCE: 60
atgtccccta tactaggtta ttggaaaatt aagggccttg tgcaacccac tcgacttctt      60
ttggaatatc ttgaagaaaa atatgaagag catttgtatg agcgcgatga aggtgataaa     120
```

```
tggcgaaaca aaaagtttga attgggtttg gagtttccca atcttcctta ttatattgat      180
ggtgatgtta aattaacaca gtctatggcc atcatacgtt atatagctga caagcacaac      240
atgttgggtg ttgtccaaa agagcgtgca gagatttcaa tgcttgaagg agcggttttg       300
gatattagat acggtgtttc gagaattgca tatagtaaag actttgaaac tctcaaagtt      360
gattttctta gcaagctacc tgaaatgctg aaaatgttcg aagatcgttt atgtcataaa      420
acatatttaa atggtgatca tgtaacccat cctgacttca tgttgtatga cgctcttgat      480
gttgttttat acatggaccc aatgtgcctg gatgcgttcc caaaattagt ttgttttaaa      540
aaacgtattg aagctatccc acaaattgat aagtacttga atccagcaa gtatatagca       600 tggcctttgc agggctggca agccacgttt ggtggtggcg accatcctcc aaaatcggat      660
ctggaagttc tgttccaggg gcccctggga tccgtgatcc gagatgagtg gggcaatcag      720
atctggatct gccctgggtg taacaagcct gacgatggga gtcccatgat tgggtgtgac      780
gactgcgatg actggtacca ctggccctgt gttggaatca tgactgcacc cccagaagag      840
atgcagtggt tctgccccaa gtgtgcgaac aagaagaagg acaaaaagca caagaagagg      900
aagcatcgag cccactctag cggcaatagt aacgctaaca gccgcgggcc gagcttcagc      960
agcggcctgg tgccgttaag cttgcgcggc agccatgagt atgaggatgg ccggggctttt    1020 ggcattggag agctggtgtg ggggaaactt cggggcttct cctggtggcc aggccgaatt     1080
gtgtcttggt ggatgacagg ccggagccga gcagctgaag cactcgctg ggtcatgtgg      1140 ttcggagatg gcaagttctc agtggtgtgt gtggagaagc tcatgccgct gagctccttc     1200
tgcagtgcat ccaccaggc cacctacaac aagcagccca tgtaccgcaa agccatctac      1260
gaagtcctcc aggtggccag cagccgtgcc gggaagctgt ttccagcttg ccatgacagt     1320
gatgaaagtg acagtggcaa ggctgtggaa gtgcagaaca agcagatgat tgaatgggcc    1380
ctcggtggct tccagccctc gggtcctaag ggcctggagc caccatga                  1428
```

<210> SEQ ID NO 61
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein TLP

<400> SEQUENCE: 61

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
    210                 215                 220

Phe Gln Gly Pro Leu Gly Ser Val Ile Arg Asp Glu Trp Gly Asn Gln
225                 230                 235                 240

Ile Trp Ile Cys Pro Gly Cys Asn Lys Pro Asp Asp Gly Ser Pro Met
                245                 250                 255

Ile Gly Cys Asp Asp Cys Asp Asp Trp Tyr His Trp Pro Cys Val Gly
            260                 265                 270

Ile Met Thr Ala Pro Pro Glu Glu Met Gln Trp Phe Cys Pro Lys Cys
        275                 280                 285

Ala Asn Lys Lys Asp Lys Lys His Lys Lys Arg Lys His Arg Ala
    290                 295                 300

His Ser Ser Gly Asn Ser Asn Ala Asn Ser Arg Gly Pro Ser Phe Ser
305                 310                 315                 320

Ser Gly Leu Val Pro Leu Ser Leu Arg Gly Ser His Glu Tyr Glu Asp
                325                 330                 335

Gly Arg Gly Phe Gly Ile Gly Glu Leu Val Trp Gly Lys Leu Arg Gly
            340                 345                 350

Phe Ser Trp Trp Pro Gly Arg Ile Val Ser Trp Met Thr Gly Arg
        355                 360                 365

Ser Arg Ala Ala Glu Gly Thr Arg Trp Val Met Trp Phe Gly Asp Gly
370                 375                 380

Lys Phe Ser Val Val Cys Val Glu Lys Leu Met Pro Leu Ser Ser Phe
385                 390                 395                 400

Cys Ser Ala Phe His Gln Ala Thr Tyr Asn Lys Gln Pro Met Tyr Arg
            405                 410                 415

Lys Ala Ile Tyr Glu Val Leu Gln Val Ala Ser Ser Arg Ala Gly Lys
        420                 425                 430

Leu Phe Pro Ala Cys His Asp Ser Asp Glu Ser Asp Ser Gly Lys Ala
    435                 440                 445

Val Glu Val Gln Asn Lys Gln Met Ile Glu Trp Ala Leu Gly Gly Phe
450                 455                 460

Gln Pro Ser Gly Pro Lys Gly Leu Glu Pro Pro
465                 470                 475

<210> SEQ ID NO 62
<211> LENGTH: 1428
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: nucleic acid PLT

<400> SEQUENCE: 62

```
atgtcccta   tactaggtta   ttggaaaatt   aagggccttg   tgcaacccac   tcgacttctt     60
ttggaatatc  ttgaagaaaa   atatgaagag   catttgtatg   agcgcgatga   aggtgataaa    120
tggcgaaaca  aaaagtttga   attgggtttg   gagtttccca   atcttcctta   ttatattgat    180
ggtgatgtta  aattaacaca   gtctatggcc   atcatacgtt   atatagctga   caagcacaac    240
atgttgggtg  ttgtccaaa    agagcgtgca   gagatttcaa   tgcttgaagg   agcggttttg    300
gatattagat  acggtgtttc   gagaattgca   tatagtaaag   actttgaaac   tctcaaagtt    360
gattttctta  gcaagctacc   tgaaatgctg   aaaatgttcg   aagatcgttt   atgtcataaa    420
acatatttaa  atggtgatca   tgtaacccat   cctgacttca   tgttgtatga   cgctcttgat    480
gttgttttat  acatggaccc   aatgtgcctg   atgcgttcc    caaaattagt   ttgttttaaa    540
aaacgtattg  aagctatccc   acaaattgat   aagtacttga   atccagcaa    gtatatagca    600
tggcctttgc  agggctggca   agccacgttt   ggtggtggcg   accatcctcc   aaaatcggat    660
ctggaagttc  tgttccaggg   gcccctggga   tccgagtatg   aggatggccg   gggctttggc    720
attggagagc  tggtgtgggg   gaaacttcgg   ggcttctcct   ggtggccagg   ccgaattgtg    780
tcttggtgga  tgacaggccg   agccgagca   gctgaaggca   ctcgctgggt   catgtggttc    840
ggagatggca  agttctcagt   ggtgtgtgtg   gagaagctca   tgccgctgag   ctccttctgc    900
agtgcattcc  accaggccac   ctacaacaag   cagcccatgt   accgcaaagc   catctacgaa    960
gtcctccagg  tggccagcag   ccgtgccggg   aagctgtttc   cagcttgcca   tgacagtgat   1020
gaaagtgaca  gtgcaaggc    tgtggaagtg   cagaacaagc   agatgattga   atgggccctc   1080
ggtggcttcc  agcctcggg    tcctaaggc    ctggagccac   catctagcgg   caatagtaac   1140
gctaacagcc  gcgggccgag   cttcagcagc   ggcctggtgc   cgttaagctt   gcgcggcagc   1200
catgtgatcc  gagatgagtg   gggcaatcag   atctggatct   gccctgggtg   taacaagcct   1260
gacgatggga  gtcccatgat   tgggtgtgac   gactgcgatg   actggtacca   ctggccctgt   1320
gttggaatca  tgactgcacc   cccagaagag   atgcagtggt   tctgccccaa   gtgtgcgaac   1380
aagaagaagg  acaaaaagca   aagaagagg    aagcatcgag   cccactga                  1428
```

<210> SEQ ID NO 63
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein PLT

<400> SEQUENCE: 63

```
Met Ser Pro Ile Leu Gly Tyr Trp Lys Ile Lys Gly Leu Val Gln Pro
  1               5                  10                  15

Thr Arg Leu Leu Leu Glu Tyr Leu Glu Glu Lys Tyr Glu Glu His Leu
             20                  25                  30

Tyr Glu Arg Asp Glu Gly Asp Lys Trp Arg Asn Lys Lys Phe Glu Leu
         35                  40                  45

Gly Leu Glu Phe Pro Asn Leu Pro Tyr Tyr Ile Asp Gly Asp Val Lys
     50                  55                  60

Leu Thr Gln Ser Met Ala Ile Ile Arg Tyr Ile Ala Asp Lys His Asn
 65                  70                  75                  80
```

Met Leu Gly Gly Cys Pro Lys Glu Arg Ala Glu Ile Ser Met Leu Glu
            85                  90                  95

Gly Ala Val Leu Asp Ile Arg Tyr Gly Val Ser Arg Ile Ala Tyr Ser
        100                 105                 110

Lys Asp Phe Glu Thr Leu Lys Val Asp Phe Leu Ser Lys Leu Pro Glu
    115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Glu Val Leu
    210                 215                 220

Phe Gln Gly Pro Leu Gly Ser Glu Tyr Glu Asp Gly Arg Gly Phe Gly
225                 230                 235                 240

Ile Gly Glu Leu Val Trp Gly Lys Leu Arg Gly Phe Ser Trp Trp Pro
                245                 250                 255

Gly Arg Ile Val Ser Trp Trp Met Thr Gly Arg Ser Arg Ala Ala Glu
            260                 265                 270

Gly Thr Arg Trp Val Met Trp Phe Gly Asp Gly Lys Phe Ser Val Val
        275                 280                 285

Cys Val Glu Lys Leu Met Pro Leu Ser Ser Phe Cys Ser Ala Phe His
290                 295                 300

Gln Ala Thr Tyr Asn Lys Gln Pro Met Tyr Arg Lys Ala Ile Tyr Glu
305                 310                 315                 320

Val Leu Gln Val Ala Ser Ser Arg Ala Gly Lys Leu Phe Pro Ala Cys
                325                 330                 335

His Asp Ser Asp Glu Ser Asp Ser Gly Lys Ala Val Glu Val Gln Asn
            340                 345                 350

Lys Gln Met Ile Glu Trp Ala Leu Gly Gly Phe Gln Pro Ser Gly Pro
        355                 360                 365

Lys Gly Leu Glu Pro Pro Ser Ser Gly Asn Ser Asn Ala Asn Ser Arg
    370                 375                 380

Gly Pro Ser Phe Ser Ser Gly Leu Val Pro Leu Ser Leu Arg Gly Ser
385                 390                 395                 400

His Val Ile Arg Asp Glu Trp Gly Asn Gln Ile Trp Ile Cys Pro Gly
                405                 410                 415

Cys Asn Lys Pro Asp Asp Gly Ser Pro Met Ile Gly Cys Asp Asp Cys
            420                 425                 430

Asp Asp Trp Tyr His Trp Pro Cys Val Gly Ile Met Thr Ala Pro Pro
        435                 440                 445

Glu Glu Met Gln Trp Phe Cys Pro Lys Cys Ala Asn Lys Lys Lys Asp
    450                 455                 460

Lys Lys His Lys Lys Arg Lys His Arg Ala His
465                 470                 475

<210> SEQ ID NO 64
<211> LENGTH: 1371
<212> TYPE: DNA

<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: nucleic acid PLC7

<400> SEQUENCE: 64

```
atgtccccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg agtttccca atcttcctta ttatattgat      180
ggtgatgtta aattaacaca gtctatggcc atcatacgtt atatagctga caagcacaac     240
atgttgggtg ttgtccaaa agagcgtgca gagatttcaa tgcttgaagg agcggttttg      300
gatattagat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgttttaaa     540
aaacgtattg aagctatccc acaaattgat aagtacttga atccagcaa gtatatagca      600
tggcctttgc agggctggca agccacgttt ggtggtggcg accatcctcc aaaatcggat     660
ctggaagttc tgttccaggg gcccctggga tccgagtatg aggatggccg ggctttggc      720
attggagagc tggtgtgggg gaaacttcgg ggcttctcct ggtggccagg ccgaattgtg     780
tcttggtgga tgacaggccg gagccgagca gctgaaggca ctcgctgggt catgtggttc     840
ggagatggca agttctcagt ggtgtgtgtg gagaagctca tgccgctgag ctccttctgc     900
agtgcattcc accaggccac ctacaacaag cagcccatgt accgcaaagc catctacgaa     960
gtcctccagg tggccagcag ccgtgccggg aagctgtttc agcttgcca tgacagtgat     1020
gaaagtgaca gtggcaaggc tgtggaagtg cagaacaagc agatgattga atgggccctc    1080
ggtggcttcc agccctcggg tcctaagggc ctggagccac atctagcgg caatagtaac     1140
gctaacagcc gcgggccgag cttcagcagc ggcctggtgc cgttaagctt gcgcggcagc    1200
catgagcagg tgttcgccgt ggagagcatc cggaagaagc gcgtgcggaa gggtaaagtc    1260
gagtatctgg tgaagtggaa aggatggccc ccaaagtaca gcacgtggga gccagaagag    1320
cacatcttgg accccgcct cgtcatggcc tacgaggaga aggaggagtg a              1371
```

<210> SEQ ID NO 65
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein PLC7

<400> SEQUENCE: 65

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60
```

```
Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
            130                 135                 140

Gly Asp His Val Thr His Pro Asp Phe Met Leu Tyr Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
                195                 200                 205

Thr Phe Gly Gly Gly Asp His Pro Pro Lys Ser Asp Leu Glu Val Leu
210                 215                 220

Phe Gln Gly Pro Leu Gly Ser Glu Tyr Glu Asp Gly Arg Gly Phe Gly
225                 230                 235                 240

Ile Gly Glu Leu Val Trp Gly Lys Leu Arg Gly Phe Ser Trp Trp Pro
                245                 250                 255

Gly Arg Ile Val Ser Trp Trp Met Thr Gly Arg Ser Arg Ala Ala Glu
                260                 265                 270

Gly Thr Arg Trp Val Met Trp Phe Gly Asp Gly Lys Phe Ser Val Val
                275                 280                 285

Cys Val Glu Lys Leu Met Pro Leu Ser Ser Phe Cys Ser Ala Phe His
                290                 295                 300

Gln Ala Thr Tyr Asn Lys Gln Pro Met Tyr Arg Lys Ala Ile Tyr Glu
305                 310                 315                 320

Val Leu Gln Val Ala Ser Ser Arg Ala Gly Lys Leu Phe Pro Ala Cys
                325                 330                 335

His Asp Ser Asp Glu Ser Asp Ser Gly Lys Ala Val Glu Val Gln Asn
                340                 345                 350

Lys Gln Met Ile Glu Trp Ala Leu Gly Gly Phe Gln Pro Ser Gly Pro
                355                 360                 365

Lys Gly Leu Glu Pro Pro Ser Ser Gly Asn Ser Asn Ala Asn Ser Arg
                370                 375                 380

Gly Pro Ser Phe Ser Ser Gly Leu Val Pro Leu Ser Leu Arg Gly Ser
385                 390                 395                 400

His Glu Gln Val Phe Ala Val Glu Ser Ile Arg Lys Lys Arg Val Arg
                405                 410                 415

Lys Gly Lys Val Glu Tyr Leu Val Lys Trp Lys Gly Trp Pro Pro Lys
                420                 425                 430

Tyr Ser Thr Trp Glu Pro Glu Glu His Ile Leu Asp Pro Arg Leu Val
                435                 440                 445

Met Ala Tyr Glu Glu Lys Glu Glu
450                 455
```